United States Patent
Jones et al.

(10) Patent No.: US 7,067,277 B1
(45) Date of Patent: Jun. 27, 2006

(54) CHIMERIC G PROTEINS AND USES THEREOF

(75) Inventors: Kenneth A. Jones, Bergenfield, NJ (US); Mary W. Walker, Midland Park, NJ (US); Joseph Tamm, Hawthorne, NJ (US); Theresa A. Branchek, Teaneck, NJ (US); Christophe P. G. Gerald, Ridgewood, NJ (US)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/471,572

(22) Filed: Dec. 23, 1999

(51) Int. Cl.
- *C12N 15/12* (2006.01)
- *C12N 15/63* (2006.01)
- *C12N 15/00* (2006.01)
- *C07H 21/04* (2006.01)
- *C07K 14/00* (2006.01)

(52) U.S. Cl. .................. 435/69.1; 435/325; 435/320.1; 536/23.4; 530/350

(58) Field of Classification Search ................ 435/69.1, 435/325, 320.1; 536/23.4; 530/350
See application file for complete search history.

(56) References Cited

FOREIGN PATENT DOCUMENTS

| WO | 9748820 | 12/1997 |
|---|---|---|
| WO | 9816557 | 4/1998 |
| WO | 9905177 | 2/1999 |
| WO | 9914344 | 3/1999 |
| WO | 9918211 | 4/1999 |

OTHER PUBLICATIONS

Maurice et al. Identification of G alpha 11 as the phosphatase C-activating G-protein of turkey erythrocytes. Biochem. J. 1993. vol. 290 (Pt 3) pp. 765-770.*

Fino Silva I et al. Characterization of a G-protein alpha-subunit gene from the nematode *Caenorhabditis elegans*. J Mol Biol. Oct. 20, 1990;215(4):483-7.*

Conklin BR et al. Substitution of three amino acids switches receptor specificity of Gq alpha to that of Gi alpha. Nature. May 20, 1993;363(6426):274-6.*

Milligan G, Rees S. Chimaeric G alpha proteins: their potential use in drug discovery. Trends Pharmacol Sci. Mar. 1999;20(3):118-24.*

Alberts et al. Molecular Biology of the Cell. 1989, Garland Publishing, Inc. New York, pp. 183 and 534.*

Mickle JE et al. Genotype-phenotype relationships in cystic fibrosis. Med Clin North Am. May 2000;84(3):597-607.*

Voet et al. Biochemistry. 1990. John Wiley & Sons, Inc. pp. 126-128 and 228-234.*

Yan et al., Two-amino acid molecular switch in an epithelial morphogen that regulates binding to two distinct receptors. Scienc 290: 523-527, 2000.*

Conklin, B.R., et al.,Carboxyl-Terminal Mutations of $G_{qa}$ and $G_{sa}$ That Alter the Fidelity of Receptor Activation, Molecular Pharmacology (1996) 50: 885-890.

Coward, P., et al., Chimeric G Proteins Allow a High-Throughput Signaling Assay of $G_i$-Coupled Receptors, Analytical Biochemistry (1999) 270: 242-248.

Kostenis, E., et al., The N-terminal Extension of $Ga_q$ Is Critical for Constraining the Selectivity of Receptor Coupling, J. of Biological Chemistry (1997) 272(31): 19107-19110.

Kostenis, E., et al., Functional Characterization of a Series of Mutant G Protein $\alpha_q$ Subunits Displaying Promiscuous Receptor Coupling Properties, J. of Biological Chemistry (1998) 273(28): 17886-17892.

Milligan, G., et al., Chimaeric $G\alpha$ proteins: their potential use in drug discovery, TiPS (1999) 20: 118-124.

Tsu, R.C., et al., Role of Amino- and Carboxyl-Terminal Regions of $G_{az}$ in the Recognition of $G_i$-Coupled Receptors, Molecular Pharmacology (1997) 52: 38-45.

* cited by examiner

*Primary Examiner*—Joseph Murphy
(74) *Attorney, Agent, or Firm*—Stephen G. Kalinchak

(57) ABSTRACT

This invention provides isolated nucleic acids encoding chimeric G proteins, vectors comprising nucleic acids encoding chimeric G proteins, cells comprising such vectors, processes of determining agonists and antagonists of mammalian G protein-coupled receptors utilizing chimeric G proteins, processes of determining compounds which bind to mammalian G protein-coupled receptors utilizing chimeric G proteins, processes for making a composition of matter which specifically binds to a mammalian G protein-coupled receptor utilizing chimeric G proteins, processes for preparing a composition which comprises admixing a carrier and a pharmaceutically effective amount of a chemical compound identified by a process of the invention utilizing chimeric G proteins, processes of identifying a ligand for a mammalian G protein-coupled receptor utilizing chimeric G proteins, and processes of screening a plurality of independent clones to identify and isolate a clone encoding a mammalian G protein-coupled receptor utilizing chimeric G proteins.

6 Claims, 8 Drawing Sheets

FIGURE 2A

*C. elegans* Gα<sub>q/z5</sub>

```
  1 MACCLSEEAR EQKRINQEIE KQLQRDKRNA RRELKLLLLG TGESGKSTFI KQMRIIHGQG
 61 YSEEDKRAHI RLVYQNVFMA IQSMIRAMDT LDIKFGNESE ELQEKAAVVR EVDFESVTSF
121 EEPYVSYIKE LWEDSGIQEC YDRRREYQLT DSAKYYLSDL RRLAVPDYLP TEQDILRVRV
181 PTTGIIEYPF DLEQIIFRMV DVGGQRSERR KWIHCFENVT SIMFLVALSE YDQVLVECDN
241 ENRMEESKAL FRTIITYPWF TNSSVILFLN KKDLLEEKIL YSHLADYFPE YDGPPRDPIA
301 AREFILKMFV DLNPDADKII YSHFTCATDT ENIRFVFAAV KDTILQHNLK YIGLC
```

*C. elegans* Gα<sub>q/z9</sub>

```
  1 MACCLSEEAR EQKRINQEIE KQLQRDKRNA RRELKLLLLG TGESGKSTFI KQMRIIHGQG
 61 YSEEDKRAHI RLVYQNVFMA IQSMIRAMDT LDIKFGNESE ELQEKAAVVR EVDFESVTSF
121 EEPYVSYIKE LWEDSGIQEC YDRRREYQLT DSAKYYLSDL RRLAVPDYLP TEQDILRVRV
181 PTTGIIEYPF DLEQIIFRMV DVGGQRSERR KWIHCFENVT SIMFLVALSE YDQVLVECDN
241 ENRMEESKAL FRTIITYPWF TNSSVILFLN KKDLLEEKIL YSHLADYFPE YDGPPRDPIA
301 AREFILKMFV DLNPDADKII YSHFTCATDT ENIRFVFAAV KDTILQNNLK YIGLC
```

*C. elegans* Gα<sub>q/s9</sub>

```
  1 MACCLSEEAR EQKRINQEIE KQLQRDKRNA RRELKLLLLG TGESGKSTFI KQMRIIHGQG
 61 YSEEDKRAHI RLVYQNVFMA IQSMIRAMDT LDIKFGNESE ELQEKAAVVR EVDFESVTSF
121 EEPYVSYIKE LWEDSGIQEC YDRRREYQLT DSAKYYLSDL RRLAVPDYLP TEQDILRVRV
181 PTTGIIEYPF DLEQIIFRMV DVGGQRSERR KWIHCFENVT SIMFLVALSE YDQVLVECDN
241 ENRMEESKAL FRTIITYPWF TNSSVILFLN KKDLLEEKIL YSHLADYFPE YDGPPRDPIA
301 AREFILKMFV DLNPDADKII YSHFTCATDT ENIRFVFAAV KDTILQMHLR QYELL
```

*C. elegans* Gα<sub>q/s21</sub>

```
  1 MACCLSEEAR EQKRINQEIE KQLQRDKRNA RRELKLLLLG TGESGKSTFI KQMRIIHGQG
 61 YSEEDKRAHI RLVYQNVFMA IQSMIRAMDT LDIKFGNESE ELQEKAAVVR EVDFESVTSF
121 EEPYVSYIKE LWEDSGIQEC YDRRREYQLT DSAKYYLSDL RRLAVPDYLP TEQDILRVRV
181 PTTGIIEYPF DLEQIIFRMV DVGGQRSERR KWIHCFENVT SIMFLVALSE YDQVLVECDN
241 ENRMEESKAL FRTIITYPWF TNSSVILFLN KKDLLEEKIL YSHLADYFPE YDGPPRDPIA
301 AREFILKMFV DLNPDADKII YSHFTCATDT ENIRRVFNDC RDIIQRMHLR QYELL
```

*C. elegans* Gα<sub>q/i3(5)</sub>

```
  1 MACCLSEEAR EQKRINQEIE KQLQRDKRNA RRELKLLLLG TGESGKSTFI KQMRIIHGQG
 61 YSEEDKRAHI RLVYQNVFMA IQSMIRAMDT LDIKFGNESE ELQEKAAVVR EVDFESVTSF
121 EEPYVSYIKE LWEDSGIQEC YDRRREYQLT DSAKYYLSDL RRLAVPDYLP TEQDILRVRV
181 PTTGIIEYPF DLEQIIFRMV DVGGQRSERR KWIHCFENVT SIMFLVALSE YDQVLVECDN
241 ENRMEESKAL FRTIITYPWF TNSSVILFLN KKDLLEEKIL YSHLADYFPE YDGPPRDPIA
301 AREFILKMFV DLNPDADKII YSHFTCATDT ENIRFVFAAV KDTILQHNLK ECGLY
```

FIGURE 2B

D. melanogaster Gα$_{q/z5}$

```
  1 MECCLSEEAK EQKRINQEIE KQLRRDKRDA RRELKLLLLG TGESGKSTFI KQMRIIHGSG
 61 YSDEDKRGYI KLVFQNIFMA MQSMIKAMDM LKISYGQGEH SELADLVMSI DYETVTTFED
121 PYLNAIKTLW DDAGIQECYD RRREYQLTDS AKYYLKDLDR VAQPAYLPTE QDILRVRVPT
181 TGIIEYPFDL EEIRFRMVDV GGQRSERRKW IHCFENVTSI IFLVALSEYD QILFESDNEN
241 RMEESKALFR TIITYPWFQN SSVILFLNKK DLLEEKIMYS HLVDYFPEYD GPQRDAITAR
301 EFILRMFVDL NPDSEKIIYS HFTCATDTEN IRFVFAAVKD TILQSNLKYI GLC
```

FIGURE 3
hNPFF1  NPFF 1μM
hNPFF1 + cG$\alpha_{q/z5}$
NPFF 1μM
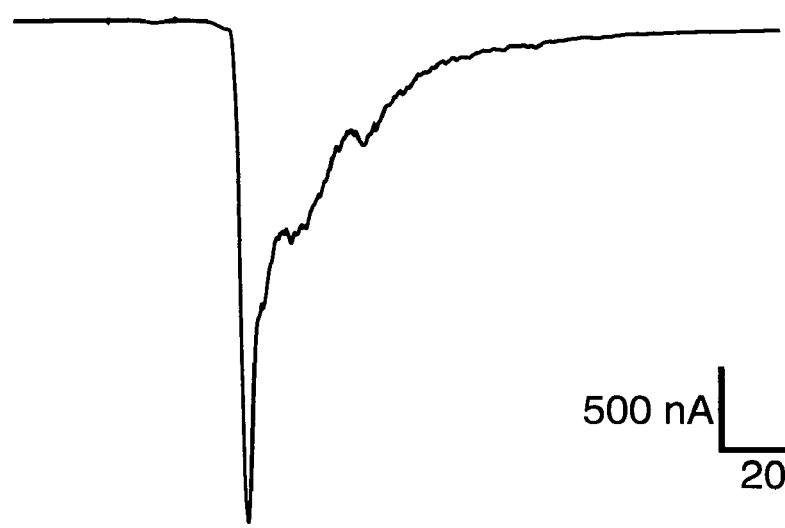
500 nA
20 s
hNPFF1 + cG$\alpha_{q/z5}$
+ 190 ng EGTA
NPFF 1μM

FIGURE 4
Human D1
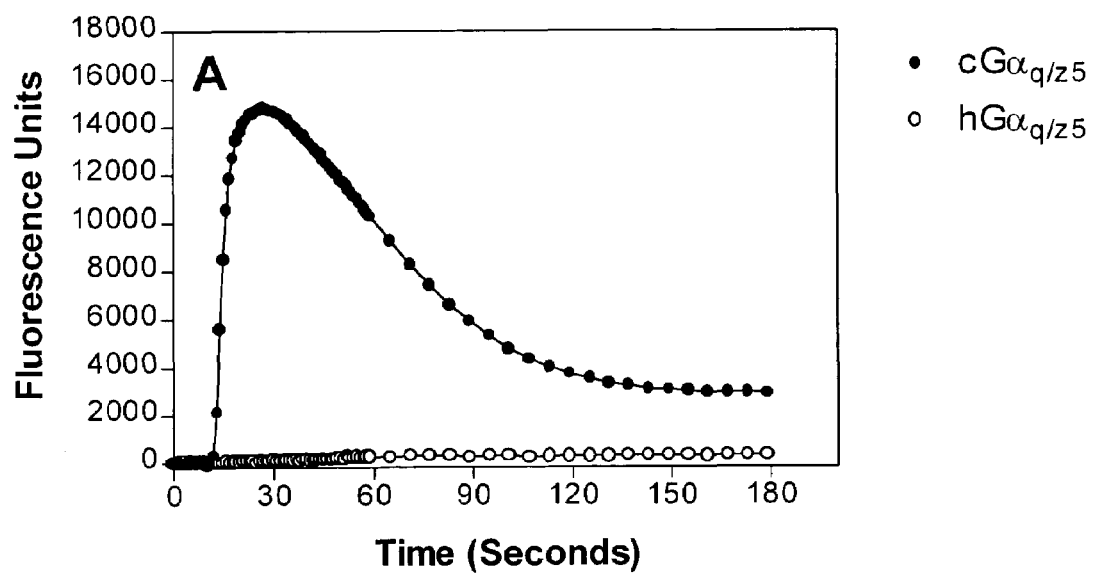
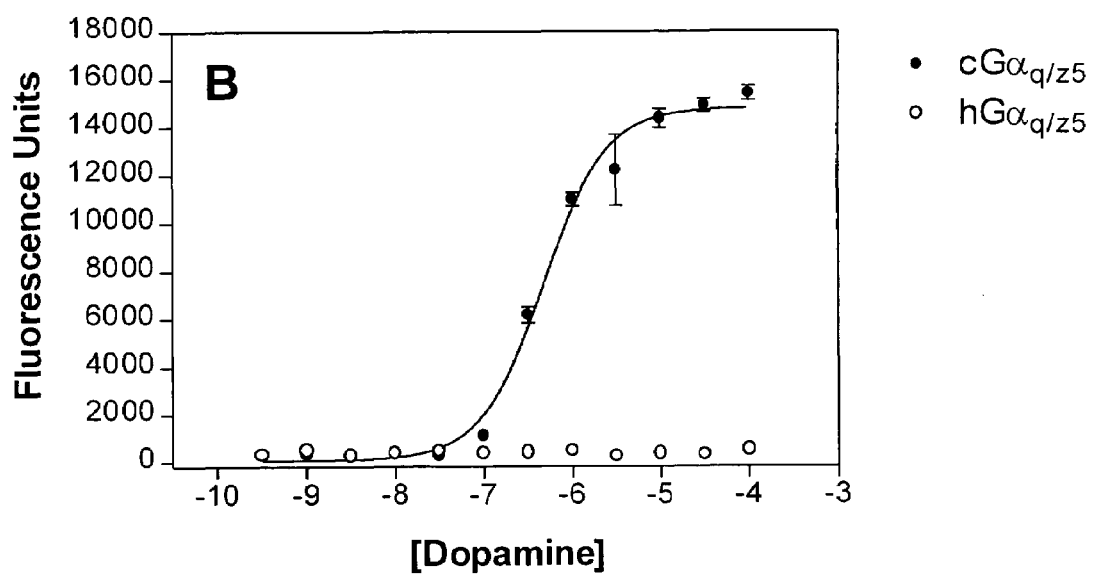

FIGURE 5A

```
                         *         20         *         40         *
GBQ_HUMAN  : MTLESIMACCLSEEAKEARRINDEIERQLRRDKRDARRELKLLLLGTGES
GBQ_CANFA  : MTLESIMACCLSEEAKEARRINDEIERQLRRDKRDARRELKLLLLGTGES
GBQ_MOUSE  : MTLESIMACCLSEEAKEARRINDEIERHVRRDKRDARRELKLLLLGTGES
GBQ_XENLA  : MTLESIMACCLSEEAEEARRINDEIERQLRRDKRDARRELKLLLLGTGES
GBQ_PATYE  : ~~~~~~MACCLSEEAKEQKRINCEIEKELRKAKRDARRELKLLLLGTGES
GBQ_LYMST  : ~~~~~~MACCIPDELKEQKRINQEIERQLKRDKRDARRELKLLLLGTGES
GBQ1_DROM  : ~~~~~~MECCLSEEAKEQKRINQEIEKQLRRDKRDARRELKLLLLGTGES
GBQ3_DROM  : ~~~~~~MECCLSEEAKEQKRINQEIEKQLRRDKRDARRELKLLLLGTGES
GBQ_HOMAM  : ~~~~~~MACCLSEEAKEQKRINQEIERQLRKDKRDARRELKLLLLGTGES
GBQ_LIMPO  : ~~~~~~MACCLSEEGKEQKRINQEIERQLRKDKRDARRELKLLLLGTGES
GBQ_LOLFO  : ~~~~~~MACCLSEEAKEQKRINQEIEKQLRRDKRDARRELKLLLLGTGES
GBQ_CAEEL  : ~~~~~~MACCLSEEAREQKRINQEIEKQLQRDKRNARRELKLLLLGTGES
GBQ_GEOCY  : ~~~~~~MSCLLSEEERLQKRINTRINRELQRDHKDAKKEIKLLLLGTGES

60         *         80         *        100
GBQ_HUMAN  : GKSTFIKQMRIIHGSGYSDEDKRGFTKLVYQNIFTAMQAMIRAMDTLKIP
GBQ_CANFA  : GKSTFIKQMRIIHGSGYSDEDKRGFTKLVYQNIFTAMQAMIRAMDTLKIP
GBQ_MOUSE  : GKSTFIKQMRIIHGSGYSDEDKRGFTKLVYQNIFTAMQAMIRAMDTLKIP
GBQ_XENLA  : GKSTFIKQMRIIHGSGYSDEDKRGFTKLVYQNIFSAMQAMIRAMETLKIP
GBQ_PATYE  : GKSTFIKQMRIIHGTGYSEEDKRGFIKIVYQNIFMAMHSMIRAMDTIKIS
GBQ_LYMST  : GKSTFIKQMRIIHGAGYSDEDKRSHIKIVYQNIFMAMHAMIRAMDTINIQ
GBQ1_DROM  : GKSTFIKQMRIIHGSGYSDEDKRGYIKLVFQNIFMAMQSMIKAMDMLKIS
GBQ3_DROM  : GKSTFIKQMRIIHGSGYSDEDKRGYIKLVFQNIFMAMQSMIKAMDMLKIS
GBQ_HOMAM  : GKSTFIKQMRIIHGAGYSDEDKRGFIKLVFQNIFMAMQSMIRAMDLLQIS
GBQ_LIMPO  : GKSTFIKQMRIIHGQGYSDDDKSYIKLVYQNIIMAMQSMNKAMEMLKIS
GBQ_LOLFO  : GKSTFIKQMRIIHGSGYSEEDRKGFEKIVYQNIFSAIQTLIAAMETLSLE
GBQ_CAEEL  : GKSTFIKQMRIIHGQGYSEEDKRAHIRLVYQNVFMAIQSMIRAMDTLDIK
GBQ_GEOCY  : GKSTFIKQMRIIHGKGYSKQDCLEYKNLVFRNILMSVHSMLQATAELKIA

*        120         *        140         *
GBQ_HUMAN  : YKYEHNK--AHAQLVREVDVEKVS----AFENPYVDAIKSLWNDPGIQEC
GBQ_CANFA  : YKYEHNK--AHAQLVREVDVEKVS----AFENPYVDAIKSLWNDPGIQEC
GBQ_MOUSE  : MKYEHNK--AHAQLVREVDVEKVS----AFENPYVDAIKSLWNDPGIQEC
GBQ_XENLA  : YKYEHNK--GHALLVREVDVEKVA----SFENPYVDAIKYLWNDPGIQEC
GBQ_PATYE  : FEVADNE--ENAIMIRQVDYETVT----TLDSQSVEAILSLWADAGIQEC
GBQ_LYMST  : YINPANR--ENGNMIRQIDYETVT----TEDKPCVDAIISLWNDDGIQEC
GBQ1_DROM  : YGQGEHS--ELADLVMSIDYETVT----TEEDPYLNAIKTLWDDAGIQEC
GBQ3_DROM  : YGQGEHS--ELADLVMSIDYETVT----TEEDPYLNAIKTLWDDAGIQEC
GBQ_HOMAM  : YGDSANI--EHADLVRSVDYESVT----TEEPYVTAMNSLWQDTGIHHC
GBQ_LIMPO  : YKDRNNI--ENAELVLSVDYETVT----TRDSPYVEAIKSLWVDPGIQEC
GBQ_LOLFO  : YKDPSN--NEHAEFLNSIDADSAD----IFEDGHVTAIKGCWTDPGMQEC
GBQ_CAEEL  : FGNESEELQEKAAVVREVDFESVT----SEEEPYVSYIKELWEDSGIQEC
GBQ_GEOCY  : YIDPD--AQRHVQLLMALRPETAQ----SLGGETCEAIRKLWQDAGVQEC
```

FIGURE 5B

```
                    160         *         180         *         200
GBQ_HUMAN  : YDRRREYQ-LSDSTKYYLNDLDRVADPAYLPTQQDVLRVRVPTIGIIEYP
GBQ_CANFA  : YDRRREYQ-LSDSTKYYLNDLDRVADPAYLPTQQDVLRVRVPTIGIIEYP
GBQ_MOUSE  : YDRRREYQ-LSDSTKYYLNDLDRVADPSYLPTQQDVLRVRVPTIGIIEYP
GBQ_XENLA  : YDRRREYQ-LSDSTKYYLNDLDRIATHGYLPTQQDVLRVRVPTIGIIEYP
GBQ_PATYE  : YDRRREYQ-LTDSAKYYLDAVDRIAEPNYLPTLQDILRVRVPTIGIIEYP
GBQ_LYMST  : YDRRREYQ-LTDSAKYYLDSVERISQQDYLPTLQDILRVRVPTIGIIEYP
GBQ1_DROM  : YDRRREYQ-LTDSAKYYLSDLARIEQADYLPTEQDILRARVPTIGILEYP
GBQ3_DROM  : YDRRREYQ-LTDSAKYYLKDLDRVAQPAYLPTEQDILRVRVPTIGIIEYP
GBQ_HOMAM  : YDRRREYQ-LTDSAKYYLTDLDRIAAKDYVSTLQDILRVRAPTIGIIEYP
GBQ_LIMPO  : YDRRREYQ-LTDSAKYYLNDIDRIAVPNYLPTQQDILRVRVPTIGIIEYP
GBQ_LOLFO  : YDRRREYQ-LTDSAKYYLDDVERIHEPGYIPTLQDILRVRVPTIGIIEYP
GBQ_CAEEL  : YDRRREYQ-LTDSAKYYLSDLRRLAVPDYLPTEQDILRVRVPTIGIIEYP
GBQ_GEOCY  : YQRRNEYQ-LSDSTKYYLDLPRISSNDYVPTTQDVLRVRVPTIGINEYP

*         220         *         240         *
GBQ_HUMAN  : FDLQSVIFRMVDVGGQRSERRKWIHCFENVTSIMFLVALSEYDQVLVESD
GBQ_CANFA  : FDLQSVIFRMVDVGGQRSERRKWIHCFENVTSIMFLVALSEYDQVLVESD
GBQ_MOUSE  : FDLQSVIFRMVDVGGQRSERRKWIHCFENVTSIMFLVALSEYDQVLVESD
GBQ_XENLA  : FDLQSVIFRMVDVGGQRSERRKWIHCFENVTSIMFLVALSEYDQVLVESD
GBQ_PATYE  : FDLDSIIFRMVDVGGQRSERRKWIHCFENVTSIMFLVALSEYDQVLVESD
GBQ_LYMST  : FDLDSIIFRMVDVGGQRSERRKWIHCFENVTSIMFLVALSEYDQVLVESD
GBQ1_DROM  : FDLDGIVFRMVDVGGQRSERRKWIHCFENVTSIIFLVALSEYDQILFESD
GBQ3_DROM  : FDLEEIRFRMVDVGGQRSERRKWIHCFENVTSIIFLVALSEYDQILFESD
GBQ_HOMAM  : FDLEEIRFRMVDVGGQRSERRKWIHCFENVTSIIFLVALSEYDQILFESD
GBQ_LIMPO  : FILDSIIFRMVDVGGQRSERRKWIHCFENVTSIIFLVALSEYDQILFESD
GBQ_LOLFO  : FDLYSIIFRMVDVGGQRSERRKWIHCFENVTSIMFLVALSEYDQVLVESD
GBQ_CAEEL  : FDLEQIIFRMVDVGGQRSERRKWIHCFENVTSIMFLVALSEYDQVLVECD
GBQ_GEOCY  : FTINKIIFKMVDVGGQRSERRKWIHCFDHVTSVMFLVAISEYDQILVEAD

260         *         280         *         300
GBQ_HUMAN  : N-ENRMEESKALFRTIITYPWFQNSSVILFLNKKDLLEEKIMYSHLVDYF
GBQ_CANFA  : N-ENRMEESKALFRTIITYPWFQNSSVILFLNKKDLLEEKIMYSHLVDYF
GBQ_MOUSE  : N-ENRMEESKALFRTIITYPWFQNSSVILFLNKKDLLEEKIMYSHLVDYF
GBQ_XENLA  : N-ENRMEESKALFRTIITYPWFQNSSVILFLNKKDLLEEKIMYSHLVDYF
GBQ_PATYE  : N-ENRMEESKALFRTIITYPWFQNSSVILFLNKKDLLEEKIMHSHLVDYF
GBQ_LYMST  : N-ENRMEESKALFRTIITYPWFQNSSVILFLNKKDLLEEKIMHSHLVDYF
GBQ1_DROM  : N-ENRMEESKALFRTIITYPWFQNSSVILFLNKKDLLEEKIMYSHLVDYF
GBQ3_DROM  : N-ENRMEESKALFRTIITYPWFQNSSVILFLNKKDLLEEKIMYSHLVDYF
GBQ_HOMAM  : N-ENRMEESKALFKTIITYPWFQHSSVILFLNKKDLLEEKIMYSHLVDYF
GBQ_LIMPO  : N-ENRMEESKALFKTIITYPWFLNSSVILFLNKKDLLEEKIMFSHLVDYF
GBQ_LOLFO  : NEENRMEESKALFRTIITYPWFQNSSVILFLNKKDLLEEKIMTSHLADYF
GBQ_CAEEL  : N-ENRMEESKALFRTIITYPWFTNSSVILFLNKKDLLEEKILYSHLADYF
GBQ_GEOCY  : SRVNRMVESLHLFNIIISYPWFNKSSIILFLNKKDLLEEKVMHSHLIDYF
```

FIGURE 5C

```
                             *         320         *         340         *
GBQ_HUMAN  : PEYDGPQRDAQAAREFILKMFVDLNPDSDKILYSHFTCATDTENIREVFA
GBQ_CANFA  : PEYDGPQRDAQAAREFILKMFVDLNPDSDKILYSHFTCATDTENIREVFA
GBQ_MOUSE  : PEYDGPQRDAQAAREFILKMFVDLNPDSDKILYSHFTCATDTENIREVFA
GBQ_XENLA  : PEYDGPQRDAQAAREFILKMFVDLNPDSDKILYSHFTCATDTENIREVFA
GBQ_PATYE  : PEFDGQKKDAQGAREFTLRMFVDLNPDPDKILYSHFTCATDTENIREVFA
GBQ_LYMST  : PEFDGPKKEASTAREFILKMFVELNPDPDKILYSHFTCATDTENIREVFA
GBQ1_DROM  : PEYDGPKQDHAAAKQFVLKKYLACNPDPERQCYSHFTTATDTENIKLVFC
GBQ3_DROM  : PEYDGPQRDAITAREFILRMFVDLNPDSEKILYSHFTCATDTENIREVFA
GBQ_HOMAM  : PEYDGPRKDAIAAREFILRMFVELNPDPEKILYSHFTCATDTENIREVFA
GBQ_LIMPO  : PEYDGPKKDAVQGREFILKMFVDLNPDSEKILYSHFTCATDTENIREVFA
GBQ_LOLFO  : PDYDGPKCDYEAAREFMMDSYMDLNEDKEKMLYYHYTCATDTENIREVFA
GBQ_CAEEL  : PEYDGPPRDPIAAREFILKMFVDLNPDADKILYSHFTCATDTENIREVFA
GBQ_GEOCY  : EEYDGPKCDHVSARESIAKMFISINDMRSADIYPHFTCATDTENIKEVFD

360         *
GBQ_HUMAN  : AVKDTILQLNLKEYNAM~~~ : 359
GBQ_CANFA  : AVKDTILQLNLKEYNLV~~~ : 359
GBQ_MOUSE  : AVKDTILQLNLKEYNLV~~~ : 359
GBQ_XENLA  : AVKDTILQLNLKEYNLV~~~ : 359
GBQ_PATYE  : AVKDTILQLNLKEYNLV~~~ : 353
GBQ_LYMST  : AVKDTILQLNLKEYNLV~~~ : 353
GBQ1_DROM  : AVKDTIMQNALKEFNLG~~~ : 353
GBQ3_DROM  : AVKDTILQSNLKEYNLV~~~ : 353
GBQ_HOMAM  : AVKDTILQLNLKEYNLV~~~ : 353
GBQ_LIMPO  : AVKDTILQLNLKEYNLV~~~ : 353
GBQ_LOLFO  : AVKDTILQLNLKEYNLV~~~ : 354
GBQ_CAEEL  : AVKDTILQHNLKEYNLV~~~ : 355
GBQ_GEOCY  : VVKNHILQQHITE--VWPGL : 355
```

CHIMERIC G PROTEINS AND USES THEREOF

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which the invention pertains.

Therapeutic Importance of G Protein-Coupled Receptors

Intercellular communication in multicellular organisms relies on numerous signal transduction pathways that allow chemical messages to be sensed extracellularly and converted into intracellular responses. One of the most ancient and well-diversified pathways uses G protein-coupled receptors (GPCRs) as the chemical sensor. GPCRs comprise a large family of transmembrane signaling proteins that are key to a variety of cellular activities including phototransduction, olfaction, neurotransmission, and endocrine function.

There are currently about 300 molecularly identified GPCRs and this number is rapidly growing. Estimates based on genomes that have been entirely sequenced suggest that there may be more than 1000 GPCRs in humans. The fact that a large proportion of prescribed drugs act on GPCRs coupled with the evidence of a large reserve of undiscovered genes suggests that these proteins will continue to be major targets for drug discovery for the foreseeable future.

Signaling Pathways Used by GPCRs

GPCRs mediate diverse cellular responses to external stimuli through their interaction with a single class of proteins known as heterotrimeric G proteins (G proteins). These proteins are composed functionally of two subunits, an α subunit that possesses GPCR-recognition and GTP-binding domains, and a dimer formed by β and γ subunits (Bourne, 1997; Lambright et al., 1996). Stimulated by agonist binding, GPCRs induce a conformational change in the G protein that facilitates the exchange of GDP for GTP bound to the α subunit. In the GTP-bound state, the α subunit is free to dissociate from the βγ dimer, permitting the two subunits to independently interact with a number of membrane-bound effector proteins including enzymes and ion channels.

To date, there are 17 Gα subunits that have been cloned (Simon et al., 1991). These fall broadly into four classes: those that activate phospholipase C ($G\alpha_q$, $G\alpha_{11}$, $G\alpha_{14}$, $G\alpha_{15}$, and $G\alpha_{16}$), those that stimulate adenylate cyclase ($G\alpha_s$ and isoforms), those that mediate inhibition of adenylate cyclase and also permit interaction with a variety of other effectors through release of βγ subunits ($G\alpha_i$ and $G\alpha_o$ isoforms), and finally $G\alpha_{12}$ and $G\alpha_{13}$ whose regulatory functions are less well understood. By detecting and discriminating among structural features of both βγ and Gα, the individual GPCR activates only a subset of available G proteins (Bourne, 1997).

The "funneling" of signaling events through specific classes of G proteins has had important consequences for the design of assays to test the functional status of a given receptor. For example, receptors that couple strongly to $G\alpha_q$, such as $\alpha_{1A}$-adrenoceptors, 5-$HT_2$, receptors, or H1 histamine receptors, activate phospholipase C isoforms, initiating a rise in inositol phosphates (IP3) and a release of calcium from intracellular stores. Specific assays have been developed to measure the release of these signaling molecules. Likewise, other assays have been developed for measuring accumulation or depletion of cAMP (from stimulation or inhibition of adenylate cyclase) due to stimulation of receptors coupling either to $G\alpha_s$ or $G\alpha_i$, respectively. A myriad of other assays have been elaborated that measure ion channel, GPTγS binding, MAP kinase, or transcriptional activities. In further elaborations of these methods, artificial "reporter genes" are used to provide a simplified endpoint initiated by some of the above cellular responses.

Ligand Identification for GPCR "Orphan" Receptors

The discovery of new GPCRs has outpaced the identification of new natural ligands, leading to a growing list of "orphan" G protein-coupled receptors whose ligand is unknown. Identifying the ligands for these orphan receptors is critical for determining their biological importance and will permit investigations into receptor pharmacology and drug design. While it is possible to identify ligands by binding, such assays depend upon the availability of high affinity radiolabeled ligands, and often on high levels of expression of the cloned receptor. On the other hand, functional activity can be elicited using unmodified, naturally occurring ligands applied to cells expressing moderate densities of receptor. The primary disadvantage of the functional approach is not knowing which class of G protein will couple efficiently to the orphan receptor. Although much progress has been made toward identifying motifs within the intracellular portions of GPCRs that bind G proteins, currently it is not possible to predict which class of G protein will couple to a given receptor. This uncertainty requires the employment of multiple functional assays for each orphan receptor in order to cover all possible signal transduction pathways. The availability of a single, genetically modified G protein that could couple universally to the vast majority of GPCRs would be an extremely useful tool for the study of orphan receptors and for the development of new therapeutic agents targeting GPCRs.

"Promiscuous" G Proteins and Modified G Proteins

The design of a universal functional assay for all GPCRs is a highly sought after goal for the pharmaceutical industry. Such an assay would eliminate the need to run multiple parallel assays for each receptor. Work on the $G\alpha_{16}$ subunit (Offermans and Simon, 1995) showed that a single G protein can "route" receptors that normally couple to inhibition of adenylate cyclase to stimulation of inositol phosphate production (Offermanns and Simon, 1995). Such a system can take advantage of instrumentation that detects $Ca^{++}$ mobilization via fluorescent dyes in a multiwell plate format suitable for mass screening of compound libraries. Unfortunately, while heterologous expression systems incorporating $G\alpha_{16}$ are amenable to mass screening, there are a significant number of GPCRs that do not couple well to this G protein, reducing its general utility for screening orphan receptors.

Studies of the three dimensional structure of native G proteins (Lambright et al., 1996) and the functional activities of chimeric G proteins (see for review, Milligan and Rees, 1999) point to two regions of the Gα subunit that are involved in receptor recognition. Conklin and co-workers (Conklin et al., 1993) provided experimental evidence that the extreme C-terminal regions of $G\alpha_q$, $G\alpha_s$, and $G\alpha_{i2}$ are important for directing targeting to the receptor. For example, replacing the last five amino acids of $G\alpha_q$ with the corresponding amino acids from $G\alpha_{i2}$, permitted three receptors, which normally couple to $G\alpha_{i/o}$, to stimulate phospholipase C (PLC). Similarly, replacing with the terminal five amino acids of $G\alpha_s$, permitted stimulation of PLC by the vasopressin V2 receptor, which normally activates adenylate cyclase (Conklin et al., 1996). Other experiments, in which $G\alpha_s$ was altered by the C-terminal amino acids of $G\alpha_q$, demonstrated the generality of the finding that a given G protein can be re-directed by replacing the C-terminus of a given $G\alpha$ "backbone" with the appropriate C-terminus of another $G\alpha$ subunit (see for review, Milligan and Rees, 1999). Thus, the C-terminus of $G\alpha$ is one important determinant for GPCR recognition and may be modified to channel responses from the preferred signaling pathway to another one that would be amenable to automation.

The N-terminus of $G\alpha$ is also involved in directing G protein to a target receptor, but the specificity for this is much less well understood. Kostenis and co-workers (Kostenis et al., 1997; Kostenis et al., 1998) noted that the N-termini of $G\alpha_q$ and $G\alpha_{11}$ are unique in that they contain a six amino acid extension not found in other $G\alpha$ subunits. Deletion of this extension permitted GPCRs that do not normally couple to wild-type $G\alpha_q$, to productively couple to the mutant and activate PLC. Although N-terminal deletion mutants of $G\alpha_q$ improve coupling to $G\alpha_{i/o}$-coupled receptors, the amplitude of second messenger response in many instances is low and not sufficient for mass screening applications.

Use of Ancestral G Proteins

Sequence analysis of $G\alpha$ genes from organisms spanning multiple phyla suggests the existence of a primordial $G\alpha$ ancestor (Wilkie and Yokoyama, 1994; Seack et al., 1998; Suga et al., 1999; FIG. 1). Lower organisms having less elaborate second messenger pathways and effector protein targets might harbor $G\alpha$ homologues that are closer in structure to the ancestral protein. Further, these proteins may have the capacity to interact promiscuously with a wide variety of GPCRs because they lack structural motifs that subsequently evolved for the recognition of specific receptor subtypes. For example, in the search for primitive G proteins we noted that all invertebrate species, including *Caenorhabditis elegans* (*C. elegans*) and *Drosophila melanogaster* (*D. melanogaster*), lack the first six amino acids corresponding to the N-terminus of mammalian $G\alpha_q$ subunits. The use of $G\alpha$ subunits from species that appear evolutionarily early on the phylogenetic tree offers an approach to universal coupling that has not been previously described.

*C. elegans* is an attractive organism because its genome has been completely sequenced (The *C. elegans* Sequencing Consortium, 1998) and because, as a pseudocoelomate, it branches early in the phylogenetic tree (Keeton, 1980). *C. elegans* contains only a single homologue from each of the four major $G\alpha$ families: $G\alpha_q$, $G\alpha_i$, $G\alpha_s$, and $G\alpha_{12}$ (Jansen et al., 1999). This contrasts with mammals which have multiple isoforms within each of these families and, at the other phylogenetic extreme, yeast which has only two $G\alpha$ subunits (Simon et al., 1991). The single $G\alpha_q$ subunit of *C. elegans* may, therefore, couple to a wider range of GPCRs than any of its mammalian homologues. When combined with specific C-terminal tails derived from mammalian non-$G\alpha_q$ subunits, the resulting chimeric G proteins may be further enhanced in their ability to efficiently couple to mammalian GPCRs.

This application describes the use of $G\alpha_q$ subunits obtained from invertebrate organisms, using *C. elegans* and *D. melanogaster* as examples, as "backbones" for the construction of chimeras. One chimera in particular, composed of *C. elegans* $G\alpha_q$ ($cG\alpha_q$) and modified to contain on its C-terminus the five amino acids of human $G\alpha_z$ ($hG\alpha_z$), exhibits surprisingly robust coupling to 78% of a large sample of cloned GPCRs. Further described are uses for this $G\alpha$ chimera, and others, related to the identification of ligands for orphan GPCRs and for high-throughput screening of chemical compounds in functional assays.

SUMMARY OF THE INVENTION

The present invention provides an isolated nucleic acid encoding a chimeric G protein, wherein the chimeric G protein comprises an invertebrate $G\alpha q$ G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted or varies therefrom by no more than five amino acids, provided that at least five of the C-terminal amino acids of the chimeric G protein are present at the C-terminus of such vertebrate G protein.

The invention also provides a process for determining whether a chemical compound is a mammalian G protein-coupled receptor agonist which comprises contacting cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound is a mammalian G protein-coupled receptor agonist.

The invention further provides a process for determining whether a chemical compound is a mammalian G protein-coupled receptor agonist which comprises contacting a membrane preparation from cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound is a mammalian G protein-coupled receptor agonist.

In addition, the invention provides a process for determining whether a chemical compound is a mammalian G protein-coupled receptor antagonist which comprises contacting cells transfected with and expressing DNA encoding a chimeric G protein and expressing DNA encoding a mammalian G protein-coupled receptor, with the compound in the presence of a known mammalian G protein-coupled receptor agonist, under conditions permitting the activation of the mammalian G protein-coupled receptor, and detecting a decrease in mammalian G protein-coupled receptor activity, so as to thereby determine whether the compound is a mammalian G protein-coupled receptor antagonist.

The invention further provides a process for determining whether a chemical compound is a mammalian G protein-coupled receptor antagonist which comprises contacting a membrane preparation from cells transfected with and expressing DNA encoding a chimeric G protein and expressing DNA encoding a mammalian G protein-coupled receptor, with the compound in the presence of a known mammalian G protein-coupled receptor agonist, under conditions permitting the activation of the mammalian G protein-coupled receptor, and detecting a decrease in mammalian G protein-coupled receptor activity, so as to thereby determine whether the compound is a mammalian G protein-coupled receptor antagonist.

The invention also provides a process for determining whether a chemical compound specifically binds to and activates a mammalian G protein-coupled receptor, which comprises contacting cells producing a second messenger response, expressing the DNA encoding the mammalian G protein-coupled receptor, and expressing the DNA encoding a chimeric G protein, wherein such cells do not normally express the DNA encoding the chimeric G protein, with the chemical compound under conditions suitable for activation of the mammalian G protein-coupled receptor, and measuring the second messenger response in the presence and in the absence of the chemical compound, a change in the second messenger response in the presence of the chemical compound indicating that the compound activates the mammalian G protein-coupled receptor.

In addition, the invention provides a process for determining whether a chemical compound specifically binds to and inhibits activation of a mammalian G protein-coupled receptor, which comprises separately contacting cells producing a second messenger response, expressing the DNA encoding the mammalian G protein-coupled receptor, and expressing the DNA encoding a chimeric G protein, wherein such cells do not normally express the DNA encoding the chimeric G protein, with both the chemical compound and a second chemical compound known to activate the mammalian G protein-coupled receptor, and with only the second chemical compound, under conditions suitable for activation of the mammalian G protein-coupled receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian G protein-coupled receptor.

The invention further provides a process of screening a plurality of chemical compounds not known to activate a mammalian G protein-coupled receptor to identify a compound which activates the mammalian G protein-coupled receptor which comprises:

(a) contacting cells transfected with and expressing DNA encoding a chimeric G protein and expressing DNA encoding a mammalian G protein-coupled receptor with the plurality of compounds not known to activate the mammalian G protein-coupled receptor, under conditions permitting activation of the mammalian G protein-coupled receptor;

(b) determining whether the activity of the mammalian G protein-coupled receptor is increased in the presence of one or more of the compounds; and if so (c) separately determining whether the activation of the mammalian G protein-coupled receptor is increased by any compound included in the plurality of compounds, so as to thereby identify each compound which activates the mammalian G protein-coupled receptor.

The invention still further provides a process of screening a plurality of chemical compounds not known to inhibit the activation of a mammalian G protein-coupled receptor to identify a compound which inhibits the activation of the mammalian G protein-coupled receptor, which comprises:

(a) contacting cells transfected with and expressing DNA encoding a chimeric G protein and expressing DNA encoding a mammalian G protein-coupled receptor with the plurality of compounds in the presence of a known mammalian G protein-coupled receptor agonist, under conditions permitting activation of the mammalian G protein-coupled receptor;

(b) determining whether the extent or amount of activation of the mammalian G protein-coupled receptor is reduced in the presence of one or more of the compounds, relative to the extent or amount of activation of the mammalian G protein-coupled receptor in the absence of such one or more compounds; and if so (c) separately determining whether each such compound inhibits activation of the mammalian G protein-coupled receptor for each compound included in the plurality of compounds, so as to thereby identify any compound included in such plurality of compounds which inhibits the activation of the mammalian G protein-coupled receptor.

The invention also provides a process for determining whether a chemical compound is a mammalian G protein-coupled receptor agonist, which comprises separately contacting membrane preparations from cells transfected with and expressing DNA encoding a chimeric G protein and expressing DNA encoding a mammalian G protein-coupled receptor with both the compound and [$^{35}$S]GTPγS, and with only [$^{35}$S]GTPγS, under conditions permitting the activation of the mammalian G protein-coupled receptor, and detecting [$^{35}$S]GTPγS binding to the membrane preparation and an increase in [$^{35}$S]GTPγS binding in the presence of the compound indicating that the chemical compound activates the mammalian G protein-coupled receptor.

In addition, the invention provides a process for determining whether a chemical compound is a mammalian G protein-coupled receptor antagonist which comprises separately contacting membrane preparations from cells transfected with and expressing DNA encoding a chimeric G protein and expressing DNA encoding a mammalian G protein-coupled receptor with the chemical compound, [$^{35}$S]GTPγS, and a second chemical compound known to activate the mammalian G protein-coupled receptor, with [$^{35}$S]GTPγS and only the second compound, and with [$^{35}$S]GTPγS alone, under conditions permitting the activation of the mammalian G protein-coupled receptor, detecting [$^{35}$S]GTPγS binding to each membrane preparation, comparing the increase in [$^{35}$S]GTPγS binding in the presence of the compound and the second compound relative to the binding of [$^{35}$S]GTPγS alone to the increase in [$^{35}$S]GTPγS binding in the presence of the second chemical compound relative to the binding of [$^{35}$S]GTPγS alone, and detecting a smaller increase in [$^{35}$S]GTPγS binding in the presence of the compound and the second compound indicating that the compound is a mammalian G protein-coupled receptor antagonist.

The invention further provides a process for determining whether a chemical compound is a mammalian G protein-coupled receptor agonist, which comprises contacting cells transfected with and expressing DNA encoding a chimeric G protein and expressing DNA encoding a mammalian G protein-coupled receptor with a compound, under conditions permitting the activation of the mammalian G protein-coupled receptor, and detecting changes in receptor active state conformation as manifested by changes in receptor/G protein heterotrimer association/dissociation in the presence of the compound indicating that the chemical compound activates the mammalian G protein-coupled receptor.

The inventions still further provides a process for determining whether a chemical compound is a mammalian G protein-coupled receptor antagonist which comprises separately contacting cells transfected with and expressing DNA encoding a chimeric G protein and expressing DNA encoding a mammalian G protein-coupled receptor with the chemical compound in the presence of a known mammalian G protein-coupled receptor agonist, under conditions permitting the activation of the mammalian G protein-coupled receptor, and detecting changes in receptor active state conformation as manifested by changes in receptor/G protein heterotrimer association/dissociation in the presence of the compound indicating that the compound is a mammalian G protein-coupled receptor antagonist.

The invention also provides a process for identifying a chemical compound which specifically binds to a mammalian G protein-coupled receptor which comprises contacting cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor.

The invention further provides a process for identifying a chemical compound which specifically binds to a mammalian G protein-coupled receptor which comprises contacting a membrane preparation from cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor.

In addition, the invention provides a process involving competitive binding for identifying a chemical compound which specifically binds to a mammalian G protein-coupled receptor which comprises separately contacting cells transfected with and expressing DNA encoding a chimeric G protein and expressing DNA encoding a mammalian G protein-coupled receptor, wherein such cells do not normally express the DNA encoding the chimeric G protein, with both the chemical compound and a second chemical compound known to bind to the mammalian G protein-coupled receptor, and with only the second chemical compound, under conditions suitable for binding of both compounds, and detecting specific binding of the chemical compound to the mammalian G protein-coupled receptor, a decrease in the binding of the second chemical compound to the mammalian G protein-coupled receptor in the presence of the chemical compound indicating that the chemical compound binds to the mammalian G protein-coupled receptor.

The invention further provides a process involving competitive binding for identifying a chemical compound which specifically binds to a mammalian G protein-coupled receptor which comprises separately contacting a membrane preparation from cells transfected with and expressing DNA encoding a chimeric G protein and expressing DNA encoding a mammalian G protein-coupled receptor, wherein such cells do not normally express the DNA encoding the chimeric G protein, with both the chemical compound and a second chemical compound known to bind to the receptor, and with only the second chemical compound, under conditions suitable for binding of both compounds, and detecting specific binding of the chemical compound to the mammalian G protein-coupled receptor, a decrease in the binding of the second chemical compound to the mammalian G protein-coupled receptor in the presence of the chemical compound indicating that the chemical compound binds to the mammalian G protein-coupled receptor.

The invention also provides a process of screening a plurality of chemical compounds not known to bind to a mammalian G protein-coupled receptor to identify a compound which specifically binds to the mammalian G protein-coupled receptor, which comprises (a) contacting cells transfected with and expressing DNA encoding a chimeric G protein and expressing DNA encoding a mammalian G protein-coupled receptor with a compound known to bind specifically to the mammalian G protein-coupled receptor;

(b) contacting the cells of step (a) with the plurality of compounds not known to bind specifically to the mammalian G protein-coupled receptor, under conditions permitting binding of compounds known to bind to the mammalian G protein-coupled receptor;

(c) determining whether the binding of the compound known to bind to the mammalian G protein-coupled receptor is reduced in the presence of the plurality of compounds, relative to the binding of the compound in the absence of the plurality of compounds; and if so (d) separately determining the binding to the mammalian G protein-coupled receptor of each compound included in the plurality of compounds, so as to thereby identify any compound included therein which specifically binds to the mammalian G protein-coupled receptor.

The invention further provides a process of screening a plurality of chemical compounds not known to bind to a mammalian G protein-coupled receptor to identify a compound which specifically binds to the mammalian G protein-coupled receptor, which comprises (a) contacting a membrane preparation from cells transfected with and expressing DNA encoding a chimeric G protein and expressing DNA encoding a mammalian G protein-coupled receptor with the plurality of compounds not known to bind specifically to the mammalian G protein-coupled receptor under conditions permitting binding of compounds known to bind to the mammalian G protein-coupled receptor;

(b) determining whether the binding of a compound known to bind to the mammalian G protein-coupled receptor is reduced in the presence of the plurality of compounds, relative to the binding of the compound in the absence of the plurality of compounds; and if so (c) separately determining the binding to the mammalian G protein-coupled receptor of each compound included in the plurality of compounds, so as to thereby identify any compound included therein which specifically binds to the mammalian G protein-coupled receptor.

The invention also provides a process for determining whether a chemical compound is a ligand for a mammalian G protein-coupled receptor which comprises contacting cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound activates the mammalian G protein-coupled receptor and is a ligand for the mammalian. G protein-coupled receptor.

The invention further provides a process for determining whether a chemical compound is a ligand for a mammalian G protein-coupled receptor which comprises contacting a membrane preparation from cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound activates the mammalian G protein-coupled receptor and is a ligand for the mammalian G protein-coupled receptor.

The invention still further provides a process for determining whether a chemical compound is a ligand for a mammalian G protein-coupled receptor which comprises contacting cells producing a second messenger response, expressing the DNA encoding the mammalian G protein-coupled receptor, and expressing the DNA encoding a chimeric G protein, wherein such cells do not normally express the DNA encoding the chimeric G protein, with the chemical compound under conditions suitable for activation of the mammalian G protein-coupled receptor, and measuring the second messenger response in the presence and in the absence of the chemical compound, a change in the second messenger response in the presence of the chemical compound indicating that the compound activates the mammalian G protein-coupled receptor and is a ligand for the mammalian G protein-coupled receptor.

In addition, the invention provides a process of screening a plurality of chemical compounds not known to activate a mammalian G protein-coupled receptor to identify a ligand for the mammalian G protein-coupled receptor which comprises:
(a) contacting cells transfected with and expressing DNA encoding a chimeric G protein and expressing DNA encoding a mammalian G protein-coupled receptor with the plurality of compounds not known to activate the mammalian G protein-coupled receptor, under conditions permitting activation of the mammalian G protein-coupled receptor;
(b) determining whether the activity of the mammalian G protein-coupled receptor is increased in the presence of one or more of the compounds; and if so
(c) separately determining whether the activation of the mammalian G protein-coupled receptor is increased by any compound included in the plurality of compounds, so as to thereby identify each compound which activates the mammalian G protein-coupled receptor and is a ligand for the mammalian G protein-coupled receptor.

The invention also provides a process for determining whether a chemical compound is a ligand for a mammalian G protein-coupled receptor, which comprises separately contacting membrane preparations from cells transfected with and expressing DNA encoding a chimeric G protein and expressing DNA encoding a mammalian G protein-coupled receptor with both the compound and [$^{35}$S]GTP$\gamma$S, and with only [$^{35}$S] GTP$\gamma$S, under conditions permitting the activation of the mammalian G protein-coupled receptor, and detecting [$^{35}$S]GTP$\gamma$S binding to the membrane preparation and an increase in [$^{35}$S]GTP$\gamma$S binding in the presence of the compound indicating that the chemical compound activates the mammalian G protein-coupled receptor and is a ligand for the mammalian G protein-coupled receptor.

In addition, the invention provides a process for determining whether a chemical compound is a ligand for the mammalian G protein-coupled receptor, which comprises contacting cells transfected with and expressing DNA encoding a chimeric G protein and expressing DNA encoding a mammalian G protein-coupled receptor with a compound, under conditions permitting the activation of the mammalian G protein-coupled receptor, and detecting changes in receptor active state conformation as manifested by changes in receptor/G protein heterotrimer association/dissociation in the presence of the compound indicating that the chemical compound activates the mammalian G protein-coupled receptor and is a ligand for the mammalian G protein-coupled receptor.

The invention further provides a process for identifying a ligand for a mammalian G protein-coupled receptor which comprises contacting cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor, indicating that the compound is a ligand for the mammalian G protein-coupled receptor.

The invention still further provides a process for identifying a chemical compound which specifically binds to a mammalian G protein-coupled receptor which comprises contacting a membrane preparation from cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor, indicating that the compound is a ligand for the mammalian G protein-coupled receptor.

The invention also provides a process of screening a plurality of independent clones not known to include a clone encoding a mammalian G protein-coupled receptor, to identify and isolate a clone encoding a mammalian G protein-coupled receptor, which comprises:
(a) contacting cells transfected with and expressing DNA encoding a chimeric G protein and expressing DNA encoding a plurality of independent clones with a ligand, under conditions permitting activation of a mammalian G protein-coupled receptor;
(b) determining whether the ligand activates the cells expressing the plurality of independent clones and the chimeric G protein; and if so
(c) isolating the single clone which expresses the mammalian G protein-coupled receptor activated by the ligand, so as to thereby identify any clone included in the plurality of clones as encoding a mammalian G protein-coupled receptor.

The invention further provides a process of screening a plurality of independent clones not known to include a clone encoding a mammalian G protein-coupled receptor, to identify and isolate a clone encoding a mammalian G protein-coupled receptor, which comprises:
(a) contacting cells transfected with and expressing DNA encoding a chimeric G protein and expressing DNA encoding a plurality of independent clones with a ligand, under conditions permitting specific binding to a mammalian G protein-coupled receptor;
(b) determining whether the ligand specifically binds to the cells expressing the plurality of independent clones and the chimeric G protein; and if so
(c) isolating the single clone which expresses the mammalian G protein-coupled receptor which specifically binds to the ligand, so as to thereby identify any clone included in the plurality of clones as encoding a mammalian G protein-coupled receptor.

Figure 1:
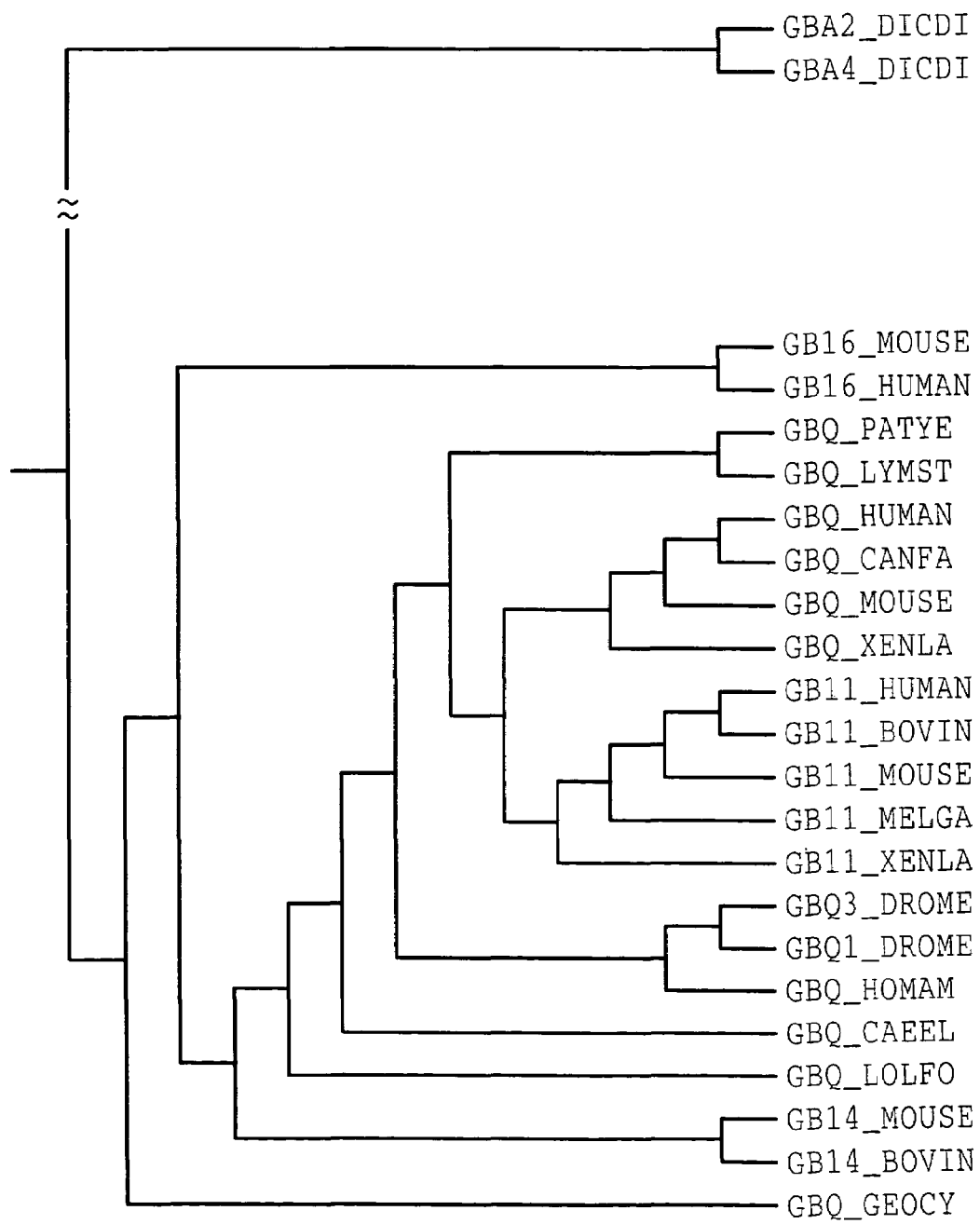
FIG. 1

Phylogenetic tree of the $G\alpha_q$ family of G proteins. The tree was created using the "Growtree" algorithm and specifying the "Cladogram" output (SeqLab version 10, Genetics Computer Group). Initially, a cladogram was created from a multiple sequence alignment ("Pileup" utility in SeqLab version 10, Genetics Computer Group) of all publicly available G protein sequences. The tree was then edited for clarity by removing non-$G\alpha_q$ sequences. Double tilde indicates a break in the branch to *Dictyostelium discoideum* sequences imposed to permit page formatting. Branch lengths are proportional to the number of accumulated amino acid substitutions.

GBA2_DICDI is *Dictyostelium discoideum* $G\alpha_2$ (Genbank Accession number P16051); GBA4_DICDI is *Dictyostelium discoideum* $G\alpha_4$ (Genbank Accession number P34042); GB16_MOUSE is *Mus musculus* (mouse) $G\alpha_{16}$ (Genbank Accession number G193571); GB16_HUMAN is *Homo sapiens* (human) $G\alpha_{16}$ (Genbank Accession number G182892) GBQ_PATYE is *Patinopecten yessoensis* Gαq (GenBank Accession number 015975); GBQ_LYMST is *Lymnaea stagnalis* $G\alpha_q$ (GenBank Accession number P38411); GBQ_HUMAN is *Homo sapiens* (human) $G\alpha_q$ (Genbank Accession number L76256); GBQ_CANFA is *Canis familiarus* $G\alpha_q$ (Genbank Accession number Q28294); GBQ_MOUSE is *Mus musculus* (mouse) $G\alpha_q$ (Genbank Accession number P21279); GBQ_XENLA is *Xenopus laevis* $G\alpha_q$ (Genbank Accession number P38410); GB11_HUMAN is *Homo sapiens* (human) $G\alpha_{11}$ (Genbank Accession number 29992); GB11_BOVIN is *Bos taurus* (bovine) $G\alpha_{11}$ (Genbank Accession number P38409); GB11_MOUSE is *Mus musculus* (mouse) $G\alpha_{11}$ (Genbank Accession number P21278); GB11_MELGA is *Meleagris gallopavo* $G\alpha_{11}$ (Genbank Accession number P45645); GB11_XENLA is *Xenopus laevis* $G\alpha_{11}$ (Genbank Accession number P43444); GBQ3_DROME is *Drosophila melanogaster* $G\alpha_{q3}$ (GenBank Accession number P54400); GBQ1_DROME is *Drosophila melanogaster* $G\alpha_{q1}$ (GenBank Accession number P23625); GBQ_HOMAM is *Homarus americanus* $G\alpha_q$ (GenBank Accession number P91950); GBQ_CAEEL is *Caenorhabditis elegans* $G\alpha_q$ (GenBank Accession number AF003739); GBQ_LOLFO is *Loligo forbesi* $G\alpha_q$ (GenBank Accession number P38412); GB14_MOUSE is *Mus musculus* (mouse) $G\alpha_{14}$ (Genbank Accession number P30677); GB14_BOVIN is *Bos taurus* (bovine) $G\alpha_{14}$ (Genbank Accession number P38408); and GBQ_GEOCY is *Geodia cydonium* $G\alpha_q$ (GenBank Accession number γ14248).

FIGS. 2A–2B

Amino acid sequences of $G\alpha_{q/x}$ chimeras. (*C. elegans* $G\alpha_{q/z5}$ (SEQ ID NO: 1); *C. elegans* $G\alpha_{q/z9}$ (SEQ ID NO: 2); *C. elegans* $G\alpha_{q/s9}$ (SEQ ID NO: 3); *C. elegans* $G\alpha_{q/s21}$ (SEQ ID NO: 4); *C. elegans* $G\alpha_{q/i3(5)}$ (SEQ ID NO: 5); and *D. melanogaster* $G\alpha_{q/z5}$ (SEQ ID NO: 41)). Bold regions at the C-terminus denote where amino acid substitutions are made between *C. elegans* $G\alpha_q$ and mammalian $G\alpha_z$, $G\alpha_s$, or $G\alpha_{i3}$. The remainder of the protein (non-bold amino acids) in each case is *C. elegans* or *D. melanogaster* $G\alpha_q$.

FIG. 3

Examples of receptor-evoked responses in oocytes expressing $cG\alpha_{q/z5}$ or $hG\alpha_{q/z5}$ chimeric G proteins.

FIG. 4

Examples of receptor-evoked responses in mammalian cells expressing $cG\alpha_{q/z5}$ or $hG\alpha_{q/z5}$ chimeric G proteins plus the human D1 receptor. Transiently transfected COS-7 cells were seeded into a 96-well microtiter plate and monitored for calcium mobilization in the FLIPR™ using the calcium-sensitive dye Fluo-3. A) Representative time course of fluorescence in cells stimulated at time=10 seconds with 100 μM dopamine. Each curve is derived from a representative well. B) Maximal change in relative fluorescent units was calculated for dopamine concentrations ranging from 0.3 nM to 100 μM. Triplicate determinations, plotted as mean±standard error of the mean, were used to construct concentration-response curves. In the example shown here, a measurable response to dopamine was obtained only in the presence of $cG\alpha_{q/z5}$, with a maximal signal of 14,723 fluorescence units and $pEC_{50}$ of 6.32. Average maximal responses from multiple experiments (n≧2) are listed in Table 5.

FIGS. 5A–5C

Multiple sequence alignment of $G\alpha_q$ proteins from invertebrate and vertebrate organisms. Sequences were aligned using "Pileup" (SeqLab version 10, Genetics Computer Group). The degree of amino acid identity is indicated by the level of shading (black, 100% identity, white <60%).

GBQ_HUMAN is *Homo sapiens* (human) $G\alpha_q$ (Genbank Accession number L76256; SEQ ID NO: 6); GBQ_CANFA is *Canis familiarus* $G\alpha_q$ (Genbank Accession number Q28294; SEQ ID NO: 7); GBQ_MOUSE is *Mus musculus* (mouse) $G\alpha_q$ (Genbank Accession number P21279; SEQ ID NO: 8); GBQ_XENLA is *Xenopus laevis* $G\alpha_q$ (Genbank Accession number P38410; SEQ ID NO: 9); GBQ_PATYE is *Patinopecten yessoensis* $G\alpha_q$ (GenBank Accession number 015975; SEQ ID NO: 10); GBQ_LYMST is *Lymnaea stagnalis* $G\alpha_q$ (GenBank Accession number P38411; SEQ ID NO: 11); GBQ1_DROME is *Drosophila melanogaster* $G\alpha_{q1}$ (GenBank Accession number P23625; SEQ ID NO: 12); GBQ3_DROME is *Drosophila melanogaster* $G\alpha_{q3}$ (GenBank Accession number P54400; SEQ ID NO: 13); GBQ_HOMAM is *Homarus americanus* $G\alpha_q$ (GenBank Accession number P91950; SEQ ID NO: 14); GBQ_LIMPO is *Limulus polyphemus* $G\alpha_q$ (GenBank Accession number g1857923; SEQ ID NO: 15); GBQ_LOLFO is *Loligo forbesi* $G\alpha_q$ (GenBank Accession number P38412; SEQ ID NO: 16); GBQ_CAEEL is *Caenorhabditis elegans* $G\alpha_q$ (GenBank Accession number AF003739; SEQ ID NO: 17); GBQ_GEOCY is *Geodia cydonium* $G\alpha_q$ (GenBank Accession number 14248; SEQ ID NO: 18).

DETAILED DESCRIPTION OF THE INVENTION

The following definitions are presented as an aid in understanding this invention.

For the purposes of this invention, "ligand" is a molecule capable of binding to and modulating a receptor. The ligand may be chemically synthesized or may occur in nature.

For the purposes of this invention, "agonist" is a ligand capable of stimulating the biological activity of a receptor.

For the purposes of this invention, "antagonist" is a ligand capable of inhibiting the biological activity of a receptor.

For the purposes of this invention, "invertebrate" species are defined as those members of the Animal Kingdom that do not possess a vertebral column or backbone (Barnes, 1974).

For the purposes of this invention, in one embodiment, an invertebrate Gαq G protein has amino acids QK at positions 12 and 13 from the N-terminus and does not contain the sequence MTLESI (SEQ ID NO: 36) at the N-terminus.

For the purposes of this invention, "vertebrate" species are those members of the Animal Kingdom that do possess a vertebral column or backbone (Barnes, 1974). A common characteristic of vertebrate Gαq G proteins is an N-terminal extension composed of the amino acids MTLESI (SEQ ID NO: 36).

For the purposes of this invention, "Gαq second messenger response" is one of a number of responses which are typically produced by activation of G protein heterotrimers containing Gαq.

For the purposes of this invention, "Gαs second messenger response" is one of a number of responses which are typically produced by activation of G protein heterotrimers containing Gαs.

For the purposes of this invention, "receptor/G protein heterotrimer association/dissociation" means a change in the intermolecular relationship between either α-β-γ subunits themselves or one or more of these subunits with the receptor.

Having due regard to the preceding definitions, the present invention provides an isolated nucleic acid encoding a chimeric G protein, wherein the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted or varies therefrom by no more than five amino acids, provided that at least five of the C-terminal amino acids of the chimeric G protein are present at the C-terminus of such vertebrate G protein.

In one embodiment, the nucleic acid encodes a chimeric G protein, wherein the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted or varies therefrom by no more than two amino acids, provided that at least five of the C-terminal amino acids of the chimeric G protein are present at the C-terminus of such vertebrate G protein.

In another embodiment, the nucleic acid encodes a chimeric G protein, wherein the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted.

In one embodiment, the nucleic acid is DNA. In one embodiment, the DNA is cDNA. In another embodiment, the DNA is genomic DNA. In another embodiment, the nucleic acid is RNA.

In one embodiment, the aforementioned vertebrate G protein is a mammalian G protein. In another embodiment, the aforementioned contiguous amino acids which have been deleted are contained in FVFAAVKDTILQHNLKEYNLV* (SEQ ID NO: 37), wherein V* is the C-terminal amino acid.

In another embodiment, the vertebrate G protein is a vertebrate Gαz G protein. In another embodiment, the number of contiguous amino acids which have replaced the deleted amino acids are contained in FVFDAVTDVI-IQNNLKYIGLC* (SEQ ID NO: 38), wherein C* is the C-terminal amino acid. In another embodiment, the aforementioned invertebrate Gαq G protein has five contiguous amino acids beginning with the C-terminal amino acid which have been deleted and replaced by five contiguous amino acids beginning with the C-terminal amino acid of the vertebrate Gαz protein.

In another embodiment, the vertebrate G protein is a vertebrate Gαs G protein. In another embodiment, the number of contiguous amino acids which have replaced the deleted amino acids are contained in RVFNDCRDIIQRM-HLRQYELL* (SEQ ID NO: 39), wherein L* is the C-terminal amino acid. In another embodiment, the invertebrate Gαq G protein has nine contiguous amino acids beginning with the C-terminal amino acid which have been deleted and replaced by nine contiguous amino acids beginning with the C-terminal amino acid of the vertebrate Gαs protein.

In another embodiment, the vertebrate G protein is a vertebrate Gαi3 G protein. In another embodiment, the number of contiguous amino acids which have replaced the deleted amino acids are contained in FVFDAVTDVI-IKNNLKECGLY* (SEQ ID NO: 40), wherein Y* is the C-terminal amino acid. In another embodiment, the invertebrate Gαq G protein has five contiguous amino acids beginning with the C-terminal amino acid which have been deleted and replaced by five contiguous amino acids beginning with the C-terminal amino acid of the vertebrate Gαi3 protein.

In other embodiments, the vertebrate G protein is a vertebrate Gαi1 G protein, a vertebrate Gαi2 G protein, a vertebrate GαoA G protein, or a vertebrate GαoB G protein.

In another embodiment, the invertebrate Gαq G protein is a *Caenorhabditis elegans* Gαq G protein. In still other embodiments, the invertebrate Gαq G protein is a *Drosophila melanogaster* Gαq G protein, a *Limulus polyphemus* Gαq G protein, a *Patinopecten yessoensis* Gαq G protein, a *Loligo forbesi* Gαq G protein, a *Homarus americanus* Gαq G protein, a *Lymnaea stagnalis* Gαq G protein, a *Geodia cydonium* Gαq G protein, or a *Dictyostelium discoideum* Gα$_4$ G protein.

In other embodiments, the chimeric G protein has an amino acid sequence substantially the same as the amino acid sequence shown in (a) FIG. 2, *C. elegans* Gα$_{q/z5}$ (SEQ ID NO: 1); (b) FIG. 2, *C. elegans* Gα$_{q/z9}$ (SEQ ID NO: 2); (c) FIG. 2, *C. elegans* Gα$_{q/s9}$ (SEQ ID NO: 3); (d) FIG. 2, *C. elegans* Gα$_{q/s21}$ (SEQ ID NO: 4); (e) FIG. 2, *C. elegans* Gα$_{q/i3(5)}$ (SEQ ID NO: 5); or (f) FIG. 2, *D. melanogaster* Gα$_{q/zs}$ (SEQ ID NO: 41).

The invention provides a vector comprising any of the aforementioned nucleic acids. In different embodiments, the vector is adapted for expression in a cell which comprises the regulatory elements necessary for expression of the nucleic acid in the cell operatively linked to the nucleic acid encoding the chimeric G protein so as to permit expression thereof, wherein the cell is a bacterial, amphibian, yeast, insect, or mammalian cell. In different embodiments, the vector is a plasmid, a baculovirus, or a retrovirus.

The invention provides a cell comprising any of the aforementioned vectors, wherein the cell comprises DNA encoding a mammalian G protein-coupled receptor. In one embodiment of the cell, the DNA encoding the mammalian G protein-coupled receptor is endogenous to the cell. In another embodiment, the DNA encoding the mammalian G protein-coupled receptor is transfected into the cell. In one embodiment, the cell is a non-mammalian cell. In different embodiments, the non-mammalian cell is a *Xenopus* oocyte cell or a *Xenopus* melanophore cell. In another embodiment, the cell is a mammalian cell. In different embodiments, the mammalian cell is a COS-7 cell, a 293 human embryonic kidney cell, a NIH-3T3 cell, a LM(tk−) cell, a mouse Y1 cell, or a CHO cell. In one embodiment, the cell is an insect cell. In different embodiments, the insect cell is an Sf9 cell, an Sf21 cell or a *Trichoplusia* ni 5B-4 cell. The invention provides a membrane preparation isolated from any of the aforementioned cells.

The invention also provides a process for determining whether a chemical compound is a mammalian G protein-coupled receptor agonist which comprises contacting cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound is a mammalian G protein-coupled receptor agonist.

The invention further provides a process for determining whether a chemical compound is a mammalian G protein-coupled receptor agonist which comprises contacting a membrane preparation from cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound is a mammalian G protein-coupled receptor agonist.

The invention also provides a process for determining whether a chemical compound is a mammalian G protein-coupled receptor antagonist which comprises contacting cells transfected with and expressing DNA encoding a chimeric G protein and expressing DNA encoding a mammalian G protein-coupled receptor, with the compound in the presence of a known mammalian G protein-coupled receptor agonist, under conditions permitting the activation of the mammalian G protein-coupled receptor, and detecting a decrease in mammalian G protein-coupled receptor activity, so as to thereby determine whether the compound is a mammalian G protein-coupled receptor antagonist.

The invention further provides a process for determining whether a chemical compound is a mammalian G protein-coupled receptor antagonist which comprises contacting a membrane preparation from cells transfected with and expressing DNA encoding a chimeric G protein and expressing DNA encoding a mammalian G protein-coupled receptor, with the compound in the presence of a known mammalian G protein-coupled receptor agonist, under conditions permitting the activation of the mammalian G protein-coupled receptor, and detecting a decrease in mammalian G protein-coupled receptor activity, so as to thereby determine whether the compound is a mammalian G protein-coupled receptor antagonist.

In one embodiment of any of the aforementioned processes, the DNA encoding the mammalian G protein-coupled receptor is endogenous to the cell. In another embodiment, the DNA encoding the mammalian G protein-coupled receptor is transfected into the cell. In different embodiments, the mammalian G protein-coupled receptor is a human Y5 receptor, a human GALR2 receptor, a human kappa opioid receptor, a human NPFF1 receptor, a human NPFF2 receptor, a human α2A adrenergic receptor, a human dopamine D2 receptor, a human GALR1 receptor, a human Y2 receptor, a human Y1 receptor, a human Y4 receptor, a human α1A adrenergic receptor, a human dopamine D1 receptor, or a rat NTR1 receptor.

The invention also provides a process for determining whether a chemical compound specifically binds to and activates a mammalian G protein-coupled receptor, which comprises contacting cells producing a second messenger response, expressing the DNA encoding the mammalian G protein-coupled receptor, and expressing the DNA encoding a chimeric G protein, wherein such cells do not normally express the DNA encoding the chimeric G protein, with the chemical compound under conditions suitable for activation of the mammalian G protein-coupled receptor, and measuring the second messenger response in the presence and in the absence of the chemical compound, a change in the second messenger response in the presence of the chemical compound indicating that the compound activates the mammalian G protein-coupled receptor. In one embodiment of the process, the DNA encoding the mammalian G protein-coupled receptor is endogenous to the cell. In another embodiment, DNA encoding the mammalian G protein-coupled receptor is transfected into the cell.

In one embodiment of the aforementioned process, the second messenger response is the detection of a reporter protein under the transcriptional control of a promoter element. In another embodiment, the second messenger response is measured by a change in cell proliferation. In another embodiment, the second messenger response is a Gαq second messenger response. In one embodiment, the Gαq second messenger response comprises release of inositol phosphate and the change in second messenger is an increase in the level of inositol phosphate. In another embodiment, the Gαq second messenger response comprises release of arachidonic acid and the change in second messenger is an increase in the level of arachidonic acid. In another embodiment, the Gαq second messenger response comprises activation of MAP kinase and the change in second messenger response is an increase in MAP kinase activation. In another embodiment, the Gαq second messenger response comprises intracellular calcium levels and the change in second messenger is an increase in the measure of intracellular calcium. In one embodiment, the measure of intracellular calcium levels is made by chloride current readings. In other embodiments, the measure of intracellular calcium is made by fluorescence readings, luminescence readings, electrophysiological readings, or through the detection of a reporter protein under the transcriptional control of a calcium-responsive promoter element.

In addition, the invention provides a process for determining whether a chemical compound specifically binds to and inhibits activation of a mammalian G protein-coupled receptor, which comprises separately contacting cells producing a second messenger response, expressing the DNA encoding the mammalian G protein-coupled receptor, and expressing the DNA encoding a chimeric G protein, wherein such cells do not normally express the DNA encoding the chimeric G protein, with both the chemical compound and a second chemical compound known to activate the mammalian G protein-coupled receptor, and with only the second chemical compound, under conditions suitable for activation of the mammalian G protein-coupled receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the mammalian G protein-coupled receptor. In one embodiment of the process, the DNA encoding the mammalian G protein-coupled receptor is endogenous to the cell. In another embodiment, DNA encoding the mammalian G protein-coupled receptor is transfected into the cell.

In one embodiment of the aforementioned process, the second messenger response is the detection of a reporter protein under the transcriptional control of a promoter element. In another embodiment, the second messenger response is measured by a change in cell proliferation. In another embodiment, the second messenger response is a Gαq second messenger response. In one embodiment, the Gαq second messenger response comprises release of inositol phosphate and the change in second messenger response is a smaller increase in the level of inositol phosphate in the presence of both the chemical compound and the second chemical compound than in the presence of only the second chemical compound. In another embodiment, the Gαq second messenger response comprises activation of MAP kinase and the change in second messenger response is a smaller increase in the level of MAP kinase activation in the presence of both the chemical compound and the second chemical compound than in the presence of only the second chemical compound. In another embodiment, the Gαq second messenger response comprises release of arachidonic acid and the change in second messenger response is an increase in the level of arachidonic acid levels in the presence of both the chemical compound and the second chemical compound than in the presence of only the second chemical compound. In another embodiment, the Gαq second messenger response comprises change in intracellular calcium levels and the change in second messenger response is a smaller increase in the measure of intracellular calcium in the presence of both the chemical compound and the second chemical compound than in the presence of only the second chemical compound. In one embodiment, the measure of intracellular calcium levels is made by chloride current readings. In other embodiments, the measure of intracellular calcium is made by fluorescence readings, luminescence readings, electrophysiological readings, or through the detection of a reporter protein under the transcriptional control of a calcium-responsive promoter element.

The invention also provides a process of screening a plurality of chemical compounds not known to activate a mammalian G protein-coupled receptor to identify a compound which activates the mammalian G protein-coupled receptor which comprises:
(a) contacting cells transfected with and expressing DNA encoding a chimeric G protein and expressing DNA encoding a mammalian G protein-coupled receptor with the plurality of compounds not known to activate the mammalian G protein-coupled receptor, under conditions permitting activation of the mammalian G protein-coupled receptor;
(b) determining whether the activity of the mammalian G protein-coupled receptor is increased in the presence of one or more of the compounds; and if so
(c) separately determining whether the activation of the mammalian G protein-coupled receptor is increased by any compound included in the plurality of compounds, so as to thereby identify each compound which activates the mammalian G protein-coupled receptor.

The invention further provides a process of screening a plurality of chemical compounds not known to inhibit the activation of a mammalian G protein-coupled receptor to identify a compound which inhibits the activation of the mammalian G protein-coupled receptor, which comprises:
(a) contacting cells transfected with and expressing DNA encoding a chimeric G protein and expressing DNA encoding a mammalian G protein-coupled receptor with the plurality of compounds in the presence of a known mammalian G protein-coupled receptor agonist, under conditions permitting activation of the mammalian G protein-coupled receptor;
(b) determining whether the extent or amount of activation of the mammalian G protein-coupled receptor is reduced in the presence of one or more of the compounds, relative to the extent or amount of activation of the mammalian G protein-coupled receptor in the absence of such one or more compounds; and if so
(c) separately determining whether each such compound inhibits activation of the mammalian G protein-coupled receptor for each compound included in the plurality of compounds, so as to thereby identify any compound included in such plurality of compounds which inhibits the activation of the mammalian G protein-coupled receptor.

In one embodiment of the aforementioned processes, the DNA encoding the mammalian G protein-coupled receptor is endogenous to the cell. In another embodiment, the DNA encoding the mammalian G protein-coupled receptor is transfected into the cell.

The invention also provides a process for determining whether a chemical compound is a mammalian G protein-coupled receptor agonist, which comprises separately contacting membrane preparations from cells transfected with and expressing DNA encoding a chimeric G protein and expressing DNA encoding a mammalian G protein-coupled receptor with both the compound and [$^{35}$S]GTPγS, and with only [$^{35}$S]GTPγS, under conditions permitting the activation of the mammalian G protein-coupled receptor, and detecting [$^{35}$S]GTPγS binding to the membrane preparation and an increase in [$^{35}$S]GTPγS binding in the presence of the compound indicating that the chemical compound activates the mammalian G protein-coupled receptor.

The invention further provides a process for determining whether a chemical compound is a mammalian G protein-coupled receptor antagonist which comprises separately contacting membrane preparations from cells transfected with and expressing DNA encoding a chimeric G protein and expressing DNA encoding a mammalian G protein-coupled receptor with the chemical compound, [$^{35}$S]GTPγS, and a second chemical compound known to activate the mammalian G protein-coupled receptor, with [$^{35}$S]GTPγS and only the second compound, and with [$^{35}$S]GTPγS alone, under conditions permitting the activation of the mammalian G protein-coupled receptor, detecting [$^{35}$S]GTPγS binding to each membrane preparation, comparing the increase in [$^{35}$S]GTPγS binding in the presence of the compound and the second compound relative to the binding of [$^{35}$S]GTPγS alone to the increase in [$^{35}$S]GTPγS binding in the presence of the second chemical compound relative to the binding of [$^{35}$S]GTPγS alone, and detecting a smaller increase in [$^{35}$S]GTPγS binding in the presence of the compound and the second compound indicating that the compound is a mammalian G protein-coupled receptor antagonist.

In one embodiment of the aforementioned processes, the DNA encoding the mammalian G protein-coupled receptor is endogenous to the cell. In another embodiment, the DNA encoding the mammalian G protein-coupled receptor is transfected into the cell. In one embodiment, the mammalian G protein-coupled receptor produces a Gαs second messenger response in the absence of the chimeric G protein.

This invention also provides a process for determining whether a chemical compound is a mammalian G protein-coupled receptor agonist, which comprises contacting cells transfected with and expressing DNA encoding a chimeric G protein and expressing DNA encoding a mammalian G protein-coupled receptor with a compound, under conditions permitting the activation of the mammalian G protein-coupled receptor, and detecting changes in receptor active state conformation as manifested by changes in receptor/G protein heterotrimer association/dissociation in the presence of the compound indicating that the chemical compound activates the mammalian G protein-coupled receptor.

This invention further provides a process for determining whether a chemical compound is a mammalian G protein-coupled receptor antagonist which comprises separately contacting cells transfected with and expressing DNA encoding a chimeric G protein and expressing DNA encoding a mammalian G protein-coupled receptor with the chemical compound in the presence of a known mammalian G protein-coupled receptor agonist, under conditions permitting the activation of the mammalian G protein-coupled receptor, and detecting changes in receptor active state conformation as manifested by changes in receptor/G protein heterotrimer association/dissociation in the presence of the compound indicating that the compound is a mammalian G protein-coupled receptor antagonist.

In one embodiment of the aforementioned processes, the DNA encoding the mammalian G protein-coupled receptor is endogenous to the cell. In another embodiment, the DNA encoding the mammalian G protein-coupled receptor is transfected into the cell.

In one embodiment of any of the aforementioned processes, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαz protein beginning with the C-terminal amino acid of such vertebrate Gαz protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαs protein beginning with the C-terminal amino acid of such vertebrate Gαs protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαi3 protein beginning with the C-terminal amino acid of such vertebrate Gαi3 protein, wherein such number equals the number of amino acids deleted.

In another embodiment, the chimeric G protein comprises a *Caenorhabditis elegans* Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In other embodiments, the chimeric G protein comprises a *Drosophila melanogaster* Gαq G protein, a *Limulus polyphemus* Gαq G protein, a *Patinopecten yessoensis* Gαq G protein, a *Loligo forbesi* Gαq G protein, a *Homarus americanus* Gαq G protein, a *Lymnaea stagnalis* Gαq G protein, a *Geodia cydonium* Gαq G protein, or a *Dictyostelium discoideum* Gα4 G protein, from which at least five, but not more than twenty-one, contiguous amino acids beginning with the C-terminal amino acid have been deleted and replaced by a number of contiguous amino acids present in a vertebrate G protein beginning with the C-terminal amino acid of a vertebrate G protein, wherein such number equals the number of amino acids deleted. In other embodiments, the chimeric G protein has an amino acid sequence substantially the same as the amino acid sequence shown in (a) FIG. 2, *C. elegans* Gα$_{q/z5}$ (SEQ ID NO: 1); (b) FIG. 2, *C. elegans* Gα$_{q/z9}$ (SEQ ID NO: 2); (c) FIG. 2, *C. elegans* Gα$_{q/s9}$ (SEQ ID NO: 3); (d) FIG. 2, *C. elegans* Gα$_{q/s21}$ (SEQ ID NO: 4); (e) FIG. 2, *C. elegans* Gα$_{q/i3(5)}$ (SEQ ID NO: 5); or (f) FIG. 2, *D. melanogaster* Gα$_{q/zs}$ (SEQ ID NO: 41).

In one embodiment of any of the aforementioned processes, the cell is an insect cell. In another embodiment, the cell is a mammalian cell. In one embodiment, the mammalian cell is nonneuronal in origin. In further embodiments, the nonneuronal cell is a COS-7 cell, 293 human embryonic kidney cell, a CHO cell, a NIH-3T3 cell, a mouse Y1 cell, or a LM(tk−) cell.

The invention also provides a process for identifying a chemical compound which specifically binds to a mammalian G protein-coupled receptor which comprises contacting cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor.

The invention further provides a process for identifying a chemical compound which specifically binds to a mammalian G protein-coupled receptor which comprises contacting a membrane preparation from cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor.

In addition, the invention provides a process involving competitive binding for identifying a chemical compound which specifically binds to a mammalian G protein-coupled receptor which comprises separately contacting cells transfected with and expressing DNA encoding a chimeric G protein and expressing DNA encoding a mammalian G protein-coupled receptor, wherein such cells do not normally express the DNA encoding the chimeric G protein, with both the chemical compound and a second chemical compound known to bind to the mammalian G protein-coupled receptor, and with only the second chemical compound, under conditions suitable for binding of both compounds, and detecting specific binding of the chemical compound to the mammalian G protein-coupled receptor, a decrease in the binding of the second chemical compound to the mammalian G protein-coupled receptor in the presence of the chemical compound indicating that the chemical compound binds to the mammalian G protein-coupled receptor.

The invention further provides a process involving competitive binding for identifying a chemical compound which specifically binds to a mammalian G protein-coupled receptor which comprises separately contacting a membrane preparation from cells transfected with and expressing DNA encoding a chimeric G protein and expressing DNA encoding a mammalian G protein-coupled receptor, wherein such cells do not normally express the DNA encoding the chimeric G protein, with both the chemical compound and a second chemical compound known to bind to the receptor, and with only the second chemical compound, under conditions suitable for binding of both compounds, and detecting specific binding of the chemical compound to the mammalian G protein-coupled receptor, a decrease in the binding of the second chemical compound to the mammalian G protein-coupled receptor in the presence of the chemical compound indicating that the chemical compound binds to the mammalian G protein-coupled receptor.

The invention also provides a process of screening a plurality of chemical compounds not known to bind to a mammalian G protein-coupled receptor to identify a compound which specifically binds to the mammalian G protein-coupled receptor, which comprises (a) contacting cells transfected with and expressing DNA encoding a chimeric G protein and expressing DNA encoding a mammalian G protein-coupled receptor with a compound known to bind specifically to the mammalian G protein-coupled receptor;

(b) contacting the cells of step (a) with the plurality of compounds not known to bind specifically to the mammalian G protein-coupled receptor, under conditions permitting binding of compounds known to bind to the mammalian G protein-coupled receptor;

(c) determining whether the binding of the compound known to bind to the mammalian G protein-coupled receptor is reduced in the presence of the plurality of compounds, relative to the binding of the compound in the absence of the plurality of compounds; and if so (d) separately determining the binding to the mammalian G protein-coupled receptor of each compound included in the plurality of compounds, so as to thereby identify any compound included therein which specifically binds to the mammalian G protein-coupled receptor.

The invention further provides a process of screening a plurality of chemical compounds not known to bind to a mammalian G protein-coupled receptor to identify a compound which specifically binds to the mammalian G protein-coupled receptor, which comprises (a) contacting a membrane preparation from cells transfected with and expressing DNA encoding a chimeric G protein and expressing DNA encoding a mammalian G protein-coupled receptor with the plurality of compounds not known to bind specifically to the mammalian G protein-coupled receptor under conditions permitting binding of compounds known to bind to the mammalian G protein-coupled receptor;

(b) determining whether the binding of a compound known to bind to the mammalian G protein-coupled receptor is reduced in the presence of the plurality of compounds, relative to the binding of the compound in the absence of the plurality of compounds; and if so (c) separately determining the binding to the mammalian G protein-coupled receptor of each compound included in the plurality of compounds, so as to thereby identify any compound included therein which specifically binds to the mammalian G protein-coupled receptor.

In one embodiment of any of the aforementioned processes, the DNA encoding the mammalian G protein-coupled receptor is endogenous to the cell. In another embodiment, the DNA encoding the mammalian G protein-coupled receptor is transfected into the cell.

In one embodiment of any of the aforementioned processes, the chimeric G protein comprises an invertebrate G$\alpha$q G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In another embodiment, the chimeric G protein comprises an invertebrate G$\alpha$q G protein from which at least five, but not more than twenty-one, contiguous amino acids beginning with the C-terminal amino acid have been deleted and replaced by a number of contiguous amino acids present in a vertebrate G$\alpha$z protein beginning with the C-terminal amino acid of such vertebrate G$\alpha$z protein, wherein such number equals the number of amino acids deleted. In another embodiment, the chimeric G protein comprises an invertebrate G$\alpha$q G protein from which at least five, but not more than twenty-one, contiguous amino acids beginning with the C-terminal amino acid have been deleted and replaced by a number of contiguous amino acids present in a vertebrate G$\alpha$s protein beginning with the C-terminal amino acid of such vertebrate G$\alpha$s protein, wherein such number equals the number of amino acids deleted. In another embodiment, the chimeric G protein comprises an invertebrate G$\alpha$q G protein from which at least five, but not more than twenty-one, contiguous amino acids beginning with the C-terminal amino acid have been deleted and replaced by a number of contiguous amino acids present in a vertebrate G$\alpha$i3 protein beginning with the C-terminal amino acid of such vertebrate G$\alpha$i3 protein, wherein such number equals the number of amino acids deleted.

In another embodiment, the chimeric G protein comprises an *Caenorhabditis elegans* G$\alpha$q G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In other embodiments, the chimeric G protein comprises a *Drosophila melanogaster* G$\alpha$q G protein, a *Limulus polyphemus* G$\alpha$q G protein, a *Patinopecten yessoensis* G$\alpha$q G protein, a *Loligo forbesi* G$\alpha$q G protein, a *Homarus americanus* G$\alpha$q G protein, a *Lymnaea stagnalis* G$\alpha$q G protein, a *Geodia cydonium* G$\alpha$q G protein, or a *Dictyostelium discoideum* G$\alpha_4$ G protein, from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In other embodiments, the chimeric G protein has an amino acid sequence substantially the same as the amino acid sequence shown in (a) FIG. 2, *C. elegans* G$\alpha_{q/z5}$ (SEQ ID NO: 1); (b) FIG. 2, *C. elegans* G$\alpha_{q/z9}$ (SEQ ID NO: 2); (c) FIG. 2, *C. elegans* G$\alpha_{q/s9}$ (SEQ ID NO: 3); (d) FIG. 2, *C. elegans* G$\alpha_{q/s21}$ (SEQ ID NO: 4); (e) FIG. 2, *C. elegans* G$\alpha_{q/i3(5)}$ (SEQ ID NO: 5); or (f) FIG. 2, *D. melanogaster* G$\alpha_{q/zs}$ (SEQ ID NO: 41).

In one embodiment of any of the aforementioned processes, the cell is an insect cell. In another embodiment, the cell is a mammalian cell. In one embodiment, the mammalian cell is nonneuronal in origin. In further embodiments, the nonneuronal cell is a COS-7 cell, 293 human embryonic kidney cell, a CHO cell, a NIH-3T3 cell, a mouse Y1 cell, or a LM(tk−) cell.

The invention provides a process for determining whether a chemical compound is a ligand for a mammalian G protein-coupled receptor which comprises contacting cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound activates the mammalian G protein-coupled receptor and is a ligand for the mammalian G protein-coupled receptor.

The invention further provides a process for determining whether a chemical compound is a ligand for a mammalian G protein-coupled receptor which comprises contacting a membrane preparation from cells transfected with and expressing DNA encoding a chimeric G protein and expressing DNA encoding a mammalian G protein-coupled receptor, with the compound under conditions permitting the activation of the mammalian G protein-coupled receptor, and detecting an increase in mammalian G protein-coupled receptor activity, so as to thereby determine whether the compound activates the mammalian G protein-coupled receptor and is a ligand for the mammalian G protein-coupled receptor.

The invention also provides a process for determining whether a chemical compound is a ligand for a mammalian G protein-coupled receptor which comprises contacting cells producing a second messenger response, expressing the DNA encoding the mammalian G protein-coupled receptor, and expressing the DNA encoding a chimeric G protein, wherein such cells do not normally express the DNA encoding the chimeric G protein, with the chemical compound under conditions suitable for activation of the mammalian G protein-coupled receptor, and measuring the second messenger response in the presence and in the absence of the chemical compound, a change in the second messenger response in the presence of the chemical compound indicating that the compound activates the mammalian G protein-coupled receptor and is a ligand for the mammalian G protein-coupled receptor.

In one embodiment of the aforementioned process, the second messenger response is a G$\alpha$q second messenger response. In one embodiment, the G$\alpha$q second messenger response comprises intracellular calcium levels and the change in second messenger is an increase in the measure of intracellular calcium. In one embodiment, the measure of intracellular calcium levels is made by chloride current readings. In other embodiments, the measure of intracellular calcium is made by fluorescence readings, luminescence readings, electrophysiological readings, or through the detection of a reporter protein under the transcriptional control of a calcium-responsive promoter element.

In addition, the invention provides a process of screening a plurality of chemical compounds not known to activate a mammalian G protein-coupled receptor to identify a ligand for the mammalian G protein-coupled receptor which comprises:

(a) contacting cells transfected with and expressing DNA encoding a chimeric G protein and expressing DNA encoding a mammalian G protein-coupled receptor with the plurality of compounds not known to activate the mammalian G protein-coupled receptor, under conditions permitting activation of the mammalian G protein-coupled receptor;

(b) determining whether the activity of the mammalian G protein-coupled receptor is increased in the presence of one or more of the compounds; and if so (c) separately determining whether the activation of the mammalian G protein-coupled receptor is increased by any compound included in the plurality of compounds, so as to thereby identify each compound which activates the mammalian G protein-coupled receptor and is a ligand for the mammalian G protein-coupled receptor.

The invention also provides a process for determining whether a chemical compound is a ligand for a mammalian G protein-coupled receptor, which comprises separately contacting membrane preparations from cells transfected with and expressing DNA encoding a chimeric G protein and expressing DNA encoding a mammalian G protein-coupled receptor with both the compound and [$^{35}$S]GTP$\gamma$S, and with only [$^{35}$S]GTP$\gamma$S, under conditions permitting the activation of the mammalian G protein-coupled receptor, and detecting [$^{35}$S]GTP$\gamma$S binding to the membrane preparation and an increase in [$^{35}$S]GTP$\gamma$S binding in the presence of the compound indicating that the chemical compound activates the mammalian G protein-coupled receptor and is a ligand for the mammalian G protein-coupled receptor.

In addition, the invention provides a process for determining whether a chemical compound is a ligand for the mammalian G protein-coupled receptor, which comprises contacting cells transfected with and expressing DNA encoding a chimeric G protein and expressing DNA encoding a mammalian G protein-coupled receptor with a compound, under conditions permitting the activation of the mammalian G protein-coupled receptor, and detecting changes in receptor active state conformation as manifested by changes in receptor/G protein heterotrimer association/dissociation in the presence of the compound indicating that the chemical compound activates the mammalian G protein-coupled receptor and is a ligand for the mammalian G protein-coupled receptor.

The invention further provides a process for identifying a ligand for a mammalian G protein-coupled receptor which comprises contacting cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor, indicating that the compound is a ligand for the mammalian G protein-coupled receptor.

The inventions still further provides a process for identifying a chemical compound which specifically binds to a mammalian G protein-coupled receptor which comprises contacting a membrane preparation from cells transfected with and expressing DNA encoding a chimeric G protein and expressing DNA encoding a mammalian G protein-coupled receptor, wherein such cells do not normally express the DNA encoding the chimeric G protein, with the compound under conditions suitable for binding, and detecting specific binding of the chemical compound to the mammalian G protein-coupled receptor, indicating that the compound is a ligand for the mammalian G protein-coupled receptor.

In one embodiment of any of the aforementioned processes, the DNA encoding the mammalian G protein-coupled receptor is endogenous to the cell. In another embodiment, the DNA encoding the mammalian G protein-coupled receptor is transfected into the cell.

In one embodiment of any of the aforementioned processes, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαz protein beginning with the C-terminal amino acid of such vertebrate Gαz protein, wherein such number equals the number of amino acids deleted.

In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαs protein beginning with the C-terminal amino acid of such vertebrate Gαs protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gi3 protein beginning with the C-terminal amino acid of such vertebrate Gi3 protein, wherein such number equals the number of amino acids deleted.

In another embodiment, the chimeric G protein comprises an *Caenorhabditis elegans* Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In other embodiments, the chimeric G protein comprises a *Drosophila melanogaster* Gαq G protein, a *Limulus polyphemus* Gαq G protein, a *Patinopecten yessoensis* Gαq G protein, a *Loligo forbesi* Gαq G protein, a *Homarus americanus* Gαq G protein, a *Lymnaea stagnalis* Gαq G protein, a *Geodia cydonium* Gαq G protein, or a *Dictyostelium discoideum* Gα4 G protein, from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In other embodiments, the chimeric G protein has an amino acid sequence substantially the same as the amino acid sequence shown in (a) FIG. 2, *C. elegans* $G\alpha_{q/z5}$ (SEQ ID NO: 1); (b) FIG. 2, *C. elegans* $G\alpha_{q/z9}$ (SEQ ID NO: 2); (c) FIG. 2, *C. elegans* $G\alpha_{q/s9}$ (SEQ ID NO: 3); (d) FIG. 2, *C. elegans* $G\alpha_{q/s21}$ (SEQ ID NO: 4); (e) FIG. 2, *C. elegans* $G\alpha_{q/i3(5)}$ (SEQ ID NO: 5); or (f) FIG. 2, *D. melanogaster* $G\alpha_{q/zs}$ (SEQ ID NO: 41).

In one embodiment of any of the aforementioned processes, the cell is an insect cell. In another embodiment, the cell is a mammalian cell. In one embodiment, the mammalian cell is nonneuronal in origin. In further embodiments, the nonneuronal cell is a COS-7 cell, 293 human embryonic kidney cell, a CHO cell, a NIH-3T3 cell, a mouse Y1 cell, or a LM(tk−) cell.

The invention also provides a process of screening a plurality of independent clones not known to include a clone encoding a mammalian G protein-coupled receptor, to identify and isolate a clone encoding a mammalian G protein-coupled receptor, which comprises:
(a) contacting cells transfected with and expressing DNA encoding a chimeric G protein and expressing DNA encoding a plurality of independent clones with a ligand, under conditions permitting activation of a mammalian G protein-coupled receptor;
(b) determining whether the ligand activates the cells expressing the plurality of independent clones and the chimeric G protein; and if so
(c) isolating the single clone which expresses the mammalian G protein-coupled receptor activated by the ligand, so as to thereby identify any clone included in the plurality of clones as encoding a mammalian G protein-coupled receptor.

The invention further provides a process of screening a plurality of independent clones not known to include a clone encoding a mammalian G protein-coupled receptor, to identify and isolate a clone encoding a mammalian G protein-coupled receptor, which comprises:
(a) contacting cells transfected with and expressing DNA encoding a chimeric G protein and expressing DNA encoding a plurality of independent clones with a ligand, under conditions permitting specific binding to a mammalian G protein-coupled receptor;
(b) determining whether the ligand specifically binds to the cells expressing the plurality of independent clones and the chimeric G protein; and if so
(c) isolating the single clone which expresses the mammalian G protein-coupled receptor which specifically binds to the ligand, so as to thereby identify any clone included in the plurality of clones as encoding a mammalian G protein-coupled receptor.

In one embodiment of the aforementioned processes, the DNA encoding the plurality of independent clones is endogenous to the cell. In another embodiment, the DNA encoding the plurality of independent clones is transfected into the cell.

In one embodiment of the aforementioned processes, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαz protein beginning with the C-terminal amino acid of such vertebrate Gαz protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαs protein beginning with the C-terminal amino acid of such vertebrate Gαs protein, wherein such number equals the number of amino acids deleted. In another embodiment, the chimeric G protein comprises an invertebrate Gαq G protein from which at least five, but not more than twenty-one, contiguous amino acids beginning with the C-terminal amino acid have been deleted and replaced by a number of contiguous amino acids present in a vertebrate Gαi3 protein beginning with the C-terminal amino acid of such vertebrate Gαi3 protein, wherein such number equals the number of amino acids deleted.

In another embodiment, the chimeric G protein comprises an *Caenorhabditis elegans* Gαq G protein from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In other embodiments, the chimeric G protein comprises a *Drosophila melanogaster* Gαq G protein, a *Limulus polyphemus* Gαq G protein, a *Patinopecten yessoensis* Gαq G protein, a *Loligo forbesi* Gαq G protein, a *Homarus americanus* Gαq G protein, a *Lymnaea stagnalis* Gαq G protein, a *Geodia cydonium* Gαq G protein, or a *Dictyostelium discoideum* Gα$_4$ G protein, from which at least five, but not more than twenty-one, contiguous amino acids beginning with the C-terminal amino acid have been deleted and replaced by a number of contiguous amino acids present in a vertebrate G protein beginning with the C-terminal amino acid of such vertebrate G protein, wherein such number equals the number of amino acids deleted. In other embodiments, the chimeric G protein has an amino acid sequence substantially the same as the amino acid sequence shown in (a) FIG. 2, *C. elegans* Gα$_{q/z5}$ (SEQ ID NO: 1); (b) FIG. 2, *C. elegans* Gα$_{q/z9}$ (SEQ ID NO: 2); (c) FIG. 2, *C. elegans* Gα$_{q/s9}$ (SEQ ID NO: 3); (d) FIG. 2, *C. elegans* Gα$_{q/s21}$ (SEQ ID NO: 4); (e) FIG. 2, *C. elegans* Gα$_{q/i3(5)}$ (SEQ ID NO: 5); or (f) FIG. 2, *D. melanogaster* Gα$_{q/zs}$ (SEQ ID NO: 41).

In one embodiment of the aforementioned processes, the cell is an insect cell. In another embodiment, the cell is a mammalian cell. In one embodiment, the mammalian cell is nonneuronal in origin. In further embodiments, the nonneuronal cell is a COS-7 cell, 293 human embryonic kidney cell, a CHO cell, a NIH-3T3 cell, a mouse Y1 cell, or a LM(tk–) cell.

The invention provides a process for making a composition of matter which specifically binds to a mammalian G protein-coupled receptor which comprises identifying a chemical compound using any of the aforementioned processes and then synthesizing the chemical compound or a novel structural and functional analog or homolog thereof. The invention also provides a process for preparing a composition which comprises admixing a carrier and a pharmaceutically effective amount of a chemical compound identified by any of the aforementioned processes or a novel structural and functional analog or homolog thereof.

GPCRs that can be used with the invention include, but are not limited to, neuropeptide FF receptors, e.g., human NPFF1 (ATCC Accession number 203605) and human NPFF2 (ATCC Accession number 203255). Plasmid pcDNA3.1-hNPFF1 and plasmid pCDNA3.1-hNPFF2b were deposited on Jan. 21, 1999 and Sep. 22, 1998, respectively, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession Nos. 203605 and 203255, respectively.

Further GPCRs that can be used with the invention include, but are not limited to, serotonin receptors, e.g., human 5HT1D (U.S. Pat. No. 5,155,218, the disclosure of which is hereby incorporated by reference in its entirety into this application), rabbit 5HT1D (Harwood, G. et al., 1995), human 5HT7 (ATCC Accession number 75332), human 5HT1E (U.S. Pat. No. 5,476,782, the disclosure of which is hereby incorporated by reference in its entirety into this application), human 5HT1F (U.S. Pat. No. 5,360,735, the disclosure of which is hereby incorporated by reference in its entirety into this application), human 5HT5A (Plassat et al., 1992), human 5HT5B (Matthes et al., 1993), human 5HT1B (U.S. Pat. No. 5,155,218, the disclosure of which is hereby incorporated by reference in its entirety into this application), human 5HT4 (U.S. Pat. No. 5,766,879, the disclosure of which is hereby incorporated by reference in its entirety into this application), human 5HT6 (Kohen et al., 1996), and human 5HT1A (Kobilka et al., 1987). Plasmid pcEXV-5HT4B was deposited on Oct. 20, 1992 with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and was accorded ATCC Accession No. 75332.

Further GPCRs that can be used with the invention include, but are not limited to, dopamine receptors, e.g., human D1, human D2, human D3, and human D5 (U.S. Pat. No. 5,780,485, the disclosure of which is hereby incorporated by reference in its entirety into this application), and alpha adrenergic receptors, e.g., human α1A adr, human α2C adr, human α2B adr, human α2A adr (U.S. Pat. No. 5,780,485, the disclosure of which is hereby incorporated by reference in its entirety into this application), and human β2 adr (Dixon et al., 1986).

Further GPCRs that can be used with the invention include, but are not limited to, galanin receptors, e.g., human GALR1 (Habert-Ortoli et al., 1994), rat GALR1 (Burgevin et al., 1995), human GALR2 (ATCC Accession No. 97851), rat GALR2 (ATCC Accession No. 97426), human GALR3 (ATCC Accession No. 97827), and rat GALR3 (ATCC Accession No. 97826). Plasmids pEXJ-hGalR3 and pEXJ-rGALR3T were deposited on Dec. 17, 1996, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession Nos. 97827 and 97826, respectively. Plasmids B039 and K985 were deposited on Jan. 15, 1997 and Jan. 24, 1996, respectively, with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession Nos. 97851 and 97426, respectively.

Further GPCRs that can be used with the invention include, but are not limited to, neuropeptide Y receptors, e.g., human Y1 (Larhammar et al., 1992), rat Y1 (Eva et al., 1990), human Y2 (U.S. Pat. No. 5,545,549, the disclosure of which is hereby incorporated by reference in its entirety into this application), human Y4 (U.S. Pat. No. 5,516,653, the disclosure of which is hereby incorporated by reference in its entirety into this application), rat Y4 (ATCC Accession No. 75984), human Y5 (U.S. Pat. No. 5,602,024, the disclosure of which is hereby incorporated by reference in its entirety into this application), and rat Y5 (U.S. Pat. No. 5,602,024, the disclosure of which is hereby incorporated by reference in its entirety into this application). Plasmid pcEXV-rY4 was deposited on Dec. 21, 1994 with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession No. 75984.

Further GPCRs that can be used with the invention include, but are not limited to, neurotensin receptors, e.g., rat NTR1 (Tanaka et al., 1990); glucagon-like peptide receptors, e.g., human GLP-1 (Dillon et al., 1993); kappa opioid receptors, e.g., human kappa (Mansson et al., 1994); and melanin concentrating hormone receptors, e.g., human MCH (ATCC Accession No. 203197). Plasmid pEXJ.HR-TL231 was deposited on Sep. 17, 1998 with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure and were accorded ATCC Accession No. 203197.

The invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Cloning of the Gene Encoding C. elegans $G\alpha_q$

The gene for wild-type C. elegans $G\alpha_q$ was obtained by PCR amplification of a mixed stage C. elegans cDNA library (Stratagene, #937006) with the primers RP65 and RP66 (Table 1). The resulting product was cloned into the vector pcDNA 3.1 Zeo (Invitrogen) at the KpnI and XbaI sites. DNA sequence analysis demonstrated that the clone designated R48 was identical to that of the C. elegans $G\alpha_q$ gene deposited in Genbank (accession number AF003739).

Cloning of the Gene Encoding D. melanogaster $G\alpha_q$

The gene for wild-type D. melanogaster $G\alpha_q$ (isoform 3) was obtained by PCR amplification of D. melanogaster cDNA using primers RP203 and RP204 (Table 1). The resulting product was cloned into pcDNA3.1 (Invitrogen) at the KpnI and EcoRI sites. DNA sequence analysis demonstrated that the clone designated R129 encoded a protein identical to that of the D. melanogaster $G\alpha_{q3}$ gene deposited in Genbank (accession number P54400).

Cloning of Genes Encoding Human $G\alpha_q$

The sequence of human $G\alpha_q$ was confirmed by automated sequence analysis. Except for the substitution of a single amino acid at position 171 (Ala→Ser) in a highly non-conserved region of the protein, the deduced amino acid sequence is identical to that of Accession Number L76256. This sequence was used to generate the various human chimerae described throughout this application, except as noted in Table 9. A second human $G\alpha_q$ clone was obtained using standard PCR-based techniques that has a sequence identical to Genbank entry L76256. As expected, chimerae utilizing these two independently derived human $G\alpha_q$ sequences were found to be functionally indistinguishable in parallel assays (Table 9), using the dopamine D1 receptor as an example.

Construction of G Protein cDNAs with Chimeric 3' Ends

Most of the chimeric G protein cDNAs were made by a PCR approach (Table 2). In each case, the designated primers were used to amplify the 3' end of the appropriate template to generate a chimeric PCR product. This product was then subcloned back into wild-type human, D. melanogaster, or C. elegans $G\alpha_q$, as appropriate, to generate a full-length chimeric gene. All PCR derived sequences were verified by sequence analysis. Two chimeras (Table 3) were constructed using the QuikChange site-directed mutagenesis kit (Stratagene, #200518). For these clones, the sequence of the entire coding region was verified. Examples of chimeric G proteins used in the present application are depicted in FIG. 2.

TABLE 1

Primer sequences used in the preparation of chimeric G protein genes

| PRIMER | SEQUENCE | |
|---|---|---|
| MJ177 | 5' GAATATGATGGACCCCAGAGAGATG 3' | (SEQ ID NO: 19) |
| MJ178 | 5' GATCCTCGAGTTAGCACAGTCCGATGTACTTCAGGTTC AACTGGAGGATGGT 3' | (SEQ ID NO: 20) |
| MJ180 | 5' GATCCTCGAGTTAGTACAGTCCGCATCCCTTCAGGTTCA ACTGGAGGATGGT 3' | (SEQ ID NO: 21) |
| MJ193 | 5' GATCCTCGAGTTAGTAAAGCCCACATTCCTTCAGGTTC AACTGGAGGATGGT 3' | (SEQ ID NO: 22) |
| MJ194 | 5' GATCCTCGAGTTAGAGCAGCTCGTATTGCTTCAGGTTCA ACTGGAGGATGGT 3' | (SEQ ID NO: 23) |
| MJ197 | 5' GGAAAAAAGCGGCCGCTTAAAACAGTCCGCAGTCC TTCAGGTTCAACTGGAGGATGGT 3' | (SEQ ID NO: 24) |
| RP65 | 5' GGGGTACCGCCGCCATGGCCTGCTGTTTATCC 3' | (SEQ ID NO: 25) |
| RP66 | 5' GCTCTAGATTACACCAAGTTGTACTCCTTCAGATT 3' | (SEQ ID NO: 26) |
| RP80 | 5' CTCTCCGATCTCCGACGGCTG 3' | (SEQ ID NO: 27) |
| RP83 | 5' TTCTACAGCATAATCTGAAGTATATCGGTTTGTGTTAATCT AGAGGGCCCGTTTAAACCCGCTG 3' | (SEQ ID NO: 28) |
| RP84 | 5' CAGCGGGTTTAAACGGGCCCTCTAGATTAACACAAACCGAT ATACTTCAGATTATGCTGTAGAA 3' | (SEQ ID NO: 29) |

TABLE 1-continued

Primer sequences used in the preparation
of chimeric G protein genes

| PRIMER | SEQUENCE | |
|---|---|---|
| RP85 | 5' CAGCATAATCTGAAGGAGTGTGGATTGTACTAATCTAGA GGGCCCG 3' | (SEQ ID NO: 30) |
| RP86 | 5' CGGGCCCTCTAGATTAGTACAATCCACACTCCTTCAG ATTATGCTG 3' | (SEQ ID NO: 31) |
| RP116 | 5' GGAAAAAAGCGGCCGCTTAGAGCAGCTCGTATTGC CTCAGGTGCATCTGGAGGATGGTGTCCTTGACGG 3' | (SEQ ID NO: 32) |
| RP142 | 5' GCTCTAGATTAGAGCAGCTCGTATTGCCTCAGGTGCATCTG TAGAATTGTGTCTTTGACGGCG 3' | (SEQ ID NO: 33) |
| RP168 | 5' GCTCTAGATTAACATAGCCCTATGTATTTTAGATTATTCTG TAGAATTGTGTCTTTGACGGCG 3' | (SEQ ID NO: 34) |
| RP177 | 5' GCTCTAGATTAGAGCAGCTCGTATTGCCTCAGGTGCATACG TTGAATAATGTCACGACAGTCATTAAAAACACGCCGAATGT TTTCCGTATCAGTCGC 3' | (SEQ ID NO: 35) |
| RP203 | 5' CGGGGTACCCCGGTTAGCATGGAGTGCTGTTTATCG 3' | (SEQ ID NO: 42) |
| RP204 | 5' CCGGAATTCCGGTTAGACCAAATTATATTCCTTAAGGTTC 3' | (SEQ ID NO: 43) |
| RP218 | 5' GAGCATCGATTACGAGACCGTTACC 3' | (SEQ ID NO: 44) |
| RP219 | 5' CGGAATTCTTAGCACAGTCCGATGTACTTAAGGTTCGATTG CAGAATTGTGTC 3' | (SEQ ID NO: 45) |

TABLE 2

Primer pairs used to generate chimeric genes by PCR

| CHIMERA | PCR TEMPLATE | PRIMERS |
|---|---|---|
| Human G$\alpha_{q/z5}$ | hG$\alpha_q$ | MJ177/MJ178 |
| Human G$\alpha_{q/i2(5)}$ | hG$\alpha_q$ | MJ177/MJ197 |
| Human G$\alpha_{q/i3(5)}$ | hG$\alpha_q$ | MJ177/MJ193 |
| Human G$\alpha_{q/o5}$ | hG$\alpha_q$ | MJ177/MJ180 |
| Human G$\alpha_{q/s5}$ | hG$\alpha_q$ | MJ177/MJ194 |
| Human G$\alpha_{q/s9}$ | hG$\alpha_q$ | MJ177/RP116 |
| C. elegans G$\alpha_{q/s9}$ | R48 | RP80/RP142 |
| C. elegans G$\alpha_{q/s21}$ | R48 | RP80/RP177 |
| C. elegans G$\alpha_{q/z9}$ | R48 | RP80/RP168 |
| D. melanogaster G$\alpha_{q/z}$ | R129 | RP218/RP219 |

TABLE 3

Primer pairs used to generate chimeric genes using mutagenesis

| CHIMERA | TEMPLATE | PRIMERS |
|---|---|---|
| C. elegans G$\alpha_{q/i3(5)}$ | R48 | RP85/RP86 |
| C. elegans G$\alpha_{q/z5}$ | R48 | RP83/RP84 |

General Methods of Transfecting Cells

Methods of transfecting cells, e.g. mammalian cells, with such nucleic acid encoding a GPCR to obtain cells in which the GPCR is expressed on the surface of the cell are well known in the art. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.) The cells may be additionally transfected with nucleic acid encoding chimeric G proteins to obtain cells in which both the GPCR and the chimeric G proteins are expressed in the cell.

Such transfected cells may also be used to test compounds and screen compound libraries to obtain compounds which bind receptors as well as compounds which activate or inhibit activation of functional responses in such cells, and therefore are likely to do so in vivo. (See, for example, U.S. Pat. Nos. 5,053,337; 5,155,218; 5,360,735; 5,472,866; 5,476,782; 5,516,653; 5,545,549; 5,556,753; 5,595,880; 5,602,024; 5,639,652; 5,652,113; 5,661,024; 5,766,879; 5,786,155; and 5,786,157, the disclosures of which are hereby incorporated by reference in their entireties into this application.)

Host Cells

A broad variety of host cells can be used to study heterologously expressed proteins. These cells include but are not limited to mammalian cell lines such as; Cos-7, CHO, LM(tk⁻), HEK293, etc.; insect cell lines such as; Sf9, Sf21, etc.; amphibian cells such as *Xenopus* oocytes; assorted yeast strains; assorted bacterial cell strains; and others. Culture conditions for each of these cell types is specific and is known to those familiar with the art.

Transient Expression

DNA encoding proteins to be studied can be transiently expressed in a variety of mammalian, insect, amphibian, yeast, bacterial and other cells lines by several transfection methods including but not limited to: calcium phosphate-mediated, DEAE-dextran mediated; liposomal-mediated, viral-mediated, electroporation-mediated, and microinjection delivery. Each of these methods may require optimization of assorted experimental parameters depending on the DNA, cell line, and the type of assay to be subsequently employed.

Stable Expression

Heterologous DNA can be stably incorporated into host cells, causing the cell to perpetually express a foreign protein. Methods for the delivery of the DNA into the cell are similar to those described above for transient expression but require the co-transfection of an ancillary gene to confer drug resistance on the targeted host cell. The ensuing drug resistance can be exploited to select and maintain cells that have taken up the DNA. An assortment of resistance genes are available including but not restricted to neomycin, kanamycin, and hygromycin.

Mammalian Cell Tissue Culture and Transfection.

COS-7 cells were cultured in 225 cm² flasks in Dulbecco's Modified Eagle Medium (DMEM) with supplements (10% bovine calf serum, 4 mM glutamine, 100 units/ml penicillin and 100 µg/ml streptomycin) at 37° C., 5% $CO_2$. Stock plates of COS-7 cells were trypsinized and split 1:6 every 3–4 days.

GPCR and chimeric G protein cDNAs were transiently transfected into COS-7 cells in 150 $cm^2$ flasks by the DEAE-dextran method (Cullen, 1987), using a total of 20 µg of DNA/~7×$10^6$ cells. For evaluating the function of a single chimeric G protein, the standard cDNA transfection ratio was 1:1 (10 µg GPCR cDNA and 10 µg chimeric G protein cDNA). For evaluating the function of a mixture of chimeric G proteins, the standard cDNA transfection ratio was 8:1:1 (16 µg GPCR cDNA, 2 µg $G\alpha_{q/z}$ cDNA, 2 µg $G\alpha_{q/s}$ cDNA).

Membrane Preparations

Cell membranes expressing the heterologously expressed proteins of this invention are useful for certain types of assays including but not restricted to ligand binding assays, GTPγS binding assays, and others. The specifics of preparing such cell membranes may in some cases be determined by the nature of the ensuing assay but typically involve harvesting whole cells and disrupting the cell pellet by sonication in ice cold buffer (e.g. 20 mM Tris-HCl, 5 mM EDTA, pH 7.4). The resulting crude cell lysate is cleared of cell debris by low speed centrifugation at 200×g for 5 min at 4° C. The cleared supernatant is then centrifuged at 40,000×g for 20 min at 4° C., and the resulting membrane pellet is washed by suspending in ice cold buffer and repeating the high speed centrifugation step. The final washed membrane pellet is resuspended in assay buffer. Protein concentrations are determined by the method of Bradford (1976) using bovine serum albumin as a standard. The membranes may be used immediately or frozen for later use.

Generation of Baculovirus

The coding region of DNA encoding the human receptor and the chimeric G protein disclosed herein may be separately subcloned into pBlueBacIII into existing restriction sites or sites engineered into sequences 5' and 3' to the coding region of the polypeptides. To generate baculovirus, 0.5 µg of viral DNA (BaculoGold) and 3 µg of DNA construct encoding a polypeptide may be co-transfected into 2×$10^6$ *Spodoptera frugiperda* insect Sf9 cells by the calcium phosphate co-precipitation method, as outlined by Pharmingen (in "Baculovirus Expression Vector System: Procedures and Methods Manual"). The cells are then incubated for 5 days at 27° C.

The supernatant of the co-transfection plate may be collected by centrifugation and the recombinant virus plaque purified. The procedure to infect cells with virus, to prepare stocks of virus and to titer the virus stocks are as described in Pharmingen's manual.

Binding Assays

Labeled ligands are placed in contact with either membrane preparations or intact cells expressing the chimeric G protein and receptor of interest in multi-well microtiter plates, together with unlabeled compounds, and binding buffer. Binding reaction mixtures are incubated for times and temperatures determined to be optimal in separate equilibrium binding assays. The reaction is stopped by filtration through GF/B filters, using a cell harvester, or by directly measuring the bound ligand. If the ligand was labeled with a radioactive isotope such as $^3H$, $^{14}C$, $^{125}I$, $^{35}S$, $^{32}P$, $^{33}P$, etc., the bound ligand may be detected by using liquid scintillation counting, scintillation proximity, or any other method of detection for radioactive isotopes. If the ligand was labeled with a fluorescent compound, the bound labeled ligand may be measured by methods such as, but not restricted to, fluorescence intensity, time resolved fluorescence, fluorescence polarization, fluorescence transfer, or fluorescence correlation spectroscopy. In this manner, agonist or antagonist compounds that bind to the receptor may be identified as they inhibit the binding of the labeled ligand to the membrane protein or intact cells expressing the said receptor. Non-specific binding is defined as the amount of labeled ligand remaining after incubation of membrane protein in the presence of a high concentration (e.g., 100–1000×$K_D$) of unlabeled ligand. In equilibrium saturation binding assays membrane preparations or intact cells transfected with the chimeric G protein and GPCR are incubated in the presence of increasing concentrations of the labeled compound to determine the binding affinity of the labeled ligand. The binding affinities of unlabeled compounds may be determined in equilibrium competition binding assays, using a fixed concentration of labeled compound in the presence of varying concentrations of the displacing ligands.

Functional Assays

Cells expressing the chimeric G protein DNA of this invention and a GPCR may be used to screen for ligands to the GPCR using functional assays. Once a ligand is identified, the same assays may be used to identify agonists or antagonists of the GPCR that may be employed for a variety of therapeutic purposes.

It is well known to those in the art that the over-expression of a G protein-coupled receptor can result in the constitutive activation of intracellular signaling pathways. In the same manner, over-expression of an orphan receptor and a chimeric G protein in any cell line as described above, can result in the activation of the functional responses described below, and any of the assays herein described can be used to screen for both agonist and antagonist ligands of the orphan receptor.

A wide spectrum of assays can be employed to screen for the presence of orphan receptor ligands or to identify agonists or antagonists of a characterized GPCR. These assays range from traditional measurements of total inositol phosphate accumulation, cAMP levels, intracellular calcium mobilization, and potassium currents, for example; to systems measuring these same second messengers, but which have been modified or adapted to be of higher throughput, more generic, and more sensitive; to cell based assays reporting more general cellular events resulting from receptor activation such as metabolic changes, differentiation, cell division/proliferation. Description of several such assays follow.

Cyclic AMP (cAMP) Assay

Elevation of intracellular $Ca^{++}$ can modulate the activity of adenylyl cyclases via $Ca^{++}$-dependent calmodulin (Sunahara et al., 1996). The receptor-mediated stimulation or inhibition of cyclic AMP (cAMP) formation may be assayed in cells expressing a GPCR and chimeric G protein. Cells are plated in 96-well plates or other vessels and preincubated in a buffer such as HEPES buffered saline (NaCl (150 mM), $CaCl_2$ (1 mM), KCl (5 mM), glucose (10 mM)) supplemented with a phosphodiesterase inhibitor such as 5 mM theophylline, with or without protease inhibitor cocktail for 20 min at 37° C., in 5% $CO_2$. A typical inhibitor cocktail contains 2 µg/ml aprotinin, 0.5 mg/ml leupeptin, and 10 µg/ml phosphoramidon. Test compounds are added with or without 10 mM forskolin and incubated for an additional 10 min at 37° C. The medium is then aspirated and the reaction stopped by the addition of 100 mM HCl or other methods.

The plates are stored at 4° C. for 15 min, and the cAMP content in the stopping solution is measured by radioimmunoassay. Radioactivity may be quantified using a gamma counter equipped with data reduction software. Specific modifications may be performed to optimize the assay for the GPCR or to alter the detection method of cAMP.

Arachidonic Acid Release Assays

Cells expressing a GPCR and chimeric G protein are seeded into 96 well plates or other vessels and grown for 3 days in medium with supplements. $^3$H-arachidonic acid (specific activity=0.75 µCi/ml) is delivered as a 100 µL aliquot to each well and samples are incubated at 37° C., 5% $CO_2$ for 18 hours. The labeled cells are washed three times with medium. The wells are then filled with medium and the assay is initiated with the addition of test compounds or buffer in a total volume of 250 µL. Cells are incubated for 30 min at 37° C., 5% $CO_2$. Supernatants are transferred to a microtiter plate and evaporated to dryness at 75° C. in a vacuum oven. Samples are then dissolved and resuspended in 25 µL distilled water. Scintillant (300 µL) is added to each well and samples are counted for $^3$H in a Trilux plate reader. Data are analyzed using nonlinear regression and statistical techniques available in the GraphPAD Prism package (San Diego, Calif.).

Intracellular Calcium Mobilization Assay

Twenty four hours after transient transfection, COS-7 cells were seeded into 96-well black wall microtiter plates coated with poly-D-lysine for assay the following day. Just prior to assay, culture medium was aspirated and cells were dye-loaded with 4 µM Fluo-3/0.01% pluronic acid in assay buffer composed of Hank's Balanced Salt Solution (138 mM NaCl, 5 mM KCl, 1.3 mM $CaCl_2$, 0.5 mM $MgCl_2$, 0.4 mM $MgSO_4$, 0.3 mM $KH_2PO_4$, 0.3 mM $Na_2HPO_4$, 5.6 mM glucose) plus 20 mM HEPES (pH 7.4), 0.1% BSA and 2.5 mM probenicid (100 µl/well) for 1 hour in 5% $CO_2$ at 37° C. After excess dye was discarded, cells were washed in assay buffer and layered with a final volume equal to 100 µl/well. Basal fluorescence was monitored in a fluorometric imaging plate reader (FLIPR™, Molecular Devices) with an excitation wavelength of 488 nm and an emission range of 500 to 560 nm. Laser excitation energy was adjusted so that basal fluorescence readings were approximately 10,000 relative fluorescent units. Cells were stimulated with agonists diluted in assay buffer (50 µl), and relative fluorescent units were measured at defined intervals (exposure=0.4 sec) over a 3 min period at room temperature. Maximum change in fluorescence was calculated for each well. Concentration-response curves derived from the maximum change in fluorescence were analyzed by nonlinear regression (Hill equation).

Alternatively, intracellular free calcium concentration may be measured by microspectrofluorimetry using the fluorescent indicator dye Fura-2/AM (Bush et al, 1991). Cells expressing the receptor and chimeric G protein are seeded onto a 35 mm culture dish containing a glass coverslip insert and allowed to adhere overnight. Cells are then washed with HBS and loaded with 100 µL of Fura-2/AM (10 µM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Alternative calcium-sensitive indicators may be used. Preferred examples of these are: aequorin, Fluo-3, Fluo-4, Fluo-5, Calcium Green-1, Oregon Green, and 488 BAPTA. After activation of the receptors with agonist ligands the emission elicited by the change of intracellular calcium concentration can be measured by a luminometer or a fluorescence imager; a preferred example of this is the fluorescence imager plate reader (FLIPR™) as described above. Antagonist ligands are identified by the inhibition of the signal elicited by agonist ligands.

Inositol Phosphate Assay

Receptor mediated activation of the inositol phosphate (IP) second messenger pathways may be assessed by radiometric or other measurement of IP products. For example, in a 96 well microplate format assay, cells are plated at a density of 70,000 cells per well and allowed to incubate for 24 hours. The cells are then labeled with 0.5 µCi [$^3$H]myo-inositol overnight at 37° C., 5% $CO_2$. Immediately before the assay, the medium is removed and replaced with 90 µL of PBS containing 10 mM LiCl. The plates are then incubated for 15 min at 37° C., 5% $CO_2$. Following the incubation, the cells are challenged with agonist (10 µl/well; 10× concentration) for 30 min at 37° C., 5% $CO_2$. The challenge is terminated by the addition of 100 µL of 50% v/v trichloroacetic acid, followed by incubation at 4° C. for greater than 30 minutes. Total IPs are isolated from the lysate by ion exchange chromatography. Briefly, the lysed contents of the wells are transferred to a Multiscreen HV filter plate (Millipore) containing Dowex AG1-X8 (200–400 mesh, formate form). The filter plates are prepared adding 100 µL of Dowex AG1-X8 suspension (50% v/v, water: resin) to each well. The filter plates are placed on a vacuum manifold to wash or elute the resin bed. Each well is first washed 2 times with 200 µl of 5 mM myo-inositol. Total [$^3$H]inositol phosphates are eluted with 75 µl of 1.2 M ammonium formate/0.1 M formic acid solution into 96-well plates. 200 µL of scintillation cocktail is added to each well and the radioactivity is determined by liquid scintillation counting.

GTPγS Binding Assay

Membranes from cells expressing a GPCR and a chimeric G protein are suspended in assay buffer (e.g., 50 mM Tris, 100 mM NaCl, 5 mM $MgCl_2$, 10 µM GDP, pH 7.4) with or without protease inhibitors (e.g., 0.1% bacitracin). Membranes are incubated on ice for 20 minutes, transferred to a 96-well Millipore microtiter GF/C filter plate and mixed with GTPγ$^{35}$S (e.g., 250,000 cpm/sample, specific activity ~1000 Ci/mmol) plus or minus unlabeled GTPγS (final concentration=100 µM). The final membrane protein concentration is approximately 20 µg/ml. Samples are incubated in the presence or absence of test compounds for 30 minutes at room temperature, then filtered on a Millipore vacuum manifold and washed three times with cold (4° C.) assay buffer. Samples collected in the filter plate are treated with scintillant and counted for $^{35}$S in a Trilux (Wallac) liquid scintillation counter. It is expected that optimal results are obtained when the receptor membrane preparation is derived from an appropriately engineered heterologous expression system, i.e., an expression system resulting in high levels of expression of the receptor and/or expressing G proteins having high turnover rates (for the exchange of GDP for GTP). GTPγS assays are well-known to those skilled in the art, and it is contemplated that variations on the method described above, such as are described by Tian et al. (1994) or Lazareno and Birdsall (1993), may be used.

MAP Kinase Assay

MAP kinase (mitogen activated kinase) may be monitored to evaluate receptor activation. MAP kinase is activated by multiple pathways in the cell. A primary mode of activation involves the ras/raf/MEK/MAP kinase pathway. Growth factor (tyrosine kinase) receptors feed into this pathway via SHC/Grb-2/SOS/ras. Gi coupled receptors are also known to activate ras and subsequently produce an activation of MAP kinase. Receptors that activate phospholipase C (such as Gq/G11-coupled) produce diacylglycerol (DAG) as a consequence of phosphatidyl inositol hydrolysis. DAG activates protein kinase C which in turn phosphorylates MAP kinase.

MAP kinase activation can be detected by several approaches. One approach is based on an evaluation of the phosphorylation state, either unphosphorylated (inactive) or phosphorylated (active). The phosphorylated protein has a slower mobility in SDS-PAGE and can therefore be compared with the unstimulated protein using Western blotting. Alternatively, antibodies specific for the phosphorylated protein are available (New England Biolabs) which can be used to detect an increase in the phosphorylated kinase. In either method, cells are stimulated with the test compound and then extracted with Laemmli buffer. The soluble fraction is applied to an SDS-PAGE gel and proteins are transferred electrophoretically to nitrocellulose or Immobilon. Immunoreactive bands are detected by standard Western blotting technique. Visible or chemiluminescent signals are recorded on film and may be quantified by densitometry.

Another approach is based on evaluation of the MAP kinase activity via a phosphorylation assay. Cells are stimulated with the test compound and a soluble extract is prepared. The extract is incubated at 30° C. for 10 min with gamma-$^{32}$P-ATP, an ATP regenerating system, and a specific substrate for MAP kinase such as phosphorylated heat and acid stable protein regulated by insulin, or PHAS-I. The reaction is terminated by the addition of $H_3PO_4$ and samples are transferred to ice. An aliquot is spotted onto Whatman P81 chromatography paper, which retains the phosphorylated protein. The chromatography paper is washed and counted for $^{32}$P in a liquid scintillation counter. Alternatively, the cell extract is incubated with gamma-$^{32}$P-ATP, an ATP regenerating system, and biotinylated myelin basic protein bound by streptavidin to a filter support. The myelin basic protein is a substrate for activated MAP kinase. The phosphorylation reaction is carried out for 10 min at 30° C. The extract can then by aspirated through the filter, which retains the phosphorylated myelin basic protein. The filter is washed and counted for $^{32}$P by liquid scintillation counting.

Cell Proliferation Assay

Receptor activation of a GPCR may lead to a mitogenic or proliferative response which can be monitored via $^3$H-thymidine uptake. When cultured cells are incubated with $^3$H-thymidine, the thymidine translocates into the nuclei where it is phosphorylated to thymidine triphosphate. The nucleotide triphosphate is then incorporated into the cellular DNA at a rate that is proportional to the rate of cell growth. Typically, cells are grown in culture for 1–3 days. Cells are forced into quiescence by the removal of serum for 24 hrs. A mitogenic agent is then added to the media. Twenty-four hrs later, the cells are incubated with $^3$H-thymidine at specific activities ranging from 1 to 10 μCi/ml for 2–6 hrs. Harvesting procedures may involve trypsinization and trapping of cells by filtration over GF/C filters with or without a prior incubation in TCA to extract soluble thymidine. The filters are processed with scintillant and counted for $^3$H by liquid scintillation counting. Alternatively, adherent cells are fixed in MeOH or TCA, washed in water, and solubilized in 0.05% deoxycholate/0.1 N NaOH. The soluble extract is transferred to scintillation vials and counted for $^3$H by liquid scintillation counting.

Alternatively, cell proliferation can be assayed by measuring the expression of an endogenous or heterologous gene product, expressed by the cell line used to transfect the GPCR, which can be detected by methods such as, but not limited to, fluorescence intensity, enzymatic activity, immunoreactivity, DNA hybridization, polymerase chain reaction, etc.

Reporter Gene Assays

The chimeric Gα subunits described in this application can be used in conjunction with any number of $Gα_q$-linked transcriptional assays to include GPCRs that do not normally use $Gα_q$ as their native signaling pathway. This application could include, but is not limited to, the use of Gα chimeras to link activation of any GPCR to a fluorescent signal generated via a reporter enzyme such as β-lactamase placed under the transcriptional regulation of NFAT, SRE, CRE, AP-1, TRE IRE or other specific DNA regulatory elements or promoters (Naylor, 1999).

Methods for Recording Currents in Xenopus oocytes

Oocytes were harvested from Xenopus laevis and injected with mRNA transcripts as previously described (Quick and Lester, 1994; Smith et al., 1997). Receptor and chimeric G protein α subunit RNA transcripts were synthesized using the T7 polymerase ("Message Machine," Ambion) from linearized plasmids or PCR products containing the complete coding region of the genes. Oocytes were injected with 5–25 ng synthetic receptor RNA and incubated for 3–8 days at 17 degrees. Three to eight hours prior to recording, oocytes were injected with 500 pg chimeric Gα subunit mRNA. Dual electrode voltage clamp (Axon Instruments Inc.) was performed using 3 M KCl-filled glass microelectrodes having resistances of 1–2 MOhm. Unless otherwise specified, oocytes were voltage clamped at a holding potential of –80 mV. During recordings, oocytes were bathed in continuously flowing (1–3 ml/min) medium containing 96 mM NaCl, 2 mM KCl, 1.8 mM $CaCl_2$, 1 mM $MgCl_2$, and 5 mM HEPES, pH 7.5 (ND96). Drugs were applied by local perfusion from a 10 μl glass capillary tube fixed at a distance of 0.5 mm from the oocyte. Experiments were carried out at room temperature. All values are expressed as mean±standard error of the mean.

Beta-Gamma-Dependent Signaling

Beta-gamma sub-units released from $Gα_q$ may interact with a variety of effectors, including phospholipase C beta, adenylate cyclase II and IV, ion channels (Kir 3.x family of $K^+$ channels, calcium channels), Ras and PI-3-gamma. Each of these may be monitored by specific read-outs known to those skilled in the art.

Expression Cloning

The expression cloning strategy is a well-known method utilized to clone mammalian G protein-coupled receptors (Kluxen et al., 1992; Kiefer et al, 1992; Julius et al., 1988; U.S. Pat. No. 5,545,549 and U.S. Pat. No. 5,602,024, the disclosures of which are hereby incorporated by reference in their entireties into this application). A chimeric G protein of this invention may be utilized in expression cloning to facilitate identification of clones which encode mammalian G protein-coupled receptors. Cells, expressing the DNA encoding numerous independent clones, may be transfected with and express DNA encoding a chimeric G protein of this invention. The presence of the chimeric G protein in the cells may facilitate ligand activation of or binding to a mammalian G protein-coupled receptor encoded by one of the independent clones which may be subsequently isolated.

Results and Discussion

Expression of C. elegans Chimera in Xenopus oocytes

The chimeric Gα subunit consisting of $cG\alpha_{q/z5}$, wherein the C-terminal final 5 amino acids of $cG\alpha_q$ are replaced with those of $hG\alpha_z$ (FIG. 2), was initially tested for expression and functional activity in Xenopus oocytes. Co-expression of $cG\alpha_{q/z5}$ with the NPFF1 receptor resulted in the appearance of large amplitude Cl⁻ currents following application of 1 μM NPFF (1258±159 nA, n=12). The currents stimulated by NPFF in oocytes expressing NPFF1 and $cG\alpha_{q/z5}$ were most likely mediated by the endogenous calcium-activated Cl⁻ channel (Gunderson et al., 1983), because they were blocked in oocytes injected with 50 nl of 10 mM EGTA (FIG. 3). Chloride currents were also not observed from control oocytes expressing NPFF1 but lacking $cG\alpha_{q/z5}$ (n=15). In oocytes expressing NPFF1 and the human version of $G\alpha_{q/z5}$, response amplitudes (358±67, n=32) were about one third of those in oocytes expressing the C. elegans version of this chimera. Similar results were obtained with four additional GPCRs, GALR1, Y1, NPFF2, and 5HT1D, that are known to couple to either $G\alpha_i$ or $G\alpha_o$ (Table 4; Watling, 1998). The increase in response was 2–3 fold over currents recorded from oocytes expressing the human version of the chimera. The exception to this trend was coupling to the Y5 receptor, which was actually reduced with $cG\alpha_{q/z5}$. Extending the length of the $G\alpha_z$ portion of the C-terminal tail of $cG\alpha_q$ to 9 amino acids ($cG\alpha_{q/z9}$) did not further improve the amplitude of responses as compared to $cG\alpha_{q/z5}$ (Table 4).

TABLE 4

Response amplitudes (nA) in oocytes expressing various GPCRs and chimeric G proteins. Values are mean ± s.e.m (number of oocytes)

| RECEPTOR | CHIMERA | | |
|---|---|---|---|
| | $hG\alpha_{q/z5}$ | $CG\alpha_{q/z5}$ | $CG\alpha_{q/z9}$ |
| Rabbit 5HT1D | 90 ± 41 (14) | 150 ± 105 (8) | 34 ± 12 (9) |
| Rat GALR1 | 31 ± 16 (22) | 91 ± 38 (15) | Not tested |
| Human NPFF1 | 358 ± 67 (32) | 1258 ± 159 (12) | 1449 ± 398 (5) |
| Human NPFF2 | 528 ± 99 (18) | 1121 ± 261 (13) | Not tested |
| Rat Y1 | 841 ± 204 (19) | 1549 ± 168 (13) | 300 ± 177 (8) |
| Rat Y5 | 82 ± 43 (7) | 0 ± 2 (8) | 65 ± 34 (6) |

Expression of Chimeras in Mammalian Cells

To evaluate the utility of $cG\alpha_{q/z5}$ in mammalian cells, COS-7 cells were transiently transfected with either $hG\alpha_{q/z5}$ or $cG\alpha_{q/z5}$ plus a GPCR. In one example, cells transfected either with $hG\alpha_{q/z5}$ or $cG\alpha_{q/z5}$ plus the human D1 receptor, which is thought to be $G\alpha_s$- and $G\alpha_{i/o}$-coupling (Sidhu et al., 1991), were stimulated with dopamine at concentrations up to 100 μM and monitored for calcium mobilization (FIG. 4). Whereas an agonist-induced response was undetectable with $hG\alpha_{q/z5}$ (n=2), the $cG\alpha_{q/z5}$ construct supported an average maximum dopamine-stimulated signal of 12, 120 relative fluorescence units (n=2).

The data for human D1 clearly demonstrate that the probability of GPCR signal detection in mammalian cells can be enhanced by the use of a chimeric construct containing an invertebrate Gαq backbone (C. elegans $G\alpha_q$ in this case). To determine whether this effect extends to a broad range of GPCRs, $cG\alpha_{q/z5}$ was co-transfected into COS-7 cells with a panel of 36 different GPCRs, including $G\alpha_{i/i}$-, $G\alpha_s$-, and $G\alpha_q$-coupling receptors. Seventy eight percent (28/36) of the receptors generated positive signals (defined as >500 fluorescence units) with $cG\alpha_{q/z5}$, compared to only 58% with $hG\alpha_{q/z5}$ (Table 5). Extending the $G\alpha_z$ tail length from 5 to 9 amino acids did not significantly change the detection rate (29/36 positive responses >500 fluorescence units) but there was a trend, particularly among the most responsive receptors, toward a decreased maximal response. From these data, we can conclude that an invertebrate-based $G\alpha_{q/z}$ construct is optimal for detecting a broad range of GPCR, and we can identify $cG\alpha_{q/z5}$ as a preferred design.

TABLE 5

$G\alpha_{q/z5}$ chimeras and GPCR in COS-7 cells: agonist-induced response. Transfected cells were monitored for calcium mobilization in the FLIPR ™ using the calcium sensitive dye Fluo-3. Maximum agonist concentrations were 100 μM for non-peptide ligands or 10 μM for peptide ligands, except for neurotensin (1 μM). Fluorescence data represent the mean from 2 or more experiments. h = human; m = mouse; r = rat; adr = adrenergic; DA = dopamine; GLP-1 = glucagon-like peptide; 5HT = serotonin; GAL = galanin; NE = norepinephrine; MCH = melanin-concentrating hormone; NPY = neuropeptide Y; PP = pancreatic polypeptide; NPFF = neuropeptide FF; and NT = neurotensin

| # | RECEPTOR | PROPOSED COUPLING | AGONIST | MAXIMAL SIGNAL (FLUORESCENCE UNITS) | | |
|---|---|---|---|---|---|---|
| | | | | $hG\alpha_{q/z5}$ | $cG\alpha_{q/z5}$ | $cG\alpha_{q/z9}$ |
| 1 | h D3 | $G\alpha_{i/o}$ | DA | 0 | 0 | 121 |
| 2 | h GLP-1 | $G\alpha_s$ | GLP-1 | 287 | 131 | 135 |
| 3 | h 5HT7 | $G\alpha_s$ | 5HT | 90 | 166 | 129 |
| 4 | h 5HT1E | $G\alpha_{i/o}$ | 5HT | 202 | 229 | 238 |
| 5 | h 5HT1F | $G\alpha_{i/o}$ | 5HT | 0 | 243 | 384 |
| 6 | m 5HT5B | $G\alpha_{i/o}$ | 5HT | 251 | 265 | 443 |
| 7 | m 5HT5A | $G\alpha_{i/o}$ | 5HT | 0 | 351 | 270 |
| 8 | h 5HT1D | $G\alpha_{i/o}$ | 5HT | 316 | 414 | 504 |
| 9 | h D5 | $G\alpha_s$, $G\alpha_{i/o}$ | DA | 782 | 657 | 797 |
| 10 | h 5HT1B | $G\alpha_{i/o}$ | 5HT | 405 | 929 | 1217 |
| 11 | h 5HT4 | $G\alpha_s$, $G\alpha_q$ | 5HT | 2161 | 1011 | 1696 |
| 12 | h 5HT6 | $G\alpha_s$ | 5HT | 210 | 1289 | 2287 |
| 13 | h GALR3 | $G\alpha_{i/o}$ | GAL | 804 | 1523 | 2050 |
| 14 | h β2 adr | $G\alpha_s$, $G\alpha_{i/o}$ | NE | 128 | 1842 | 1697 |
| 15 | h 5HT1A | $G\alpha_{i/o}$ | 5HT | 478 | 1997 | 3139 |
| 16 | r GALR3 | $G\alpha_{i/o}$ | GAL | 2796 | 2298 | 2971 |
| 17 | h MCH | $G\alpha_q$ | MCH | 783 | 2699 | 3332 |
| 18 | r GALR1 | $G\alpha_{i/o}$ | GAL | 82 | 3086 | 5947 |
| 19 | r Y4 | $G\alpha_{i/o}$ | PP | 4388 | 3662 | 2583 |
| 20 | h α2C adr | $G\alpha_{i/o}$ | NE | 6106 | 4143 | 3874 |
| 21 | r GALR2 | $G\alpha_q$ | GAL | 4862 | 4198 | 4470 |
| 22 | h α2B adr | $G\alpha_{i/o}$ | NE | 4515 | 4983 | 5138 |
| 23 | h Y5 | $G\alpha_{i/o}$ | NPY | 6407 | 5314 | 6680 |
| 24 | h GALR2 | $G\alpha_q$ | GAL | 5992 | 5470 | 4899 |
| 25 | h kappa | $G\alpha_{i/o}$ | U-69593 | 7864 | 5975 | 3472 |
| 26 | h NPFF1 | $G\alpha_{i/o}$ | NPFF | 4717 | 6593 | 2966 |
| 27 | h NPFF2 | $G\alpha_{i/o}$ | NPFF | 19960 | 7566 | 4578 |
| 28 | h α2A adr | $G\alpha_{i/o}$ | NE | 10933 | 7575 | 3040 |
| 29 | h D2 | $G\alpha_{i/o}$ | DA | 15579 | 7615 | 4305 |
| 30 | h GALR1 | $G\alpha_{i/o}$ | GAL | 4061 | 7648 | 8489 |
| 31 | h Y2 | $G\alpha_{i/o}$ | NPY | 10908 | 7708 | 5387 |
| 32 | h Y1 | $G\alpha_{i/o}$ | NPY | 1879 | 7722 | 6728 |
| 33 | h Y4 | $G\alpha_{i/o}$ | PP | 9966 | 9422 | 7397 |
| 34 | h α1A adr | $G\alpha_q$ | NE | 14167 | 9816 | 6597 |
| 35 | h D1 | $G\alpha_s$, $G\alpha_{i/o}$ | DA | 0 | 12120 | 13099 |
| 36 | r NTR1 | $G\alpha_q$ | NT | 11171 | 14476 | 6111 |

$G\alpha_{q/s}$ Chimeras

To identify additional uses for an invertebrate-based $G\alpha_q$ construct, modifications were made to the backbone and C-terminus of another type of chimera, $G\alpha_{q/s}$. Initially, the function of $hG\alpha_{q/s5}$ was compared with that of $hG\alpha_{q/s9}$. In one example, either construct was co-transfected into COS-7 cells with the human D1 receptor, which is typically $G\alpha_s$- or $G\alpha_{i/o}$-coupling (Sidhu et al., 1991). Transfected cells were stimulated with dopamine at concentrations up to 100 µM and monitored for calcium mobilization. The average maximal agonist-induced response ranged from undetectable with $hG\alpha_{q/s5}$ (n=2) to 5692 relative fluorescent units with $hG\alpha_{q/s9}$ (n=4). The positive effect of increasing the $G\alpha_s$ tail length contrasts with data for *C. elegans* $G\alpha_{q/z}$-type chimeras and has not been described previously (Conklin et al., 1993, 1996). To further enhance signal detection, the human $G\alpha_q$ backbone was replaced with the corresponding sequence from *C. elegans* $G\alpha_q$. The modified construct, $cG\alpha_{q/s9}$, was co-transfected into COS-7 cells together with the human D1 receptor, and transfected cells were stimulated with dopamine at concentrations up to 100 µM. The average maximal dopamine-stimulated fluorescent signal with $cG\alpha_{q/s9}$ was 8692 fluorescent units (n=4), a 1.5-fold increase over the response with $hG\alpha_{q/s9}$. To test the general utility of $cG\alpha_{q/s9}$ for detection of $G\alpha_s$-coupling receptors, this construct was co-transfected into COS-7 with a panel of 7 such GPCR. When cells were stimulated with appropriate agonists, 6/7=81% of the $G\alpha_s$-coupling receptors generated positive responses (>500 fluorescence units). Further extension of the C-terminal $G\alpha_s$ tail to 21 amino acids ($cG\alpha_{q/s21}$) yielded similar results overall, both in terms of detection rate and maximal response (Table 6).

TABLE 6

$G\alpha_{q/s}$ chimeras and Gs-coupled receptors in COS-7 cells: maximum agonist response. Transfected cells were monitored for calcium mobilization in the FLIPR ™ using the calcium sensitive dye Fluo-3. Maximal agonist concentration was 100 µM for non-peptide ligands or 10 µM for GLP-1 (7-36) amide. Fluorescence data represent the mean from 2 or more experiments. h = human, adr = adrenergic, DA = dopamine; GLP-1 = glucagon-like peptide; 5HT = serotonin; NE = norepinephrine

| | | | MAXIMAL SIGNAL (FLUORESCENCE UNITS) | | | |
|---|---|---|---|---|---|---|
| # | RECEPTOR | AGONIST | $hG\alpha_{q/s5}$ | $HG\alpha_{q/s9}$ | $cG\alpha_{q/s9}$ | $cG\alpha_{q/s21}$ |
| 1 | h GLP-1 | GLP-1 | 189 | 4198 | 2461 | 3120 |
| 2 | h 5HT7 | 5HT | 0 | 0 | 387 | 206 |
| 3 | h D5 | DA | 0 | 745 | 1870 | 3385 |
| 4 | h 5HT4 | 5HT | 1709 | 2309 | 1701 | 1731 |
| 5 | h 5HT6 | 5HT | 98 | 999 | 1639 | 1009 |
| 6 | h β2 adr | NE | 43 | 1439 | 3106 | 3513 |
| 7 | h D1 | DA | 0 | 5692 | 8692 | 9433 |

That the *C. elegans* backbone provides a signaling advantage when incorporated into either $G\alpha_{q/z}$-type or $G\alpha_{q/s}$-type chimeras suggests a novel and general method for designing effective chimeric constructs. In yet another example, human $G\alpha_{q/i3(5)}$ was compared with *C. elegans* $G\alpha_{q/i3(5)}$ using COS-7 cells transfected with the rat GALR3 receptor. The maximum signal produced by porcine galanin was 2084 relative fluorescent units with human $G\alpha_{q/i3(5)}$ (n=4), compared to 2564 fluorescent units with *C. elegans* $G\alpha_{q/i3(5)}$ (n=4). These data extend the range of possible uses for a *C. elegans* backbone in a $G\alpha_q$ chimeric construct.

Multiple Chimerae Strategies

Application of this technology to a high throughput screening paradigm (such as orphan receptor screening or expression cloning) requires that a maximal number of chimera-dependent receptors ($G\alpha_{i/o}$, and $G\alpha_s$-coupling) can function under the same conditions as chimera-independent receptors ($G\alpha_q$-coupled). One strategy, described above, is to use a single extremely promiscuous construct such as $cG\alpha_{q/z5}$.

Another strategy is to combine multiple chimeras in a transfection mixture. Ideally, the mixture should be reduced to its essential components, both in terms of individual chimera and corresponding cDNA or mRNA. A reductionist approach has several advantages: 1) it increases the allowance for cDNA or mRNA encoding the GPCR of interest; 2) it reduces potential competition for protein translation; and 3) it reduces the risk for dominant negative suppression of Gq-coupled receptor function. A simple and effective combination could be formed with a $cG\alpha_{q/z}$-type chimera and a $cG\alpha_{q/s}$-type chimera. In one example, a transfection mixture containing 2 µg $cG\alpha_{q/z9}$ cDNA, 2 µg $cG\alpha_{q/s9}$ cDNA, and 16 µg GPCR cDNA was transfected into COS-7 cells for subsequent monitoring of calcium mobilization. Out of 36 receptors tested, 28 receptors=78% were detectable upon agonist stimulation with maximal signals >500 fluorescence units (Table 7). The detection rate was identical to that obtained previously with $cG\alpha_{q/z5}$ or $cG\alpha_{q/z9}$ alone, except that the two chimerae together favored detection of the $G\alpha_s$-coupling receptor, human GLP-1. The use of multiple chimerae therefore represents an alternative method for screening various receptor types ($G\alpha_{i/Go}$-, $G\alpha_s$-, and $G\alpha_q$-coupled) in a single assay format.

TABLE 7

Chimerae $cG\alpha_{q/z9}$ and $cG\alpha_{q/s9}$ and GPCRs in COS-7 cells: agonist-induced responses. Two µg $cG\alpha_{q/z9}$, 2 µg $cG\alpha_{q/s9}$, and 16 µg GPCR cDNA were transfected into COS-7 cells. Transfected cells were monitored for calcium mobilization in the FLIPR ™ using the calcium sensitive dye Fluo-3. Maximum agonist concentrations were 100 µM for non-peptide ligands or 10 µM for peptide ligands, except for neurotensin (1 µM). Fluorescence data represent the mean from 2 or more experiments. h = human; m = mouse; r = rat; adr = adrenergic; DA = dopamine; GLP-1 = glucagon-like peptide; 5HT = serotonin; GAL = galanin; NE = norepinephrine; MCH = melanin-concentrating hormone; NPY = neuropeptide Y; PP = pancreatic polypeptide; NPFF = neuropeptide FF; and NT = neurotensin

| # | RECEPTOR | PROPOSED COUPLING | AGONIST | MAXIMAL SIGNAL (FLUORESCENCE UNITS) $cG\alpha_{q/z9} + cG\alpha_{q/s9}$ |
|---|---|---|---|---|
| 1 | h D3 | $G\alpha_{i/o}$ | DA | 208 |
| 2 | h GLP-1 | $G\alpha_s$ | GLP-1 | 794 |
| 3 | h 5HT7 | $G\alpha_s$ | 5HT | 292 |
| 4 | h 5HT1E | $G\alpha_{i/o}$ | 5HT | 2 |
| 5 | h 5HT1F | $G\alpha_{i/o}$ | 5HT | 247 |
| 6 | m 5HT5B | $G\alpha_{i/o}$ | 5HT | 0 |
| 7 | m 5HT5A | $G\alpha_{i/o}$ | 5HT | 45 |
| 8 | h 5HT1D | $G\alpha_{i/o}$ | 5HT | 433 |
| 9 | h D5 | $G\alpha_s$, $G\alpha_{i/o}$ | DA | 1172 |
| 10 | h 5HT1B | $G\alpha_{i/o}$ | 5HT | 190 |
| 11 | h 5HT4 | $G\alpha_s$, $G\alpha_q$ | 5HT | 2345 |
| 12 | h 5HT6 | $G\alpha_s$ | 5HT | 1598 |
| 13 | h GALR3 | $G\alpha_{i/o}$ | GAL | 853 |
| 14 | h β2 adr | $G\alpha_s$, $G\alpha_{i/o}$ | NE | 2346 |
| 15 | h 5HT1A | $G\alpha_{i/o}$ | 5HT | 2161 |
| 16 | r GALR3 | $G\alpha_{i/o}$ | GAL | 1402 |
| 17 | h MCH | $G\alpha_q$ | MCH | 4808 |
| 18 | r GALR1 | $G\alpha_{i/o}$ | GAL | 1544 |
| 19 | r Y4 | $G\alpha_{i/o}$ | PP | 1015 |
| 20 | h α2C adr | $G\alpha_{i/o}$ | NE | 2341 |

TABLE 7-continued

Chimerae cGα$_{q/z9}$ and cGα$_{q/s9}$ and GPCRs in COS-7 cells: agonist-induced responses. Two μg cGα$_{q/z9}$, 2 μg cGα$_{q/s9}$, and 16 μg GPCR cDNA were transfected into COS-7 cells. Transfected cells were monitored for calcium mobilization in the FLIPR ™ using the calcium sensitive dye Fluo-3. Maximum agonist concentrations were 100 μM for non-peptide ligands or 10 μM for peptide ligands, except for neurotensin (1 μM). Fluorescence data represent the mean from 2 or more experiments.
h = human; m = mouse; r = rat; adr = adrenergic; DA = dopamine; GLP-1 = glucagon-like peptide; 5HT = serotonin; GAL = galanin; NE = norepinephrine; MCH = melanin-concentrating hormone; NPY = neuropeptide Y; PP = pancreatic polypeptide; NPFF = neuropeptide FF; and NT = neurotensin

| # | RECEPTOR | PROPOSED COUPLING | AGONIST | MAXIMAL SIGNAL (FLUORESCENCE UNITS) cGα$_{q/z9}$ + cGα$_{q/s9}$ |
|---|---|---|---|---|
| 21 | r GALR2 | Gα$_q$ | GAL | 2665 |
| 22 | h α2B adr | Gα$_{i/o}$ | NE | 4855 |
| 23 | h Y5 | Gα$_{i/o}$ | NPY | 982 |
| 24 | h GALR2 | Gα$_q$ | GAL | 4630 |
| 25 | h kappa | Gα$_{i/o}$ | U-69593 | 3529 |
| 26 | h NPFF1 | Gα$_{i/o}$ | NPFF | 793 |
| 27 | h NPFF2 | Gα$_{i/o}$ | NPFF | 158.2 |
| 28 | h α2A adr | Gα$_{i/o}$ | NE | 5284 |
| 29 | h D2 | Gα$_{i/o}$ | DA | 5549 |
| 30 | h GALR1 | Gα$_{i/o}$ | GAL | 8097 |
| 31 | h Y2 | Gα$_{i/o}$ | NPY | 3329 |
| 32 | h Y1 | Gα$_{i/o}$ | NPY | 2333 |
| 33 | h Y4 | Gα$_{i/o}$ | PP | 4133 |
| 34 | h α1A adr | Gα$_q$ | NE | 7585 |
| 35 | h D1 | Gα$_s$, Gα$_{i/o}$ | DA | 13516 |
| 36 | r NTR1 | Gα$_{aq}$ | NT | 4264 |

Summary of the Results

This work describes a functional assay with which various types and large numbers of GPCRs can be detected. The method is based on the premise that Gα proteins are derived from a common ancestor, and that the further a Gα protein is evolutionarily from the ancestral sequence, the more likely it is to contain motifs which restrict interactions to a subset of GPCRS. Conversely, sequences from more primitive organisms such as invertebrates may lack the restrictive motifs. Focusing specifically on Gα$_q$, we performed an amino acid sequence alignment of all known protein structures and identified distinct motifs, which differentiate vertebrate from invertebrate species (FIG. 5). For example, invertebrates lack the 6 amino acid N-terminal extension proposed to restrict GPCR interaction (Kostenis et al., 1998), and also contain Glu$^{18}$-Lys$^{19}$ instead of the vertebrate Ala$^{18}$-Arg$^{19}$ in a region of Gα$_q$ associated with receptor recognition (Lambright et al., 1996). These structural differences led us to speculate that an invertebrate Gα$_q$ backbone might function differently in a Gα$_q$ chimeric construct than would a vertebrate homologue, and that this difference might be expressed as an increase in GPCR/chimera promiscuity.

This hypothesis was tested using the invertebrate C. elegans as the source of the Gα$_q$ backbone, combined with C-terminal mammalian Gα tails 5, 9 or 21 amino acids in length. cGα$_{q/z5}$ was more promiscuous than any previously described Gα construct, supporting receptor activation when co-transfected into Xenopus oocytes or mammalian COS-7 cells with most Gα$_{i/o}$-, Gα$_s$, and Gα$_q$-coupling receptors. This result was unexpected, and contrasts with the prevailing expectations of experts in the field (Milligan and Rees, 1999). Indeed, the current data (Conklin et al., 1993, 1996; Milligan and Rees, 1999) support the idea that each G protein chimera is only capable of functional interaction with a limited range of receptors. If true, this perceived limitation would necessitate the assay of each GPCR against a panel of chimeric G proteins in order to identify an effective GPCR/G protein combination. The results indicate that certain chimeras, such as cGα$_{q/z5}$, are able to effectively couple to a very wide number of GPCRs, thus eliminating the need for such multiple assays.

C. elegans Gα$_{q/z5}$ may be used alone or combined with a second chimera such as cGα$_{q/s9}$ to further increase the detection rate especially for Gα$_s$-coupled receptors.

Conserved motifs within invertebrate Gα$_q$ subunits predict enhanced promiscuity from the use of any invertebrate Gα$_q$ backbone, including, but not limited to, the known Gα$_q$ sequences listed in Table 8. To provide experimental evidence for this we cloned and expressed a D. melanogaster chimera (dGα$_{q/z5}$; FIG. 2) containing the five C-terminal amino acids of human Gα$_z$. A comparison of cGα$_{q/z5}$, dGα$_{q/z5}$ and hGα$_{q/z5}$ revealed that the two invertebrate chimerae show a similar enhanced coupling to D1 receptors as compared to the corresponding human chimera (Table 9). These data strongly argue against the possibility that C. elegans Gα$_q$ is somehow unique in its ability to couple promiscuously. Rather, the D. melanogaster data suggest that many, if not all, invertebrate Gα$_q$ genes may provide a similarly enhanced utility to couple to a wide variety of GPCRs.

The general utility of employing Gα subunits from primitive organisms may be extended to include non-Gα$_q$ subunits from organisms outside of the animal kingdom, including for example, members of the genus Dictyostelium. The G-protein α subunits of Dictyostelium discoideum do not readily fall into those classes defined for members of the animal kingdom (Wilkie and Yokoyama, 1994), however, individual Gα subunits such as G alpha 2 have been shown to directly activate the PLC pathway (Okaichi et al., 1992). Other Gα subunits of Dictyostelium, such as G alpha 4, may also be useful based on their homology to member of the Gα$_q$ family. For example, G alpha 4 exhibits a greater homology to C. elegans Gα$_q$ than does G alpha 2 (47% vs. 42% at the amino acid level). Therefore, it is anticipated that Gα subunits from Dictyostelium, with or without amino acid substitutions within the protein, may be useful for functional assays for GPCRs. Therefore, for the purposes of this invention, the term invertebrate Gα$_q$ G protein includes Dictyostelium G alpha 2 (Gα$_2$) and G alpha 4 (Gα$_4$) G proteins.

Further enhancements to the coupling scope of the chimeric G proteins described in this invention may be realized by making select point mutations within regions of the protein known to contact GPCRs. For example, amino acids within the alpha4 helical domain of Gα$_{i1}$ are important for permitting a productive coupling to the 5HT1B receptor (Bae et al., 1999). Mutations altering two amino acids in this domain, Q304 and E308, specifically prevent coupling to 5HT1B. The majority of receptors that did not couple productively to the chimeric G proteins described herein include several members of the 5HT1 subfamily, including 5HT1B. It is predicted, therefore, based on the work of Bae et al. (1999) that making homologous amino acid substitutions in the alpha4 region of cGα$_q$ would extend the number of GPCRs that can functionally couple to chimeras, composed of cGα$_q$.

TABLE 8

Description of Gα$_q$ subunits from invertebrates useful for construction of chimeras.

| SPECIES | COMMON NAME | DESIGNATION | GENBANK ACCESSION NUMBER |
|---|---|---|---|
| *Drosophila melanogaster* | Fruit fly | GBQ1_drome | P23625 |
| *Drosophila melanogaster* | Fruit fly | GBQ3_drome | P54400 |
| *Limulus polyphemus* | Horseshoe crab | GBQ_limpo | g1857923 |
| *Patinopecten yessoensis* | Scallop | GBQ_patye | O15975 |
| *Loligo forbesi* | Squid | GBQ_lolfo | P38412 |
| *Homarus americanus* | Lobster | GBQ_homam | P91950 |
| *Lymnaea stagnalis* | Pond snail | GBQ_lymst | P38411 |
| *Geodia cydonium* | Sponge | GBQ_geocy | Y14248 |
| *Caenorhabditis elegans* | Nematode | GBQ_caeel | AF003739 |

TABLE 9

Comparison of invertebrate chimerae dGα$_{q/z5}$ and cGα$_{q/z5}$ with two different human hGα$_{q/z5}$ chimerae in their ability to couple to human D1 receptors in COS-7 cells. Ten μg chimera cDNA and 10 μg of human D1 receptor cDNA were transfected into COS-7 cells. Transfected cells were monitored for calcium mobilization in the FLIPR ™ using the calcium sensitive dye Fluo-3. Maximum agonist concentration was 100 μM dopamine. Fluorescent data represent the mean from two experiments.
MAXIMAL SIGNAL (FLUORESCENCE UNITS)

| dGα$_{q/z5}$ | cGα$_{q/z5}$ | hGα$_{q/z5}$* | hGα$_{q/z5}$† |
|---|---|---|---|
| 2149 | 4832 | 0 | 0 |

*Identical to Accession number L76256.
†Ala → Ser substitution at position 171.

This invention provides a powerful and rapid system for detecting GPCR activation that is obtained when an invertebrate-based Gα$_q$ chimera is coupled to a signal amenable to high throughput screening, such as fluorescence-based detection of calcium mobilization. Specific applications would include: 1) high throughput screening and pharmacological analysis of a known GPCR, e.g., drug discovery; 2) screening of ligands against a cloned orphan receptor whose signaling pathways are unknown; and 3) screening of a cDNA library against one or more ligands in an expression cloning paradigm. In each case, this method supports detection of GPCRs from various classes (Gα$_{i/o}$, Gα$_s$, and Gα$_q$-coupling) in a single assay format with greater efficiency and capture rate than previously described methods.

REFERENCES

Bae, H., Cabrera-Vera, T. M., Depree, K. M., et al. "Two amino acids within the alpha4 helix of Galphai1 mediate coupling with 5-hydroxytryptamine1B receptors" *J. Biol. Chem.* 274: 14963–14971 (1999).

Barnes, R. D. "Invertebrate Zoology" W.B. Saunders Company, Philadelphia, p. 1 (1974).

Bourne, H. R. "How receptors talk to trimeric G proteins" *Curr. Opin. Cell Biol.* 9: 134–142 (1997).

Bradford, M. M. "A rapid and sensitive method for the quantitation of microgram quantities of protein utilizing the principle of protein-dye binding" *Anal. Biochem.* 72: 248–254 (1976).

Burgevin, M.-C., Loquet, I., Quarteronet, D., Habert-Ortoli, E. "Cloning, pharmacological characterization, and anatomical distribution of a rat cDNA encoding for a galanin receptor" *J. Molec. Neurosci.* 6: 33–41 (1995).

Bush, A. B., et al. "Nerve growth factor potentiates bradykinin-induced calcium influx and release in PC12 cells" *J. Neurochem.* 57: 562–574 (1991).

The *C. elegans* Sequencing Consortium. "Genome sequence of the nematode *C. elegans*: a platform for investigating biology" *Science* 282: 2012–2018 (1998).

Conklin, B. R., et al. "Substitution of three amino acids switches receptor specificity of Gq alpha to that of Gi alpha" *Nature* 363: 274–276 (1993).

Conklin, B. R., Herzmark, P., Ishida, S., et al. "Carboxyl-terminal mutations of Gq alpha and Gs alpha that alter the fidelity of receptor activation" *Mol. Pharmacol.* 50: 885–890 (1996).

Cullen, B. R. "Use of eukaryotic expression technology in the functional analysis of cloned genes" *Methods Enzymol.* 152:684–704 (1987).

Dascal, N., et al. "Atrial G protein-activated K$^+$ channel: expression cloning and molecular properties" *Proc. Natl. Acad. Sci. USA* 90:10235–10239 (1993).

Dillon, J. S., Tanizawa, Y., Wheeler, M. B., et al. "Cloning and functional expression of the human glucagon-like peptide-1 (GLP-1) receptor" *Endocrinology* 133: 1907–1910 (1993).

Dixon, R. A., Kobilka, B. K., Strader, D. J., et al. "Cloning of the gene and cDNA for mammalian beta-adrenergic receptor and homology with rhodopsin" *Nature* 321: 75–79 (1986).

Eva, C., Keinanen, K., Monyer, H., Seeburg, P., Sprengel, R. "Molecular cloning of a novel G protein-coupled receptor that may belong to the neuropeptide receptor family" 271: 80–84 (1990).

Gundersen, C. B., et al. "Serotonin receptors induced by exogenous messenger RNA in *Xenopus* oocytes" *Proc. R. Soc. Lond. B. Biol. Sci.* 219(1214): 103–109 (1983).

Habert-Ortoli, E., Amiranoff, B., Loquet, I., Laburthe, M., and Mayaux, J.-F. "Molecular cloning of a functional human galanin receptor" *Proc. Natl. Acad. Sci. USA* 91: 9780–9783 (1994).

Harwood, G., Lockyer, M., Giles, H., Fairweather, N. "Cloning and characterisation of the rabbit 5-HT1D alpha and 5-HT1D beta receptors" *FEBS Lett.* 377: 73–76 (1995).

Inanobe, A., et al. "Characterization of G protein-gated K$^+$ channels composed of Kir3.2 subunits in dopaminergic neurons of the substantia nigra" *J. Neurosci.* 19:1006–1017 (1999).

Jansen, G., Thijssen, K. L., Werner, P., van der Horst, M., Hazendonk, E. & Plasterk, R. H. "The complete family of genes encoding G proteins of *Caenorhabditis elegans*" *Nat. Genet.* 21: 414–419 (1999).

Julius, D., MacDermott, A. B., Axel, R., Jessell, T. M. "Molecular characterization of a functional cDNA encoding the serotonin 1c receptor" *Science* 241: 558–564 (1988).

Keeton, W. T. "Biological Science" W.W. Norton & Co., New York, p. 1017 (1980).

Kieffer, B., Befort, K., Gaveriaux-Ruff, C., Hirth, C. G. "The δ-opioid receptor: Isolation of a cDNA by expression cloning and pharmacological characterization" *Proc. Natl. Acad. Sci. USA* 89: 12048–12052 (1992).

Kluxen, F. W., Bruns, C., Lubbert, H. "Expression cloning of a rat brain somatostatin receptor cDNA" *Proc. Natl. Acad. Sci. USA* 89: 4618–4622 (1992).

Kobilka, B. K., Frielle, T., Collins, S., et al. "An intronless gene encoding a potential member of the family of receptors coupled to guanine nucleotide regulatory proteins" *Nature* 329: 75–79 (1987).

Kohen, R., Metcalf, M. A., Khan, N., Druck, T., Huebner, K., Lachowicz, J. E., Meltzer, H. Y., Sibley, D. R., Roth, B. L., Hamblin, M. W. "Cloning, characterization, and chromosomal localization of a human 5-HT6 serotonin receptor" *J. Neurochem.* 66: 47–56 (1996).

Kostenis, E., Degtyarev, M. Y., Conklin, B. R., Wess, J. "The N-terminal extension of Galphaq is critical for constraining the selectivity of receptor coupling" *J. Biol. Chem.* 272: 19107–19110 (1997).

Kostenis, E., Zeng, F. Y., Wess, J. "Functional characterization of a series of mutant G protein alphaq subunits displaying promiscuous receptor coupling properties" *J Biol. Chem.* 273: 17886–17892 (1998).

Krapivinsky, G., et al. "The cardiac inward rectifier $K^+$ channel subunit, CIR, does not comprise the ATP-sensitive $K^+$ channel, IKATP" *J. Biol. Chem.* 270:28777–28779 (1995b).

Krapivinsky, G., et al., "The G protein-gated atrial $K^+$ channel IKACh is a heteromultimer of two inwardly rectifying K(+)-channel proteins" *Nature* 374:135–141 (1995).

Kubo, Y., et al. "Primary structure and functional expression of a rat G protein-coupled muscarinic potassium channel" *Nature* 364:802–806 (1993).

Lambright, D. G., Sondek, J., Bohm, A., Skiba, N. P., Hamm, H. E. & Sigler, P. B. "The 2.0 A crystal structure of a heterotrimeric G protein" *Nature* 379: 311–319 (1996).

Larhammar, D., Blomqvist, A. G., Yee, F., Jazin, E., Yoo, H., Wahlestedt, C. R. "Cloning and functional expression of a human neuropeptide Y/peptide YY receptor of the Y1 type" *J. Biol. Chem.* 267: 10935–10938 (1992).

Lazareno, S. and Birdsall, N. J. M. "Pharmacological characterization of acetylcholine stimulated [$^{35}$S]-GTPγS binding mediated by human muscarinic m1–m4 receptors: antagonist studies" *Br. J. Pharmacol.* 109: 1120–1127 (1993).

Mansson, E., Bare, L., Yang, D. "Isolation of a human kappa opioid receptor cDNA from placenta" *Biochem Biophys Res Commun.* 202: 1431–1437 (1994).

Matthes, H., Boschert, U., Amlaiky, N., Grailhe, R., Plassat, J. L., Muscatelli, F., Mattei, M. G., Hen, R. "Mouse 5-hydroxytryptamine5A and 5-hydroxytryptamine5B receptors define a new family of serotonin receptors: cloning, functional expression, and chromosomal localization" *Mol. Pharmacol.* 43: 313–319 (1993).

Milligan, G. and Rees, S. "Chimeric Gα proteins: their potential use in drug discovery" *Trends Pharmacol. Sci.* 20: 118–124 (1999).

Naylor, L. H. "Reporter gene technology: the future looks bright" *Biochem. Pharmacol.* 58(5): 749–757 (1999).

Offermans, S. and Simon, M. I. "$G\alpha_{15}$ and $G\alpha_{16}$ couple a wide variety of receptors to phospholipase C" *J. Biol. Chem.* 270: 15175–15180 (1995).

Okaichi, K., Cubitt, A. B., Pitt, G. S. and Firtel, R. A. "Amino acid substitutions in the *Dictyostelium* G alpha subunit G alpha 2 produce dominant negative phenotypes and inhibit the activation of adenylyl cyclase, guanylyl cyclase, and phospholipase C" *Mol Biol Cell* 3: 735–747 (1992).

Plassat, J. L., Boschert, U., Amlaiky, N., Hen, R. "The mouse 5HT5 receptor reveals a remarkable heterogeneity within the 5HT1D receptor family" *EMBO J.* 11: 4779–4786 (1992).

Quick, M. W. and Lester, H. A. "Methods for expression of excitability proteins in *Xenopus* oocytes" *Meth. Neurosci.* 19: 261–279 (1994).

Salon, J. A. and Owicki, J. A., "Real-time measurements of receptor activity: Application of microphysiometric techniques to receptor biology" *Methods in Neuroscience* 25: pp. 201–224, Academic Press (1996).

Seack, J., Kruse, M. & Muller, W. E. "Evolutionary analysis of G proteins in early metazoans: cloning of alpha- and beta-subunits from the sponge *Geodia cydonium*." *Biochim. Biophys Acta"*, 1401: 93–103 (1998).

Sidhu, A. et al. "D1 dopamine receptors can interact with both stimulatory and inhibitory guanine nucleotide binding proteins" *J. Neurochem.* 57: 1445–1451 (1991).

Simon, M. I., Strathmann, M. P., Gautam, N. "Diversity of G proteins in signal transduction" *Science* 252: 802–808 (1991).

Smith, K. E., et al. "Expression cloning of a rat hypothalamic galanin receptor coupled to phosphoinositide turnover" *J. Biol. Chem.* 272: 24612–24616 (1997).

Suga, H., Koyanagi, M., Hoshiyama, D., Ono, K., Iwabe, N., Kuma, K., Miyata, T. "Extensive gene duplication in the early evolution of animals before the parazoan-eumetazoan split demonstrated by G proteins and protein tyrosine kinases from sponge and hydra" *J. Mol. Evol.* 48: 646–653 (1999).

Sunahara, R. K., Dessauer, C. W., and Gilman, A. G. "Complexity and diversity of mammalian adenylyl cyclases" *Ann. Rev. Pharm. Tox.* 36: 461–480 (1996).

Takahashi, T., et al. "Rat brain serotonin receptors in *Xenopus* oocytes are coupled by intracellular calcium to endogenous channels" *Proc. Natl. Acad. Sci. USA* 84: 5063–5067 (1987).

Tanaka, K., Masu, M., Nakanishi, S. "Structure and functional expression of the cloned rat neurotensin receptor" *Neuron* 4: 847–854 (1990).

Tian, W., et al. "Determinants of alpha-Adrenergic Receptor Activation of G protein: Evidence for a Precoupled Receptor/G protein State" *Mol. Pharmacol.* 45: 524–553 (1994).

Watling, K. J. "The RBI Handbook of Receptor Classification and Signal Transduction" Sigma-Aldrich Research Biochemicals Inc., Natick, Mass. (1998).

What is claimed is:

1. An isolated nucleic acid encoding a chimeric G protein, wherein the chimeric G protein comprises a *Caenorhabditis elegans* Gαq G protein having the amino acid sequence set forth in SEQ ID NO: 1; provided that upon activation the chimeric G protein produces a Gαq second messenger response and wherein the Gαq second messenger response comprises release of intracellular calcium or calcium mobilization.

2. An isolated nucleic acid encoding a chimeric G protein, wherein the chimeric G protein comprises a *Caenorhabditis elegans* Gαq G protein having the amino acid sequence set forth in SEQ ID NO: 2; provided that upon activation the chimeric G protein produces a Gαq second messenger response and wherein the Gαq second messenger response comprises release of intracellular calcium or calcium mobilization.

3. An isolated nucleic acid encoding a chimeric G protein, wherein the chimeric G protein comprises a *Caenorhabditis elegans* Gαq G protein having the amino acid sequence set forth in SEQ ID NO: 3; provided that upon activation the chimeric G protein produces a Gαq second messenger response and wherein the Gαq second messenger response comprises release of intracellular calcium or calcium mobilization.

4. An isolated nucleic acid encoding a chimeric G protein, wherein the chimeric G protein comprises a *Caenorhabditis elegans* Gαq G protein having the amino acid sequence set forth in SEQ ID NO: 4; provided that upon activation the chimeric G protein produces a Gαq second messenger response and wherein the Gαq second messenger response comprises release of intracellular calcium or calcium mobilization.

5. An isolated nucleic acid encoding a chimeric G protein, wherein the chimeric G protein comprises a *Caenorhabditis elegans* Gαq G protein having the amino acid sequence set forth in SEQ ID NO: 5; provided that upon activation the chimeric G protein produces a Gαq second messenger response and wherein the Gαq second messenger response comprises release of intracellular calcium or calcium mobilization.

6. An isolated nucleic acid encoding a chimeric G protein, wherein the chimeric G protein comprises a *Drosophila melanogaster* Gαq G protein having the amino acid sequence set forth in SEQ ID NO: 41; provided that upon activation the chimeric G protein produces a Gαq second messenger response and wherein the Gαq second messenger response comprises release of intracellular calcium or calcium mobilization.

* * * * *

SEQUENCE LISTING

```
<160> NUMBER OF SEQ ID NOS: 45

<210> SEQ ID NO 1
<211> LENGTH: 355
<212> TYPE: PRT
<213> ORGANISM: C. elegans
```

<400> SEQUENCE: 1

```
Met Ala Cys Cys Leu Ser Glu Glu Ala Arg Glu Gln Lys Arg Ile Asn
 1               5                  10                  15

Gln Glu Ile Glu Lys Gln Leu Gln Arg Asp Lys Arg Asn Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Gln Gly Tyr Ser Glu Glu
 50                  55                  60

Asp Lys Arg Ala His Ile Arg Leu Val Tyr Gln Asn Val Phe Met Ala
 65                  70                  75                  80

Ile Gln Ser Met Ile Arg Ala Met Asp Thr Leu Asp Ile Lys Phe Gly
                 85                  90                  95

Asn Glu Ser Glu Glu Leu Gln Glu Lys Ala Ala Val Val Arg Glu Val
                100                 105                 110

Asp Phe Glu Ser Val Thr Ser Phe Glu Glu Pro Tyr Val Ser Tyr Ile
            115                 120                 125

Lys Glu Leu Trp Glu Asp Ser Gly Ile Gln Glu Cys Tyr Asp Arg Arg
        130                 135                 140

Arg Glu Tyr Gln Leu Thr Asp Ser Ala Lys Tyr Tyr Leu Ser Asp Leu
145                 150                 155                 160

Arg Arg Leu Ala Val Pro Asp Tyr Leu Pro Thr Glu Gln Asp Ile Leu
                165                 170                 175

Arg Val Arg Val Pro Thr Thr Gly Ile Ile Glu Tyr Pro Phe Asp Leu
            180                 185                 190

Glu Gln Ile Ile Phe Arg Met Val Asp Val Gly Gly Gln Arg Ser Glu
        195                 200                 205

Arg Arg Lys Trp Ile His Cys Phe Glu Asn Val Thr Ser Ile Met Phe
210                 215                 220

Leu Val Ala Leu Ser Glu Tyr Asp Gln Val Leu Val Glu Cys Asp Asn
225                 230                 235                 240

Glu Asn Arg Met Glu Glu Ser Lys Ala Leu Phe Arg Thr Ile Ile Thr
                245                 250                 255

Tyr Pro Trp Phe Thr Asn Ser Ser Val Ile Leu Phe Leu Asn Lys Lys
            260                 265                 270

Asp Leu Leu Glu Glu Lys Ile Leu Tyr Ser His Leu Ala Asp Tyr Phe
        275                 280                 285

Pro Glu Tyr Asp Gly Pro Pro Arg Asp Pro Ile Ala Ala Arg Glu Phe
    290                 295                 300

Ile Leu Lys Met Phe Val Asp Leu Asn Pro Asp Ala Asp Lys Ile Ile
305                 310                 315                 320

Tyr Ser His Phe Thr Cys Ala Thr Asp Thr Glu Asn Ile Arg Phe Val
                325                 330                 335

Phe Ala Ala Val Lys Asp Thr Ile Leu Gln His Asn Leu Lys Tyr Ile
            340                 345                 350

Gly Leu Cys
        355
```

<210> SEQ ID NO 2
<211> LENGTH: 355
<212> TYPE: PRT
<213> ORGANISM: C. elegans

```
<400> SEQUENCE: 2

Met Ala Cys Cys Leu Ser Glu Glu Ala Arg Glu Gln Lys Arg Ile Asn
 1               5                  10                  15

Gln Glu Ile Glu Lys Gln Leu Gln Arg Asp Lys Arg Asn Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Gln Gly Tyr Ser Glu Glu
         50                  55                  60

Asp Lys Arg Ala His Ile Arg Leu Val Tyr Gln Asn Val Phe Met Ala
 65                  70                  75                  80

Ile Gln Ser Met Ile Arg Ala Met Asp Thr Leu Asp Ile Lys Phe Gly
                 85                  90                  95

Asn Glu Ser Glu Glu Leu Gln Glu Lys Ala Ala Val Val Arg Glu Val
                100                 105                 110

Asp Phe Glu Ser Val Thr Ser Phe Glu Glu Pro Tyr Val Ser Tyr Ile
            115                 120                 125

Lys Glu Leu Trp Glu Asp Ser Gly Ile Gln Glu Cys Tyr Asp Arg Arg
130                 135                 140

Arg Glu Tyr Gln Leu Thr Asp Ser Ala Lys Tyr Tyr Leu Ser Asp Leu
145                 150                 155                 160

Arg Arg Leu Ala Val Pro Asp Tyr Leu Pro Thr Glu Gln Asp Ile Leu
                165                 170                 175

Arg Val Arg Val Pro Thr Thr Gly Ile Ile Glu Tyr Pro Phe Asp Leu
                180                 185                 190

Glu Gln Ile Ile Phe Arg Met Val Asp Val Gly Gly Gln Arg Ser Glu
            195                 200                 205

Arg Arg Lys Trp Ile His Cys Phe Glu Asn Val Thr Ser Ile Met Phe
210                 215                 220

Leu Val Ala Leu Ser Glu Tyr Asp Gln Val Leu Val Glu Cys Asp Asn
225                 230                 235                 240

Glu Asn Arg Met Glu Glu Ser Lys Ala Leu Phe Arg Thr Ile Ile Thr
                245                 250                 255

Tyr Pro Trp Phe Thr Asn Ser Ser Val Ile Leu Phe Leu Asn Lys Lys
                260                 265                 270

Asp Leu Leu Glu Glu Lys Ile Leu Tyr Ser His Leu Ala Asp Tyr Phe
            275                 280                 285

Pro Glu Tyr Asp Gly Pro Pro Arg Asp Pro Ile Ala Ala Arg Glu Phe
290                 295                 300

Ile Leu Lys Met Phe Val Asp Leu Asn Pro Asp Ala Asp Lys Ile Ile
305                 310                 315                 320

Tyr Ser His Phe Thr Cys Ala Thr Asp Thr Glu Asn Ile Arg Phe Val
                325                 330                 335

Phe Ala Ala Val Lys Asp Thr Ile Leu Gln Asn Asn Leu Lys Tyr Ile
            340                 345                 350

Gly Leu Cys
        355

<210> SEQ ID NO 3
<211> LENGTH: 355
<212> TYPE: PRT
<213> ORGANISM: C. elegans
```

```
<400> SEQUENCE: 3

Met Ala Cys Cys Leu Ser Glu Glu Ala Arg Glu Gln Lys Arg Ile Asn
 1               5                  10                  15

Gln Glu Ile Glu Lys Gln Leu Gln Arg Asp Lys Arg Asn Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Gln Gly Tyr Ser Glu Glu
     50                  55                  60

Asp Lys Arg Ala His Ile Arg Leu Val Tyr Gln Asn Val Phe Met Ala
 65                  70                  75                  80

Ile Gln Ser Met Ile Arg Ala Met Asp Thr Leu Asp Ile Lys Phe Gly
                 85                  90                  95

Asn Glu Ser Glu Glu Leu Gln Glu Lys Ala Ala Val Val Arg Glu Val
                100                 105                 110

Asp Phe Glu Ser Val Thr Ser Phe Glu Glu Pro Tyr Val Ser Tyr Ile
            115                 120                 125

Lys Glu Leu Trp Glu Asp Ser Gly Ile Gln Glu Cys Tyr Asp Arg Arg
        130                 135                 140

Arg Glu Tyr Gln Leu Thr Asp Ser Ala Lys Tyr Tyr Leu Ser Asp Leu
145                 150                 155                 160

Arg Arg Leu Ala Val Pro Asp Tyr Leu Pro Thr Glu Gln Asp Ile Leu
                165                 170                 175

Arg Val Arg Val Pro Thr Thr Gly Ile Ile Glu Tyr Pro Phe Asp Leu
            180                 185                 190

Glu Gln Ile Ile Phe Arg Met Val Asp Val Gly Gly Gln Arg Ser Glu
        195                 200                 205

Arg Arg Lys Trp Ile His Cys Phe Glu Asn Val Thr Ser Ile Met Phe
210                 215                 220

Leu Val Ala Leu Ser Glu Tyr Asp Gln Val Leu Val Glu Cys Asp Asn
225                 230                 235                 240

Glu Asn Arg Met Glu Glu Ser Lys Ala Leu Phe Arg Thr Ile Ile Thr
                245                 250                 255

Tyr Pro Trp Phe Thr Asn Ser Ser Val Ile Leu Phe Leu Asn Lys Lys
            260                 265                 270

Asp Leu Leu Glu Glu Lys Ile Leu Tyr Ser His Leu Ala Asp Tyr Phe
        275                 280                 285

Pro Glu Tyr Asp Gly Pro Pro Arg Asp Pro Ile Ala Ala Arg Glu Phe
    290                 295                 300

Ile Leu Lys Met Phe Val Asp Leu Asn Pro Asp Ala Asp Lys Ile Ile
305                 310                 315                 320

Tyr Ser His Phe Thr Cys Ala Thr Asp Thr Glu Asn Ile Arg Phe Val
                325                 330                 335

Phe Ala Ala Val Lys Asp Thr Ile Leu Gln Met His Leu Arg Gln Tyr
            340                 345                 350

Glu Leu Leu
        355

<210> SEQ ID NO 4
<211> LENGTH: 355
<212> TYPE: PRT
<213> ORGANISM: C. elegans
```

<400> SEQUENCE: 4

```
Met Ala Cys Cys Leu Ser Glu Glu Ala Arg Glu Gln Lys Arg Ile Asn
 1               5                   10                  15

Gln Glu Ile Glu Lys Gln Leu Gln Arg Asp Lys Arg Asn Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Gln Gly Tyr Ser Glu Glu
 50                  55                  60

Asp Lys Arg Ala His Ile Arg Leu Val Tyr Gln Asn Val Phe Met Ala
 65                  70                  75                  80

Ile Gln Ser Met Ile Arg Ala Met Asp Thr Leu Asp Ile Lys Phe Gly
                 85                  90                  95

Asn Glu Ser Glu Glu Leu Gln Glu Lys Ala Ala Val Val Arg Glu Val
                100                 105                 110

Asp Phe Glu Ser Val Thr Ser Phe Glu Glu Pro Tyr Val Ser Tyr Ile
            115                 120                 125

Lys Glu Leu Trp Glu Asp Ser Gly Ile Gln Glu Cys Tyr Asp Arg Arg
130                 135                 140

Arg Glu Tyr Gln Leu Thr Asp Ser Ala Lys Tyr Tyr Leu Ser Asp Leu
145                 150                 155                 160

Arg Arg Leu Ala Val Pro Asp Tyr Leu Pro Thr Glu Gln Asp Ile Leu
                165                 170                 175

Arg Val Arg Val Pro Thr Thr Gly Ile Ile Glu Tyr Pro Phe Asp Leu
                180                 185                 190

Glu Gln Ile Ile Phe Arg Met Val Asp Val Gly Gly Gln Arg Ser Glu
            195                 200                 205

Arg Arg Lys Trp Ile His Cys Phe Glu Asn Val Thr Ser Ile Met Phe
210                 215                 220

Leu Val Ala Leu Ser Glu Tyr Asp Gln Val Leu Val Glu Cys Asp Asn
225                 230                 235                 240

Glu Asn Arg Met Glu Glu Ser Lys Ala Leu Phe Arg Thr Ile Ile Thr
                245                 250                 255

Tyr Pro Trp Phe Thr Asn Ser Ser Val Ile Leu Phe Leu Asn Lys Lys
                260                 265                 270

Asp Leu Leu Glu Glu Lys Ile Leu Tyr Ser His Leu Ala Asp Tyr Phe
            275                 280                 285

Pro Glu Tyr Asp Gly Pro Pro Arg Asp Pro Ile Ala Ala Arg Glu Phe
290                 295                 300

Ile Leu Lys Met Phe Val Asp Leu Asn Pro Asp Ala Asp Lys Ile Ile
305                 310                 315                 320

Tyr Ser His Phe Thr Cys Ala Thr Asp Thr Glu Asn Ile Arg Arg Val
                325                 330                 335

Phe Asn Asp Cys Arg Asp Ile Ile Gln Arg Met His Leu Arg Gln Tyr
            340                 345                 350

Glu Leu Leu
        355
```

<210> SEQ ID NO 5
<211> LENGTH: 355
<212> TYPE: PRT
<213> ORGANISM: C. elegans

```
<400> SEQUENCE: 5

Met Ala Cys Cys Leu Ser Glu Glu Ala Arg Glu Gln Lys Arg Ile Asn
  1               5                  10                  15

Gln Glu Ile Glu Lys Gln Leu Gln Arg Asp Lys Arg Asn Ala Arg Arg
                 20                  25                  30

Glu Leu Lys Leu Leu Leu Gly Thr Gly Glu Ser Gly Lys Ser Thr
             35                  40                  45

Phe Ile Lys Gln Met Arg Ile Ile His Gly Gln Gly Tyr Ser Glu Glu
             50                  55                  60

Asp Lys Arg Ala His Ile Arg Leu Val Tyr Gln Asn Val Phe Met Ala
 65                  70                  75                  80

Ile Gln Ser Met Ile Arg Ala Met Asp Thr Leu Asp Ile Lys Phe Gly
                 85                  90                  95

Asn Glu Ser Glu Glu Leu Gln Glu Lys Ala Ala Val Val Arg Glu Val
                100                 105                 110

Asp Phe Glu Ser Val Thr Ser Phe Glu Glu Pro Tyr Val Ser Tyr Ile
                115                 120                 125

Lys Glu Leu Trp Glu Asp Ser Gly Ile Gln Glu Cys Tyr Asp Arg Arg
            130                 135                 140

Arg Glu Tyr Gln Leu Thr Asp Ser Ala Lys Tyr Tyr Leu Ser Asp Leu
145                 150                 155                 160

Arg Arg Leu Ala Val Pro Asp Tyr Leu Pro Thr Glu Gln Asp Ile Leu
                165                 170                 175

Arg Val Arg Val Pro Thr Thr Gly Ile Ile Glu Tyr Pro Phe Asp Leu
            180                 185                 190

Glu Gln Ile Ile Phe Arg Met Val Asp Val Gly Gly Gln Arg Ser Glu
            195                 200                 205

Arg Arg Lys Trp Ile His Cys Phe Glu Asn Val Thr Ser Ile Met Phe
210                 215                 220

Leu Val Ala Leu Ser Glu Tyr Asp Gln Val Leu Val Glu Cys Asp Asn
225                 230                 235                 240

Glu Asn Arg Met Glu Glu Ser Lys Ala Leu Phe Arg Thr Ile Ile Thr
                245                 250                 255

Tyr Pro Trp Phe Thr Asn Ser Ser Val Ile Leu Phe Leu Asn Lys Lys
            260                 265                 270

Asp Leu Leu Glu Glu Lys Ile Leu Tyr Ser His Leu Ala Asp Tyr Phe
            275                 280                 285

Pro Glu Tyr Asp Gly Pro Pro Arg Asp Pro Ile Ala Ala Arg Glu Phe
290                 295                 300

Ile Leu Lys Met Phe Val Asp Leu Asn Pro Asp Ala Asp Lys Ile Ile
305                 310                 315                 320

Tyr Ser His Phe Thr Cys Ala Thr Asp Thr Glu Asn Ile Arg Phe Val
                325                 330                 335

Phe Ala Ala Val Lys Asp Thr Ile Leu Gln His Asn Leu Lys Glu Cys
                340                 345                 350

Gly Leu Tyr
        355

<210> SEQ ID NO 6
<211> LENGTH: 359
<212> TYPE: PRT
<213> ORGANISM: Homo sapiens
```

<400> SEQUENCE: 6

```
Met Thr Leu Glu Ser Ile Met Ala Cys Cys Leu Ser Glu Glu Ala Lys
 1               5                  10                  15

Glu Ala Arg Arg Ile Asn Asp Glu Ile Glu Arg Gln Leu Arg Arg Asp
                20                  25                  30

Lys Arg Asp Ala Arg Arg Glu Leu Lys Leu Leu Leu Leu Gly Thr Gly
            35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Ala Val
        355
```

<210> SEQ ID NO 7
<211> LENGTH: 359
<212> TYPE: PRT
<213> ORGANISM: Canis familiaris

```
<400> SEQUENCE: 7

Met Thr Leu Glu Ser Ile Met Ala Cys Cys Leu Ser Glu Glu Ala Lys
 1               5                  10                  15

Glu Ala Arg Arg Ile Asn Asp Glu Ile Glu Arg Gln Leu Arg Arg Asp
            20                  25                  30

Lys Arg Asp Ala Arg Glu Leu Lys Leu Leu Leu Leu Gly Thr Gly
        35                  40                  45

Glu Ser Gly Lys Ser Thr Phe Ile Lys Gln Met Arg Ile Ile His Gly
    50                  55                  60

Ser Gly Tyr Ser Asp Glu Asp Lys Arg Gly Phe Thr Lys Leu Val Tyr
65                  70                  75                  80

Gln Asn Ile Phe Thr Ala Met Gln Ala Met Ile Arg Ala Met Asp Thr
                85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355

<210> SEQ ID NO 8
<211> LENGTH: 359
<212> TYPE: PRT
<213> ORGANISM: Mus musculus
```

<400> SEQUENCE: 8

| | | | | | | | | | | | | | | |
|---|---|---|---|---|---|---|---|---|---|---|---|---|---|---|
|Met|Thr|Leu|Glu|Ser|Ile|Met|Ala|Cys|Cys|Leu|Ser|Glu|Glu|Ala|Lys|
|1| | | |5| | | | |10| | | | |15| |

Glu Ala Arg Arg Ile Asn Asp Glu Ile Glu Arg His Val Arg Arg Asp
          20               25               30

Lys Arg Asp Ala Arg Arg Glu Leu Lys Leu Leu Leu Gly Thr Gly
     35               40               45

Glu Ser Gly Lys Ser Thr Phe Ile Lys Gln Met Arg Ile Ile His Gly
 50               55              60

Ser Gly Tyr Ser Asp Glu Asp Lys Arg Gly Phe Thr Lys Leu Val Tyr
65             70             75             80

Gln Asn Ile Phe Thr Ala Met Gln Ala Met Ile Arg Ala Met Asp Thr
         85               90             95

Leu Lys Ile Pro Tyr Lys Tyr Glu His Asn Lys Ala His Ala Gln Leu
        100             105          110

Val Arg Glu Val Asp Val Glu Lys Val Ser Ala Phe Glu Asn Pro Tyr
    115             120          125

Val Asp Ala Ile Lys Ser Leu Trp Asn Asp Pro Gly Ile Gln Glu Cys
130           135          140

Tyr Asp Arg Arg Arg Glu Tyr Gln Leu Ser Asp Ser Thr Lys Tyr Tyr
145           150          155         160

Leu Asn Asp Leu Asp Arg Val Ala Asp Pro Ser Tyr Leu Pro Thr Gln
        165           170          175

Gln Asp Val Leu Arg Val Arg Val Pro Thr Thr Gly Ile Ile Glu Tyr
    180             185          190

Pro Phe Asp Leu Gln Ser Val Ile Phe Arg Met Val Asp Val Gly Gly
        195           200          205

Gln Arg Ser Glu Arg Arg Lys Trp Ile His Cys Phe Glu Asn Val Thr
210           215          220

Ser Ile Met Phe Leu Val Ala Leu Ser Glu Tyr Asp Gln Val Leu Val
225           230          235         240

Glu Ser Asp Asn Glu Asn Arg Met Glu Glu Ser Lys Ala Leu Phe Arg
        245           250          255

Thr Ile Ile Thr Tyr Pro Trp Phe Gln Asn Ser Ser Val Ile Leu Phe
    260             265          270

Leu Asn Lys Lys Asp Leu Leu Glu Glu Lys Ile Met Tyr Ser His Leu
        275           280          285

Val Asp Tyr Phe Pro Glu Tyr Asp Gly Pro Gln Arg Asp Ala Gln Ala
290           295          300

Ala Arg Glu Phe Ile Leu Lys Met Phe Val Asp Leu Asn Pro Asp Ser
305           310          315         320

Asp Lys Ile Ile Tyr Ser His Phe Thr Cys Ala Thr Asp Thr Glu Asn
        325           330          335

Ile Arg Phe Val Phe Ala Ala Val Lys Asp Thr Ile Leu Gln Leu Asn
    340             345          350

Leu Lys Glu Tyr Asn Leu Val
        355

<210> SEQ ID NO 9
<211> LENGTH: 359
<212> TYPE: PRT
<213> ORGANISM: Xenopus laevis

<400> SEQUENCE: 9

```
Met Thr Leu Glu Ser Ile Met Ala Cys Cys Leu Ser Glu Glu Ala Glu
 1               5                  10                  15

Glu Ala Arg Arg Ile Asn Asp Glu Ile Glu Arg Gln Leu Arg Arg Asp
             20                  25                  30

Lys Arg Asp Ala Arg Arg Glu Leu Lys Leu Leu Leu Gly Thr Gly
         35                  40                  45

Glu Ser Gly Lys Ser Thr Phe Ile Lys Gln Met Arg Ile Ile His Gly
 50                  55                  60

Ser Gly Tyr Ser Asp Glu Asp Lys Arg Gly Phe Thr Lys Leu Val Tyr
 65                  70                  75                  80

Gln Asn Ile Phe Ser Ala Met Gln Ala Met Ile Arg Ala Met Glu Thr
                 85                  90                  95

Leu Lys Ile Pro Tyr Lys Tyr Glu His Asn Lys Gly His Ala Leu Leu
             100                 105                 110

Val Arg Glu Val Asp Val Glu Lys Val Ala Ser Phe Glu Asn Pro Tyr
         115                 120                 125

Val Asp Ala Ile Lys Tyr Leu Trp Asn Asp Pro Gly Ile Gln Glu Cys
130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Ile Ala Thr His Gly Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
        195                 200                 205

Gln Arg Ser Glu Arg Arg Lys Trp Ile His Cys Phe Glu Asn Val Thr
    210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
            260                 265                 270

Leu Asn Lys Lys Asp Leu Leu Glu Glu Lys Ile Met Tyr Ser His Leu
        275                 280                 285

Val Asp Tyr Phe Pro Glu Tyr Asp Gly Pro Gln Arg Asp Ala Gln Ala
    290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
            340                 345                 350

Leu Lys Glu Tyr Asn Leu Val
        355
```

<210> SEQ ID NO 10
<211> LENGTH: 353
<212> TYPE: PRT
<213> ORGANISM: Patinopecten yessoensis

<400> SEQUENCE: 10

```
Met Ala Cys Cys Leu Ser Glu Glu Ala Lys Glu Gln Lys Arg Ile Asn
  1               5                  10                  15
Cys Glu Ile Glu Lys Glu Leu Arg Lys Ala Lys Arg Asp Ala Arg Arg
             20                  25                  30
Glu Leu Lys Leu Leu Leu Gly Thr Gly Glu Ser Gly Lys Ser Thr
         35                  40                  45
Phe Ile Lys Gln Met Arg Ile Ile His Gly Thr Gly Tyr Ser Glu Glu
     50                  55                  60
Asp Lys Arg Gly Phe Ile Lys Ile Val Tyr Gln Asn Ile Phe Met Ala
 65                  70                  75                  80
Met His Ser Met Ile Arg Ala Met Asp Thr Ile Lys Ile Ser Phe Glu
                 85                  90                  95
Val Ala Asp Asn Glu Glu Asn Ala Ile Met Ile Arg Gln Val Asp Tyr
                100                 105                 110
Glu Thr Val Thr Thr Leu Asp Ser Gln Ser Val Glu Ala Ile Leu Ser
            115                 120                 125
Leu Trp Ala Asp Ala Gly Ile Gln Glu Cys Tyr Asp Arg Arg Arg Glu
130                 135                 140
Tyr Gln Leu Thr Asp Ser Ala Lys Tyr Tyr Leu Asp Ala Val Asp Arg
145                 150                 155                 160
Ile Ala Glu Pro Asn Tyr Leu Pro Thr Leu Gln Asp Ile Leu Arg Val
                165                 170                 175
Arg Val Pro Thr Thr Gly Ile Ile Glu Tyr Pro Phe Asp Leu Asp Ser
            180                 185                 190
Ile Ile Phe Arg Met Val Asp Val Gly Gly Gln Arg Ser Glu Arg Arg
        195                 200                 205
Lys Trp Ile His Cys Phe Glu Asn Val Thr Ser Ile Met Phe Leu Val
210                 215                 220
Ala Leu Ser Glu Tyr Asp Gln Val Leu Val Glu Ser Asp Asn Glu Asn
225                 230                 235                 240
Arg Met Glu Glu Ser Lys Ala Leu Phe Arg Thr Ile Ile Thr Tyr Pro
                245                 250                 255
Trp Phe Gln Asn Ser Ser Val Ile Leu Phe Leu Asn Lys Lys Asp Leu
            260                 265                 270
Leu Glu Glu Lys Ile Met His Ser His Leu Val Asp Tyr Phe Pro Glu
        275                 280                 285
Phe Asp Gly Gln Lys Lys Asp Ala Gln Gly Ala Arg Glu Phe Ile Leu
290                 295                 300
Arg Met Phe Val Asp Leu Asn Pro Asp Pro Asp Lys Ile Ile Tyr Ser
305                 310                 315                 320
His Phe Thr Cys Ala Thr Asp Thr Glu Asn Ile Arg Phe Val Phe Ala
                325                 330                 335
Ala Val Lys Asp Thr Ile Leu Gln Leu Asn Leu Lys Glu Tyr Asn Leu
            340                 345                 350
Val
```

<210> SEQ ID NO 11
<211> LENGTH: 353
<212> TYPE: PRT
<213> ORGANISM: Lymnaea stagnalis -continued

```
<400> SEQUENCE: 11

Met Ala Cys Cys Ile Pro Asp Glu Leu Lys Glu Gln Lys Arg Ile Asn
  1               5                  10                  15

Gln Glu Ile Glu Arg Gln Leu Lys Arg Asp Lys Arg Asp Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Ala Gly Tyr Ser Asp Glu
 50                  55                  60

Asp Lys Arg Ser His Ile Lys Ile Val Tyr Gln Asn Ile Phe Met Ala
 65                  70                  75                  80

Met His Ala Met Ile Arg Ala Met Asp Thr Leu Asn Ile Gln Tyr Ile
                 85                  90                  95

Asn Pro Ala Asn Arg Glu Asn Gly Asn Met Ile Arg Gln Ile Asp Tyr
                100                 105                 110

Glu Thr Val Thr Thr Phe Asp Lys Pro Cys Val Asp Ala Ile Ile Ser
                115                 120                 125

Leu Trp Asn Asp Asp Gly Ile Gln Glu Cys Tyr Asp Arg Arg Arg Glu
130                 135                 140

Tyr Gln Leu Thr Asp Ser Ala Lys Tyr Tyr Leu Asp Ser Val Glu Arg
145                 150                 155                 160

Ile Ser Gln Gln Asp Tyr Leu Pro Thr Leu Gln Asp Ile Leu Arg Val
                165                 170                 175

Arg Val Pro Thr Thr Gly Ile Ile Glu Tyr Pro Phe Asp Leu Asp Ser
                180                 185                 190

Ile Ile Phe Arg Met Val Asp Val Gly Gly Gln Arg Ser Glu Arg Arg
                195                 200                 205

Lys Trp Ile His Cys Phe Glu Asn Val Thr Ser Ile Met Phe Leu Val
210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
                260                 265                 270

Leu Glu Glu Lys Ile Met His Ser His Leu Val Asp Tyr Phe Pro Glu
                275                 280                 285

Phe Asp Gly Pro Lys Lys Glu Ala Ser Thr Ala Arg Glu Phe Ile Leu
290                 295                 300

Lys Met Phe Val Glu Leu Asn Pro Asp Pro Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
                340                 345                 350

Val

<210> SEQ ID NO 12
<211> LENGTH: 353
<212> TYPE: PRT
<213> ORGANISM: Drosophila melanogaster
```

```
<400> SEQUENCE: 12

Met Glu Cys Cys Leu Ser Glu Glu Ala Lys Glu Gln Lys Arg Ile Asn
 1               5                  10                  15

Gln Glu Ile Glu Lys Gln Leu Arg Arg Asp Lys Arg Asp Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Ser Gly Tyr Ser Asp Glu
     50                  55                  60

Asp Lys Arg Gly Tyr Ile Lys Leu Val Phe Gln Asn Ile Phe Met Ala
 65                  70                  75                  80

Met Gln Ser Met Ile Lys Ala Met Asp Met Leu Lys Ile Ser Tyr Gly
                 85                  90                  95

Gln Gly Glu His Ser Glu Leu Ala Asp Leu Val Met Ser Ile Asp Tyr
             100                 105                 110

Glu Thr Val Thr Thr Phe Glu Asp Pro Tyr Leu Asn Ala Ile Lys Thr
         115                 120                 125

Leu Trp Asp Asp Ala Gly Ile Gln Glu Cys Tyr Asp Arg Arg Arg Glu
    130                 135                 140

Tyr Gln Leu Thr Asp Ser Ala Lys Tyr Tyr Leu Ser Asp Leu Ala Arg
145                 150                 155                 160

Ile Glu Gln Ala Asp Tyr Leu Pro Thr Glu Gln Asp Ile Leu Arg Ala
                165                 170                 175

Arg Val Pro Thr Thr Gly Ile Leu Glu Tyr Pro Phe Asp Leu Asp Gly
            180                 185                 190

Ile Val Phe Arg Met Val Asp Val Gly Gly Gln Arg Ser Glu Arg Arg
        195                 200                 205

Lys Trp Ile His Cys Phe Glu Asn Val Thr Ser Ile Ile Phe Leu Val
    210                 215                 220

Ala Leu Ser Glu Tyr Asp Gln Ile Leu Phe Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Lys Gln Asp His Ala Ala Ala Lys Gln Phe Val Leu
    290                 295                 300

Lys Lys Tyr Leu Ala Cys Asn Pro Asp Pro Glu Arg Gln Cys Tyr Ser
305                 310                 315                 320

His Phe Thr Thr Ala Thr Asp Thr Glu Asn Ile Lys Leu Val Phe Cys
                325                 330                 335

Ala Val Lys Asp Thr Ile Met Gln Asn Ala Leu Lys Glu Phe Asn Leu
            340                 345                 350

Gly

<210> SEQ ID NO 13
<211> LENGTH: 353
<212> TYPE: PRT
<213> ORGANISM: Drosophila melanogaster
```

<400> SEQUENCE: 13

| | | | | | | | | | | | | | | | |
|---|---|---|---|---|---|---|---|---|---|---|---|---|---|---|---|
|Met|Glu|Cys|Cys|Leu|Ser|Glu|Glu|Ala|Lys|Glu|Gln|Lys|Arg|Ile|Asn|
|1| | | |5| | | | |10| | | | |15| |
|Gln|Glu|Ile|Glu|Lys|Gln|Leu|Arg|Arg|Asp|Lys|Arg|Asp|Ala|Arg|Arg|
| | | |20| | | | |25| | | | |30| | |
|Glu|Leu|Lys|Leu|Leu|Leu|Gly|Thr|Gly|Glu|Ser|Gly|Lys|Ser|Thr| |
| | |35| | | | |40| | | | |45| | | |
|Phe|Ile|Lys|Gln|Met|Arg|Ile|Ile|His|Gly|Ser|Gly|Tyr|Ser|Asp|Glu|
| |50| | | | |55| | | | |60| | | | |
|Asp|Lys|Arg|Gly|Tyr|Ile|Lys|Leu|Val|Phe|Gln|Asn|Ile|Phe|Met|Ala|
|65| | | | |70| | | | |75| | | | |80|
|Met|Gln|Ser|Met|Ile|Lys|Ala|Met|Asp|Met|Leu|Lys|Ile|Ser|Tyr|Gly|
| | | | |85| | | | |90| | | | |95| |
|Gln|Gly|Glu|His|Ser|Glu|Leu|Ala|Asp|Leu|Val|Met|Ser|Ile|Asp|Tyr|
| | | |100| | | | |105| | | | |110| | |
|Glu|Thr|Val|Thr|Thr|Phe|Glu|Asp|Pro|Tyr|Leu|Asn|Ala|Ile|Lys|Thr|
| | |115| | | | |120| | | | |125| | | |
|Leu|Trp|Asp|Asp|Ala|Gly|Ile|Gln|Glu|Cys|Tyr|Asp|Arg|Arg|Arg|Glu|
| |130| | | | |135| | | | |140| | | | |
|Tyr|Gln|Leu|Thr|Asp|Ser|Ala|Lys|Tyr|Tyr|Leu|Lys|Asp|Leu|Asp|Arg|
|145| | | | |150| | | | |155| | | | |160|
|Val|Ala|Gln|Pro|Ala|Tyr|Leu|Pro|Thr|Glu|Gln|Asp|Ile|Leu|Arg|Val|
| | | | |165| | | | |170| | | | |175| |
|Arg|Val|Pro|Thr|Thr|Gly|Ile|Ile|Glu|Tyr|Pro|Phe|Asp|Leu|Glu|Glu|
| | | |180| | | | |185| | | | |190| | |
|Ile|Arg|Phe|Arg|Met|Val|Asp|Val|Gly|Gly|Gln|Arg|Ser|Glu|Arg|Arg|
| | |195| | | | |200| | | | |205| | | |
|Lys|Trp|Ile|His|Cys|Phe|Glu|Asn|Val|Thr|Ser|Ile|Ile|Phe|Leu|Val|
| |210| | | | |215| | | | |220| | | | |
|Ala|Leu|Ser|Glu|Tyr|Asp|Gln|Ile|Leu|Phe|Glu|Ser|Asp|Asn|Glu|Asn|
|225| | | | |230| | | | |235| | | | |240|
|Arg|Met|Glu|Glu|Ser|Lys|Ala|Leu|Phe|Arg|Thr|Ile|Ile|Thr|Tyr|Pro|
| | | | |245| | | | |250| | | | |255| |
|Trp|Phe|Gln|Asn|Ser|Ser|Val|Ile|Leu|Phe|Leu|Asn|Lys|Lys|Asp|Leu|
| | | |260| | | | |265| | | | |270| | |
|Leu|Glu|Glu|Lys|Ile|Met|Tyr|Ser|His|Leu|Val|Asp|Tyr|Phe|Pro|Glu|
| | |275| | | | |280| | | | |285| | | |
|Tyr|Asp|Gly|Pro|Gln|Arg|Asp|Ala|Ile|Thr|Ala|Arg|Glu|Phe|Ile|Leu|
| |290| | | | |295| | | | |300| | | | |
|Arg|Met|Phe|Val|Asp|Leu|Asn|Pro|Asp|Ser|Glu|Lys|Ile|Ile|Tyr|Ser|
|305| | | | |310| | | | |315| | | | |320|
|His|Phe|Thr|Cys|Ala|Thr|Asp|Thr|Glu|Asn|Ile|Arg|Phe|Val|Phe|Ala|
| | | | |325| | | | |330| | | | |335| |
|Ala|Val|Lys|Asp|Thr|Ile|Leu|Gln|Ser|Asn|Leu|Lys|Glu|Tyr|Asn|Leu|
| | | |340| | | | |345| | | | |350| | |
|Val| | | | | | | | | | | | | | | |

<210> SEQ ID NO 14
<211> LENGTH: 353
<212> TYPE: PRT
<213> ORGANISM: Homarus americanus

```
<400> SEQUENCE: 14

Met Ala Cys Cys Leu Ser Glu Glu Ala Lys Glu Gln Lys Arg Ile Asn
 1               5                  10                  15

Gln Glu Ile Glu Arg Gln Leu Arg Lys Asp Lys Arg Asp Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Ala Gly Tyr Ser Asp Glu
         50                  55                  60

Asp Lys Arg Gly Phe Ile Lys Leu Val Phe Gln Asn Ile Phe Met Ala
 65                  70                  75                  80

Met Gln Ser Met Ile Arg Ala Met Asp Leu Leu Gln Ile Ser Tyr Gly
                 85                  90                  95

Asp Ser Ala Asn Ile Glu His Ala Asp Leu Val Arg Ser Val Asp Tyr
                100                 105                 110

Glu Ser Val Thr Thr Phe Glu Glu Pro Tyr Val Thr Ala Met Asn Ser
            115                 120                 125

Leu Trp Gln Asp Thr Gly Ile Gln His Cys Tyr Asp Arg Arg Arg Glu
130                 135                 140

Tyr Gln Leu Thr Asp Ser Ala Lys Tyr Tyr Leu Thr Asp Leu Asp Arg
145                 150                 155                 160

Ile Ala Ala Lys Asp Tyr Val Ser Thr Leu Gln Asp Ile Leu Arg Val
                165                 170                 175

Arg Ala Pro Thr Thr Gly Ile Ile Glu Tyr Pro Phe Asp Leu Glu Glu
                180                 185                 190

Ile Arg Phe Arg Met Val Asp Val Gly Gly Gln Arg Ser Glu Arg Arg
        195                 200                 205

Lys Trp Ile His Cys Phe Glu Asn Val Thr Ser Ile Ile Phe Leu Val
210                 215                 220

Ala Leu Ser Glu Tyr Asp Gln Ile Leu Phe Glu Ser Asp Asn Glu Asn
225                 230                 235                 240

Arg Met Glu Glu Ser Lys Ala Leu Phe Lys Thr Ile Ile Thr Tyr Pro
                245                 250                 255

Trp Phe Gln His Ser Ser Val Ile Leu Phe Leu Asn Lys Lys Asp Leu
                260                 265                 270

Leu Glu Glu Lys Ile Met Tyr Ser His Leu Val Asp Tyr Phe Pro Glu
            275                 280                 285

Tyr Asp Gly Pro Arg Lys Asp Ala Ile Ala Ala Arg Glu Phe Ile Leu
290                 295                 300

Arg Met Phe Val Glu Leu Asn Pro Asp Pro Glu Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
            340                 345                 350

Val

<210> SEQ ID NO 15
<211> LENGTH: 353
<212> TYPE: PRT
<213> ORGANISM: Limulus polyphemus
```

```
<400> SEQUENCE: 15

Met Ala Cys Cys Leu Ser Glu Glu Gly Lys Glu Gln Lys Arg Ile Asn
  1               5                  10                  15

Gln Glu Ile Glu Arg Gln Leu Arg Lys Asp Lys Arg Asp Ala Arg Arg
             20                  25                  30

Glu Leu Lys Leu Leu Leu Gly Thr Gly Glu Ser Gly Lys Ser Thr
         35                  40                  45

Phe Ile Lys Gln Met Arg Ile Ile His Gly Gln Gly Tyr Ser Asp Asp
 50                  55                  60

Asp Lys Lys Ser Tyr Ile Lys Leu Val Tyr Gln Asn Ile Ile Met Ala
 65                  70                  75                  80

Met Gln Ser Met Asn Lys Ala Met Glu Met Leu Lys Ile Ser Tyr Lys
                 85                  90                  95

Asp Arg Asn Asn Ile Glu Asn Ala Glu Leu Val Leu Ser Val Asp Tyr
                100                 105                 110

Glu Thr Val Thr Thr Phe Asp Ser Pro Tyr Val Glu Ala Ile Lys Ser
            115                 120                 125

Leu Trp Val Asp Pro Gly Ile Gln Glu Cys Tyr Asp Arg Arg Arg Glu
        130                 135                 140

Tyr Gln Leu Thr Asp Ser Ala Lys Tyr Tyr Leu Asn Asp Ile Asp Arg
145                 150                 155                 160

Ile Ala Val Pro Asn Tyr Leu Pro Thr Gln Gln Asp Ile Leu Arg Val
                165                 170                 175

Arg Val Pro Thr Thr Gly Ile Ile Glu Tyr Pro Phe Ile Leu Asp Ser
            180                 185                 190

Ile Ile Phe Arg Met Val Asp Val Gly Gly Gln Arg Ser Glu Arg Arg
        195                 200                 205

Lys Trp Ile His Cys Phe Glu Asn Val Thr Ser Ile Ile Phe Leu Val
210                 215                 220

Ala Leu Ser Glu Tyr Asp Gln Ile Leu Phe Glu Ser Asp Asn Glu Asn
225                 230                 235                 240

Arg Met Glu Glu Ser Lys Ala Leu Phe Lys Thr Ile Ile Thr Tyr Pro
                245                 250                 255

Trp Phe Leu Asn Ser Ser Val Ile Leu Phe Leu Asn Lys Lys Asp Leu
                260                 265                 270

Leu Glu Glu Lys Ile Met Phe Ser His Leu Val Asp Tyr Phe Pro Glu
            275                 280                 285

Tyr Asp Gly Pro Lys Lys Asp Ala Val Gln Gly Arg Glu Phe Ile Leu
290                 295                 300

Lys Met Phe Val Asp Leu Asn Pro Asp Ser Glu Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Leu
                340                 345                 350

Val

<210> SEQ ID NO 16
<211> LENGTH: 354
<212> TYPE: PRT
<213> ORGANISM: Loligo forbesi
```

```
<400> SEQUENCE: 16

Met Ala Cys Cys Leu Ser Glu Glu Ala Lys Glu Gln Lys Arg Ile Asn
  1               5                  10                  15

Gln Glu Ile Glu Lys Gln Leu Arg Arg Asp Lys Arg Asp Ala Arg Arg
                 20                  25                  30

Glu Leu Lys Leu Leu Leu Gly Thr Gly Glu Ser Gly Lys Ser Thr
             35                  40                  45

Phe Ile Lys Gln Met Arg Ile Ile His Gly Ser Gly Tyr Ser Glu Glu
             50                  55                  60

Asp Arg Lys Gly Phe Glu Lys Ile Val Tyr Gln Asn Ile Phe Ser Ala
 65                  70                  75                  80

Ile Gln Thr Leu Ile Ala Ala Met Glu Thr Leu Ser Leu Glu Tyr Lys
                 85                  90                  95

Asp Pro Ser Asn Asn Glu His Ala Glu Phe Leu Asn Ser Ile Asp Ala
                100                 105                 110

Asp Ser Ala Asp Ile Phe Glu Asp Gly His Val Thr Ala Ile Lys Gly
            115                 120                 125

Cys Trp Thr Asp Pro Gly Met Gln Glu Cys Tyr Asp Arg Arg Arg Glu
130                 135                 140

Tyr Gln Leu Thr Asp Ser Ala Lys Tyr Tyr Leu Asp Asp Val Glu Arg
145                 150                 155                 160

Ile His Glu Pro Gly Tyr Ile Pro Thr Leu Gln Asp Ile Leu Arg Val
                165                 170                 175

Arg Val Pro Thr Thr Gly Ile Ile Glu Tyr Pro Phe Asp Leu Tyr Ser
            180                 185                 190

Ile Ile Phe Arg Met Val Asp Val Gly Gly Gln Arg Ser Glu Arg Arg
            195                 200                 205

Lys Trp Ile His Cys Phe Glu Asn Val Thr Ser Ile Met Phe Leu Val
210                 215                 220

Ala Leu Ser Glu Tyr Asp Gln Val Leu Val Glu Ser Asp Asn Glu Glu
225                 230                 235                 240

Asn Arg Met Glu Glu Ser Lys Ala Leu Phe Arg Thr Ile Ile Thr Tyr
                245                 250                 255

Pro Trp Phe Gln Asn Ser Ser Val Ile Leu Phe Leu Asn Lys Lys Asp
                260                 265                 270

Leu Leu Glu Glu Lys Ile Met Thr Ser His Leu Ala Asp Tyr Phe Pro
            275                 280                 285

Asp Tyr Asp Gly Pro Lys Cys Asp Tyr Glu Ala Ala Arg Glu Phe Met
290                 295                 300

Met Asp Ser Tyr Met Asp Leu Asn Glu Asp Lys Glu Lys Met Leu Tyr
305                 310                 315                 320

Tyr His Tyr Thr Cys Ala Thr Asp Thr Glu Asn Ile Arg Phe Val Phe
                325                 330                 335

Ala Ala Val Lys Asp Thr Ile Leu Gln Leu Asn Leu Lys Glu Tyr Asn
            340                 345                 350

Leu Val

<210> SEQ ID NO 17
<211> LENGTH: 355
<212> TYPE: PRT
<213> ORGANISM: Caenorhabditis elegans
```

```
<400> SEQUENCE: 17

Met Ala Cys Cys Leu Ser Glu Glu Ala Arg Glu Gln Lys Arg Ile Asn
 1               5                  10                  15

Gln Glu Ile Glu Lys Gln Leu Gln Arg Asp Lys Arg Asn Ala Arg Arg
                20                  25                  30

Glu Leu Lys Leu Leu Leu Gly Thr Gly Glu Ser Gly Lys Ser Thr
            35                  40                  45

Phe Ile Lys Gln Met Arg Ile Ile His Gly Gln Gly Tyr Ser Glu Glu
        50                  55                  60

Asp Lys Arg Ala His Ile Arg Leu Val Tyr Gln Asn Val Phe Met Ala
65                  70                  75                  80

Ile Gln Ser Met Ile Arg Ala Met Asp Thr Leu Asp Ile Lys Phe Gly
                85                  90                  95

Asn Glu Ser Glu Glu Leu Gln Glu Lys Ala Ala Val Val Arg Glu Val
                100                 105                 110

Asp Phe Glu Ser Val Thr Ser Phe Glu Glu Pro Tyr Val Ser Tyr Ile
            115                 120                 125

Lys Glu Leu Trp Glu Asp Ser Gly Ile Gln Glu Cys Tyr Asp Arg Arg
    130                 135                 140

Arg Glu Tyr Gln Leu Thr Asp Ser Ala Lys Tyr Tyr Leu Ser Asp Leu
145                 150                 155                 160

Arg Arg Leu Ala Val Pro Asp Tyr Leu Pro Thr Glu Gln Asp Ile Leu
                165                 170                 175

Arg Val Arg Val Pro Thr Thr Gly Ile Ile Glu Tyr Pro Phe Asp Leu
            180                 185                 190

Glu Gln Ile Ile Phe Arg Met Val Asp Val Gly Gly Gln Arg Ser Glu
        195                 200                 205

Arg Arg Lys Trp Ile His Cys Phe Glu Asn Val Thr Ser Ile Met Phe
    210                 215                 220

Leu Val Ala Leu Ser Glu Tyr Asp Gln Val Leu Val Glu Cys Asp Asn
225                 230                 235                 240

Glu Asn Arg Met Glu Glu Ser Lys Ala Leu Phe Arg Thr Ile Ile Thr
                245                 250                 255

Tyr Pro Trp Phe Thr Asn Ser Ser Val Ile Leu Phe Leu Asn Lys Lys
            260                 265                 270

Asp Leu Leu Glu Glu Lys Ile Leu Tyr Ser His Leu Ala Asp Tyr Phe
        275                 280                 285

Pro Glu Tyr Asp Gly Pro Pro Arg Asp Pro Ile Ala Ala Arg Glu Phe
    290                 295                 300

Ile Leu Lys Met Phe Val Asp Leu Asn Pro Asp Ala Asp Lys Ile Ile
305                 310                 315                 320

Tyr Ser His Phe Thr Cys Ala Thr Asp Thr Glu Asn Ile Arg Phe Val
                325                 330                 335

Phe Ala Ala Val Lys Asp Thr Ile Leu Gln His Asn Leu Lys Glu Tyr
            340                 345                 350

Asn Leu Val
    355

<210> SEQ ID NO 18
<211> LENGTH: 355
<212> TYPE: PRT
<213> ORGANISM: Geodia cydonium
```

-continued

```
<400> SEQUENCE: 18

Met Ser Cys Leu Leu Ser Glu Glu Arg Leu Gln Lys Arg Ile Asn
 1               5                  10                  15

Thr Arg Ile Asn Arg Glu Leu Gln Arg Asp His Lys Asp Ala Lys Lys
            20                  25                  30

Glu Ile Lys Leu Leu Leu Gly Thr Gly Glu Ser Gly Lys Ser Thr
            35                  40                  45

Phe Ile Lys Gln Met Arg Ile Ile His Gly Lys Gly Tyr Ser Lys Gln
        50                  55                  60

Asp Cys Leu Glu Tyr Lys Asn Leu Val Phe Arg Asn Ile Leu Met Ser
 65                 70                  75                  80

Met His Ser Met Leu Gln Ala Thr Ala Glu Leu Lys Ile Ala Tyr Ile
                85                  90                  95

Asp Pro Asp Ala Gln Arg His Val Gln Leu Leu Met Ala Leu Arg Pro
               100                 105                 110

Glu Thr Ala Gln Ser Leu Gly Gly Glu Thr Cys Glu Ala Ile Arg Lys
           115                 120                 125

Leu Trp Gln Asp Ala Gly Val Gln Glu Cys Tyr Gln Arg Arg Asn Glu
130                 135                 140

Tyr Gln Leu Ser Asp Ser Thr Lys Tyr Tyr Leu Asp Asp Leu Pro Arg
145                 150                 155                 160

Ile Ser Ser Asn Asp Tyr Val Pro Thr Thr Gln Asp Val Leu Arg Val
                165                 170                 175

Arg Val Pro Thr Thr Gly Ile Asn Glu Tyr Pro Phe Thr Ile Asn Lys
            180                 185                 190

Ile Ile Phe Lys Met Val Asp Val Gly Gly Gln Arg Ser Glu Arg Arg
        195                 200                 205

Lys Trp Ile His Cys Phe Asp His Val Thr Ser Val Met Phe Leu Val
    210                 215                 220

Ala Ile Ser Glu Tyr Asp Gln Ile Leu Val Glu Ala Asp Ser Arg Val
225                 230                 235                 240

Asn Arg Met Val Glu Ser Leu His Leu Phe Asn Thr Ile Ile Ser Tyr
                245                 250                 255

Pro Trp Phe Asn Lys Ser Ser Ile Ile Leu Phe Leu Asn Lys Lys Asp
            260                 265                 270

Leu Leu Glu Glu Lys Val Met His Ser His Leu Ile Asp Tyr Phe Glu
        275                 280                 285

Glu Tyr Asp Gly Pro Lys Cys Asp His Val Ser Ala Arg Glu Ser Ile
    290                 295                 300

Ala Lys Met Phe Ile Ser Ile Asn Asp Met Arg Ser Ala Asp Ile Tyr
305                 310                 315                 320

Pro His Phe Thr Cys Ala Thr Asp Thr Glu Asn Ile Lys Phe Val Phe
                325                 330                 335

Asp Val Val Lys Asn His Ile Leu Gln Gln His Ile Thr Glu Val Val
            340                 345                 350

Pro Gly Leu
        355

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: primer
```

```
<400> SEQUENCE: 19
gaatatgatg gaccccagag agatg                                              25

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 20
gatcctcgag ttagcacagt ccgatgtact tcaggttcaa ctggaggatg gt                52

<210> SEQ ID NO 21
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 21
gatcctcgag ttagtacagt ccgcatccct tcaggttcaa ctggaggatg gt                52

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 22
gatcctcgag ttagtaaagc ccacattcct tcaggttcaa ctggaggatg gt                52

<210> SEQ ID NO 23
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 23
gatcctcgag ttagagcagc tcgtattgct tcaggttcaa ctggaggatg gt                52

<210> SEQ ID NO 24
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 24
ggaaaaaagc ggccgcttaa aacagtccgc agtccttcag gttcaactgg aggatggt         58

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 25
ggggtaccgc cgccatggcc tgctgttttat cc                                     32
```

```
<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 26
gctctagatt acaccaagtt gtactccttc agatt                              35

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 27
ctctccgatc tccgacggct g                                             21

<210> SEQ ID NO 28
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 28
ttctacagca taatctgaag tatatcggtt tgtgttaatc tagagggccc gtttaaaccc   60
gctg                                                                64

<210> SEQ ID NO 29
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 29
cagcgggttt aaacgggccc tctagattaa cacaaaccga tatacttcag attatgctgt   60
agaa                                                                64

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 30
cagcataatc tgaaggagtg tggattgtac taatctagag ggcccg                  46

<210> SEQ ID NO 31
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 31
cgggccctct agattagtac aatccacact ccttcagatt atgctg                  46
```

<210> SEQ ID NO 32
<211> LENGTH: 69
<212> TYPE: DNA
<213> ORGANISM: Artificial Sequence
<220> FEATURE:
<223> OTHER INFORMATION: Description of Artificial Sequence: primer

<400> SEQUENCE: 32
ggaaaaaagc ggccgcttag agcagctcgt attgcctcag gtgcatctgg aggatggtgt    60
ccttgacgg                                                            69

<210> SEQ ID NO 33
<211> LENGTH: 63
<212> TYPE: DNA
<213> ORGANISM: Artificial Sequence
<220> FEATURE:
<223> OTHER INFORMATION: Description of Artificial Sequence: primer

<400> SEQUENCE: 33
gctctagatt agagcagctc gtattgcctc aggtgcatct gtagaattgt gtctttgacg    60
gcg                                                                  63

<210> SEQ ID NO 34
<211> LENGTH: 63
<212> TYPE: DNA
<213> ORGANISM: Artificial Sequence
<220> FEATURE:
<223> OTHER INFORMATION: Description of Artificial Sequence: primer

<400> SEQUENCE: 34
gctctagatt aacatagccc tatgtatttt agattattct gtagaattgt gtctttgacg    60
gcg                                                                  63

<210> SEQ ID NO 35
<211> LENGTH: 98
<212> TYPE: DNA
<213> ORGANISM: Artificial Sequence
<220> FEATURE:
<223> OTHER INFORMATION: Description of Artificial Sequence: primer

<400> SEQUENCE: 35
gctctagatt agagcagctc gtattgcctc aggtgcatac gttgaataat gtcacgacag    60
tcattaaaaa cacgccgaat gttttccgta tcagtcgc                            98

<210> SEQ ID NO 36
<211> LENGTH: 6
<212> TYPE: PRT
<213> ORGANISM: vertebrate

<400> SEQUENCE: 36

Met Thr Leu Glu Ser Ile
 1               5

<210> SEQ ID NO 37
<211> LENGTH: 21
<212> TYPE: PRT
<213> ORGANISM: invertebrate

<400> SEQUENCE: 37

Phe Val Phe Ala Ala Val Lys Asp Thr Ile Leu Gln His Asn Leu Lys
 1               5                   10                  15

Glu Tyr Asn Leu Val
            20

```
<210> SEQ ID NO 38
<211> LENGTH: 21
<212> TYPE: PRT
<213> ORGANISM: vertebrate

<400> SEQUENCE: 38

Phe Val Phe Asp Ala Val Thr Asp Val Ile Ile Gln Asn Asn Leu Lys
 1               5                  10                  15

Tyr Ile Gly Leu Cys
            20

<210> SEQ ID NO 39
<211> LENGTH: 21
<212> TYPE: PRT
<213> ORGANISM: vertebrate

<400> SEQUENCE: 39

Arg Val Phe Asn Asp Cys Arg Asp Ile Ile Gln Arg Met His Leu Arg
 1               5                  10                  15

Gln Tyr Glu Leu Leu
            20

<210> SEQ ID NO 40
<211> LENGTH: 21
<212> TYPE: PRT
<213> ORGANISM: vertebrate

<400> SEQUENCE: 40

Phe Val Phe Asp Ala Val Thr Asp Val Ile Ile Lys Asn Asn Leu Lys
 1               5                  10                  15

Glu Cys Gly Leu Tyr
            20

<210> SEQ ID NO 41
<211> LENGTH: 353
<212> TYPE: PRT
<213> ORGANISM: Drosophila melanogaster

<400> SEQUENCE: 41

Met Glu Cys Cys Leu Ser Glu Glu Ala Lys Glu Gln Lys Arg Ile Asn
 1               5                  10                  15

Gln Glu Ile Glu Lys Gln Leu Arg Arg Asp Lys Arg Asp Ala Arg Arg
            20                  25                  30

Glu Leu Lys Leu Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
    50                  55                  60

Asp Lys Arg Gly Tyr Ile Lys Leu Val Phe Gln Asn Ile Phe Met Ala
65                  70                  75                  80

Met Gln Ser Met Ile Lys Ala Met Asp Met Leu Lys Ile Ser Tyr Gly
                85                  90                  95

Gln Gly Glu His Ser Glu Leu Ala Asp Leu Val Met Ser Ile Asp Tyr
            100                 105                 110

Glu Thr Val Thr Thr Phe Glu Asp Pro Tyr Leu Asn Ala Ile Lys Thr
        115                 120                 125

Leu Trp Asp Asp Ala Gly Ile Gln Glu Cys Tyr Asp Arg Arg Arg Glu
    130                 135                 140

Tyr Gln Leu Thr Asp Ser Ala Lys Tyr Tyr Leu Lys Asp Leu Asp Arg
145                 150                 155                 160
```

-continued

```
Val Ala Gln Pro Ala Tyr Leu Pro Thr Glu Gln Asp Ile Leu Arg Val
                165                 170                 175

Arg Val Pro Thr Thr Gly Ile Ile Glu Tyr Pro Phe Asp Leu Glu Glu
            180                 185                 190

Ile Arg Phe Arg Met Val Asp Val Gly Gly Gln Arg Ser Glu Arg Arg
        195                 200                 205

Lys Trp Ile His Cys Phe Glu Asn Val Thr Ser Ile Ile Phe Leu Val
    210                 215                 220

Ala Leu Ser Glu Tyr Asp Gln Ile Leu Phe Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Ile Thr Ala Arg Glu Phe Ile Leu
    290                 295                 300

Arg Met Phe Val Asp Leu Asn Pro Asp Ser Glu Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Ser Asn Leu Lys Tyr Ile Gly Leu
            340                 345                 350

Cys
```

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 42
cggggtaccc cggttagcat ggagtgctgt ttatcg                                    36

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 43
ccggaattcc ggttagacca aattatattc cttaaggttc                                40

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 44
gagcatcgat tacgagaccg ttacc                                                25

<210> SEQ ID NO 45
<211> LENGTH: 53
<212> TYPE: DNA
<213> ORGANISM: Artificial Sequence

```
-continued

<220> FEATURE:
<223> OTHER INFORMATION: Description of Artificial Sequence: primer

<400> SEQUENCE: 45
cggaattctt agcacagtcc gatgtactta aggttcgatt gcagaattgt gtc          53
```